US009295654B2

(12) United States Patent
Barbe et al.

(10) Patent No.: US 9,295,654 B2
(45) Date of Patent: *Mar. 29, 2016

(54) LAYERED NANOPARTICLES

(71) Applicant: AUSTRALIAN NUCLEAR SCIENCE & TECHNOLOGY ORGANISATION, Lucas Heights, New South Wales (AU)

(72) Inventors: Christophe Jean Alexandre Barbe, Five Dock (AU); Linggen Kong, Narwee (AU)

(73) Assignee: AUSTRALIAN NUCLEAR SCIENCE & TECHNOLOGY ORGANISATION, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/477,525

(22) Filed: Sep. 4, 2014

(65) Prior Publication Data
US 2015/0086479 A1    Mar. 26, 2015

Related U.S. Application Data

(62) Division of application No. 11/816,052, filed as application No. PCT/AU2006/000193 on Feb. 14, 2006, now Pat. No. 8,871,272.

(30) Foreign Application Priority Data

Feb. 14, 2005  (AU) ................ 2005900677

(51) Int. Cl.
| A61K 9/14 | (2006.01) |
| A61K 9/16 | (2006.01) |
| A61K 9/50 | (2006.01) |
| A61K 9/00 | (2006.01) |
| A61K 9/51 | (2006.01) |
| A61K 47/02 | (2006.01) |
| C01B 33/142 | (2006.01) |
| C01B 33/149 | (2006.01) |
| A61K 49/00 | (2006.01) |
| A61K 51/12 | (2006.01) |

(52) U.S. Cl.
CPC ............ *A61K 9/5115* (2013.01); *A61K 9/5192* (2013.01); *A61K 47/02* (2013.01); *A61K 49/0093* (2013.01); *A61K 51/1244* (2013.01); *C01B 33/142* (2013.01); *C01B 33/149* (2013.01); *Y10T 428/2991* (2015.01)

(58) Field of Classification Search
None
See application file for complete search history.

(56) References Cited

U.S. PATENT DOCUMENTS

| 5,024,826 | A | 6/1991 | Linton |
| 5,326,692 | A | 7/1994 | Brinkley et al. |
| 6,548,264 | B1 | 4/2003 | Tan et al. |
| 6,602,932 | B2* | 8/2003 | Feldheim et al. ............ 523/201 |
| 7,258,874 | B2 | 8/2007 | Barbe et al. |
| 8,871,272 | B2* | 10/2014 | Kong et al. .................. 424/490 |
| 2002/0177311 | A1 | 11/2002 | Schumacher et al. |
| 2003/0157330 | A1 | 8/2003 | Ostafin et al. |
| 2003/0215638 | A1 | 11/2003 | Charnay et al. |
| 2006/0093670 | A1 | 5/2006 | Mizushima et al. |

FOREIGN PATENT DOCUMENTS

| JP | 07-053835 | 2/1995 |
| KR | 1999-009382 | 2/1999 |
| WO | 01/37721 | 5/2001 |
| WO | 01/40872 | 6/2001 |
| WO | 01/57144 | 8/2001 |
| WO | 01/62232 | 8/2001 |
| WO | 01/64164 | 9/2001 |
| WO | 01/88540 | 11/2001 |
| WO | 02/66574 | 2/2002 |
| WO | 02/080885 | 10/2002 |
| WO | 03/055469 | 7/2003 |
| WO | 04/000270 | 12/2003 |
| WO | 2006/050579 | 5/2006 |

OTHER PUBLICATIONS

Patent Abstracts of Japan, JP 07-053835 A, Feb. 28, 1995, abstract.
Patent Abstract of Japan, 2004-010403, Jan. 15, 2004, "Titanium Oxide Fine Particle with Multiple Structure, Method of Producing the Same, Photoelectric Conversion Element and Photoelectric Cell Comprising the Same," abstract.
Duan et al., "A Novel Nano-sensor Based on Fluorescent Core-shell Silica Nanoparticle for pH Measurements in Murine Macrophages," Journal of Hunan University (Natural Sciences), vol. 30, No. 2, Apr. 2003.
Lal et lal, "Silica Nanobubbles Containing an Organic Dye in a Multilayered Organic/Inorganic Hetereostructure with Enhanced Luminescence," Chem. Mater. 2000, 12, 2632-2639.

(Continued)

*Primary Examiner* — Jeffrey T Palenik
(74) *Attorney, Agent, or Firm* — Kagan Binder, PLLC

(57) ABSTRACT

The invention provides a process for forming a layered nanoparticle, comprising providing a suspension comprising a core particle in a first liquid, adding a second liquid to the suspension, and adding a reagent, or a precursor for the reagent, to the suspension. The second liquid is immiscible with the first liquid. If the reagent is added to the suspension, the reagent reacts to form a layer on the core particle to form the layered nanoparticle. If a precursor for the reagent is added to the suspension, the precursor is converted to the reagent, and the reagent reacts to form a layer on the core particle to form the layered nanoparticle.

8 Claims, 43 Drawing Sheets

(56) References Cited

OTHER PUBLICATIONS

Dooring et al., "Spectroscopic Tags Using Dye-Embedded Nanoparticles and Surface-Enhanced Raman Scattering," Anal. Chem. 2003, 75, 6171-6176.

Lu et al., "Synthesis and characterization of multi-functional nanoparticles processing magnetic, up-conversion fluorescence and bio-affinity properties," J. Mater. Chem. 2004, 14, 1336-1341.

Ethiraj et al., "Enhancement of photoluminescence in manganese-doped ZnS nanoparticles due to a silica shell," Journal of Chemical Physics, vol. 118, No. 19, May 15, 2003, 8945-8953.

Espiard et al., "Surface Functionalized Colloidal Silica Particles from an Inverse Microemulsion Sol Gel Process," Journal of Inorganic and Organometallic Polymers, vol. 5, No. 4, 1995, 391-407.

Kone et al., "Formation of Silico-antimonic core-shell particles with an antemonic acid core encapsulated with silica," Polyhedron vol. 8, No. 21, 2577-2585, 1989.

Das et al., "Inorganic-Organic Hybrid Nanoparticles from n-Octyl Triethoxy Silane," Journal of Colloid and Interface Science 252, 82-88, 2002.

Roorda et al., "Aligned Gold Nanorods in Silica Made by Ion Irradiation of Core Shell Colloidal Particles," Adv. Mater. 2004, 16, No. 3, Feb. 3, 2004, 235-237.

Sameti et al., "Stabilisation by freeze-drying of cationically modified silica nanoparticles for gene delivery," International Journal of Pharmaceutics 266, 2003, 51-60.

Yu et al., "Synthesis and Characterization of Gold-Silica Nanoparticles Incorporating a Mercaptosilane Core-Shell Interface," Langmuir 18, 8566-8572, 2002.

Shartl, "Crosslinked Spherical Nanoparticles with Core-Shell Topology," Adv. Mater. 2000, 12, No. 24, Dec. 15, 2000, 1899-1908.

Lawrie et al, "Synthesis of Optically Complex Core-Shell Colloidal Suspensions: Pathways to Multiplexed. Biological Screening," Adv. Funct. Mater. 2003, 13, No. 11, Nov. 2003, 887-896.

Lopez-Quintela, "Synthesis of nanomaterials in microemulsions: formation mechanisms and growth control," Current Opinion in Colloid and Interface Science 8 (2003) 137-144.

Chang et al., "Preparation and Properties of Tailored Morphology Monodisperse Colloidal Silica-Cadmium Sulfide Nanocomposites," J. Am. Chem. Soc. 1994, 116, 6739-6744.

Santra et al., "Development of novel dye-doped silica nanoparticles for biomarker application," Journal of Biomedical Optics 6(2), 160-166, Apr. 2001.

Santra et al., "Conjugation of Biomolecules with Luminophore-doped Silica Nanoparticles for Photostable Biomarkers," Anal. Chem. 2001, 73, 4988-4993.

Bogush et al., "Preparation of Monodisperse Silica Particles Control of Size and Mass Fraction," Journal of Non-Crystalline Solids 104 (1988) 95-106.

Hall et al., "Cocondensation of Organosilica Hybrid Shells on Nanoparticle Templates: A Direct Synthetic Route of Functionalized Core-Shell Colloids," Langmuir 2000, 16, 1454-1456.

Sanjani et al., "Organic-Inorganic Nanocomposites with Core-shell Structure via Sol-gel Process," Materials Science Forum vols. 437-438 (2003) 419-422.

Goller at al., "Silica encapsulation of liquid PDMS droplets," Colloids and Surfaces A: Physicochemical and Engineering Aspects 142 (1998) 281-285.

Shchukin et al., "Magnetorheological photocatalytic systems," International Journal of Photoenergy, vol. 1, 1999, pp. 1-3.

Kim et al., "Fabrication of Inorganic and Hybrid Small Materials by Interface Selective Reactions," Polymeric Materials: Science and Engineering 2002, 87, 278.

Barbe et al., Silica Particles: A Novel Drug Delivery System, Adv. Mater. 2004, 16, No. 21, Nov. 4, 2004, 1959-1966.

Osseo-Asare,"2.2 Hydrolysis of Silicon Alkoxides in Microemulsions," Surfactance Sci. Ser. (2000) 92 (Fine Particles) 147-188, Silica.

Osseo-Asare, "18 Microemulsion-Mediated Synthesis of Nanosize Oxide Materials," Handbook of Microemulsion Science and Technology, 1999, 549-603.

Arriagada et al., "Controlled hydrolysis of tetraethoxysilane in a nonionic water-in-oil microemulsion: a statistical model of silica nucleation," Colloids and Surfaces A: Physiochemical and Engineering Aspects 154 (1999) 311-326.

Osseo-Asare et al., Growth Kinetics of Nanosize Silica in a Nonionic Water-in-Oil Microemulsion: A Reverse Micellar Pseudophase Reaction Model, Journal of Colloid and Interface Science 218, 68-76 (1999).

Esquena et al., "Study of low energy emulsification methods for the preparation of narrow size distribution w/o emulsion," Progr Colloid Polym Sci (1998) 110:235-239.

Esquena et al., "Preparation of monodisperse silica particles in emulsion media," Colloids and Surfaces A: Physicochemical and Engineering Aspects 123-124 (1997) 575-586.

Chang et al., "Controlled Formation of Silica Particles from Tetraethyl Orthosilicate in Nonionic Water-in-Oil Microemulsions," Langmuir 1997, 13, 3295-3307.

Esquena et al., "Preparation of Narrow Size Distribution Silica Particles Using Microemulsions," Langmuir 1997, 13, 6400-6406.

Lindberg et al., "Multivariate analysis of the size dependence of monodisperse silica particles prepared according to the sol-gel technique," Colloids and Surfaces A: Physicochemical and Engineering Aspects 123-124 (1997) 549-560.

Chang et al., "Kinetics of Silica Particle Formation in Nonionic w/o Microemulsions from TEOS," AIChE Journal vol. 42, No. 11, 1996, 3153-3163.

Lindberg et al., "Preparation of silica particles utilizing the sol-gel and the emulsion-gel processes," Colloids and Surfaces A: Physicochemical and Engineering Aspects 99 (1995) 79-88.

Osseo-Asare et al., "Preparation of $SiO_2$ Nanoparticles in a Non-Ionic Reverse Micellar System," Colloids and Surfaces, 50 (1990) 321-339.

Davies et al., "Engineered Particles Surfaces," Adv. Mater. 1998, 10, No. 15, 1624-1270.

Caruso, "Nanoengineering of Particle Surfaces," Adv. Mater. 13, No. 1, Jan. 5, 2011, 11-22.

Arici et al., "Core/shell nanomaterials in photovoltaics," International Journal of Photoenergy, vol. 5, 2003, 199-208.

Tago et al., "Novel Synthesis of Silica-Coated Ferrite Nanoparticles Prepared Using Water-in-Oil Microemulsion," J. Am. Ceram. Soc. 85(9) 2188-2194 (2002).

Santra et al., "Synthesis and Characterization of Silica-Coated Iron Oxide Nanoparticles in Microemulsion: The Effect of Nonionic Surfactants," Langmuir 2001 17, 2900-2906.

Yan et al., "Synthesis and Characterization of Silica-Embedded Iron Oxide Nanoparticles for Magnetic Resonance Imaging," Journal of Nanoscience and Nanotechnology, 2004, vol. 4, No. ½, 72-66.

Ryu et al., "Deposition of Titanic Nanoparticles on Spherical Silica," Journal of Sol-Gel Science and Technology 26, 489-493, 2003.

Shariq et al., "Photocatalytic degradation of aqueous pollutants using silica-modified $TiO_2$," Water Research 37 (2003) 3992-3996.

Fu et al., "Synthesis of titanic-coated silica nanoparticles using a nonionic water-in-oil microemulsion," Colloids and Surfaces A: Physicochemical and Engineering Aspects 179 (2001) 65-70.

Lawrie et al, "Synthesis of Optically Complex Core-Shell Colloidal Suspensions: Pathways to Multiplexed Biological Screening," Adv. Funct. Mater. 2003, 13, No. 11, Nov. 2003, 887-896.

Xiaoxiao et al., "Study on the effect of electrostatic on core-shell nanoparticles preparation with microemulsion technique," Chinese Science Bulletin vol. 50, No. 24, Dec. 2005, 2821-2826.

Duan et al., "A Study of Novel Organic Fluorescent Core-Shell Nanoparticle," Chemical Journal of Chinese Universities-Chinese 24 (2) 255-259, Feb. 20, 2003.

Duan et al., "Preparation of Organic Fluorescent Dye Doped Nanoparticle and Research of Encapsulated Mechanism," State Key Laboratory of Chemical and Biological Sensing and Chemometrics, College of Chemistry & Chemical Engineering Institute of Biological Technology, Hunan University, Changsha, 410082 (2002) 22(3), 14-20.

Zeng et al., "Synthesis and Characterization of New Silver-Silica Core-Shell Composite Nanoparticles," 2001 (3), 95-98.

(56) References Cited

OTHER PUBLICATIONS

"Nanoparticle probes for enhanced chemical and biological sensing," Nie, Shuming, 227$^{th}$ ACS National Meeting, Anaheim CA, United States, Mar. 28-Apr. 1, 2004, ANYL 221.

"Silica-Void Metal Composite Nanospheres for Nanoreactor and Nanocoating," Wei Wang, Abstracts of Papers 223$^{rd}$ ACS National Meeting, Orlando FL, United States, Apr. 7-11, 2002.

"Monodisperse core-shell colloidal spheres of zinc sulfide and silica for photonic applications," Krassimir P. Velikov et al., Abstracts of Papers, American Chemical Society (2001) 21$^{st}$ PHYS-295.

Chang et al., Creation of Templated Complex Topological Morphologies in Colloidal Silica, J. Am. Chem. Soc. 1994, 116, 6745-6747.

Boyle et al., "Synthesis of metal core ceramic shell nanoparticle," 227$^{th}$ ACS National Meeting Anaheim CA, United States, Mar. 28-Apr. 1, 2004.

Office Action, Australian patent application No. 2006212727 mailed Apr. 8, 2010.

Office Action, Australian patent application No. 2006212727 mailed Aug. 19, 2010.

* cited by examiner

*Hydrolysis*
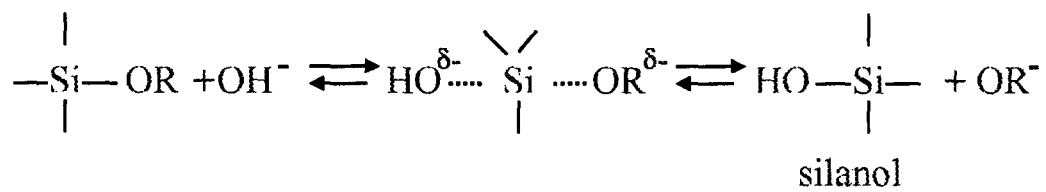
*Condensation*
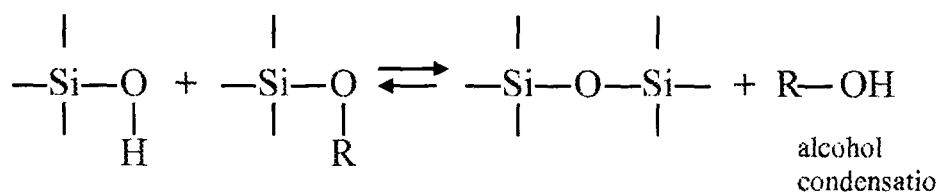
alcohol condensatio
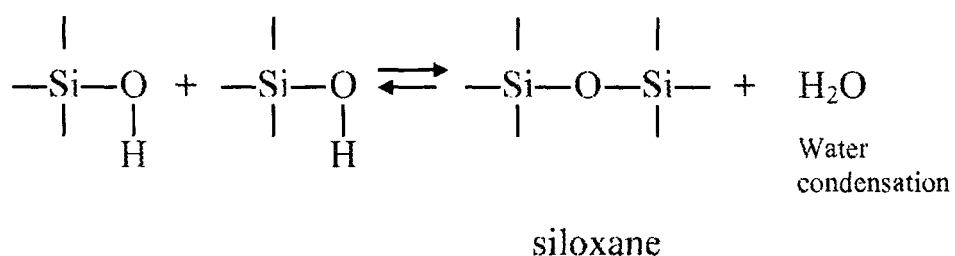
Water condensation
siloxane
FIG. 1

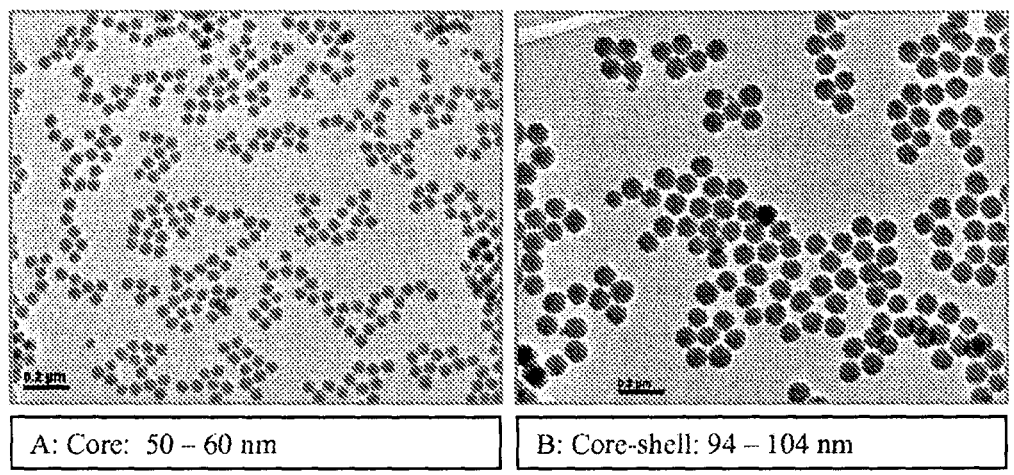
A: Core: 50 – 60 nm
FIG. 5A
B: Core-shell: 94 – 104 nm
FIG. 5B
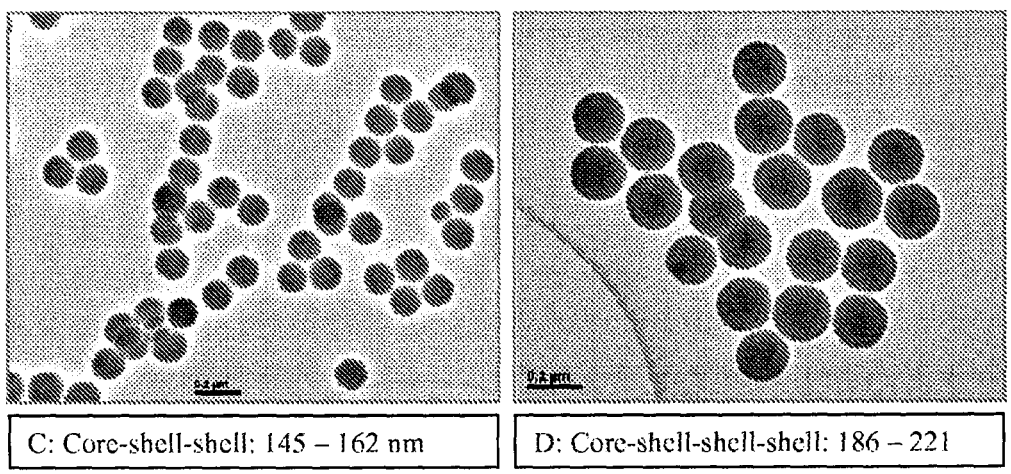
C: Core-shell-shell: 145 – 162 nm
FIG. 5C
D: Core-shell-shell-shell: 186 – 221
FIG. 5D

TMOS: 1.2 mmol
Particle size: ~ 22 nm

TMOS: 1.2 + 1.2 mmol
Particle size: ~ 27 nm

TMOS: 1.2 + 1.2 + 1.2 mmol
Particle size: ~ 31 nm

TMOS: 1.2 + 1.2 + 1.2 + 1.2 mmol
Particle size: ~ 33 nm

TMOS: 1.2 + 1.2 + 1.2 + 1.2 + 1.2 mmol
Particle size: ~ 36 nm

TEOS: 1.2 mmol
Particle size: ~50 nm

TEOS: 1.2 + 2.4 mmol
Particle size: 83-92 nm

TEOS: 1.2 + 2.4 + 3.6 mmol
Particle size: 91 – 106 nm

TEOS: 1.2 + 2.4 + 3.6 + 2.4 mmol
Particle size: 102 – 120 nm

TEOS: 1.2 + 2.4 + 3.6 + 2.4 + 3.6 mmol
Particle size: 108 – 129 nm

TEOS: 1.2 + 2.4 + 3.6 + 2.4 + 3.6 + 3.6 mmol
Particle size: 128 – 146 nm

LNK-759  LNK-760

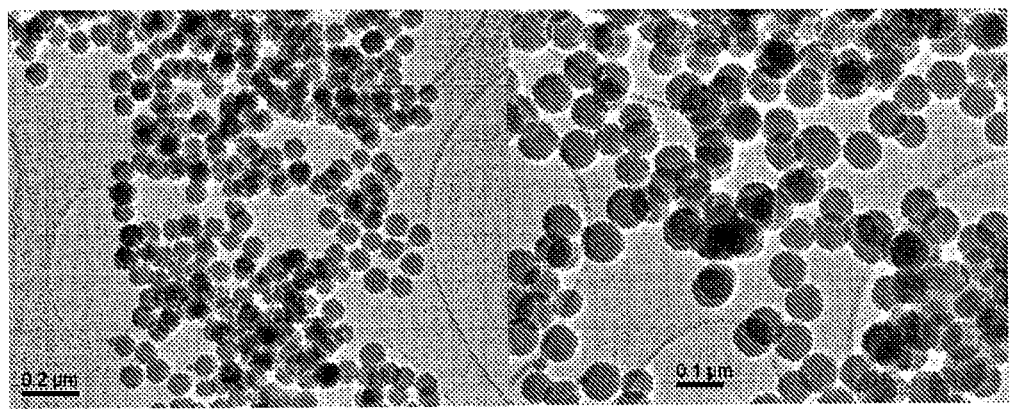
a (bar = 200 nm) FIG. 32A   b (bar = 100 nm) FIG. 32B
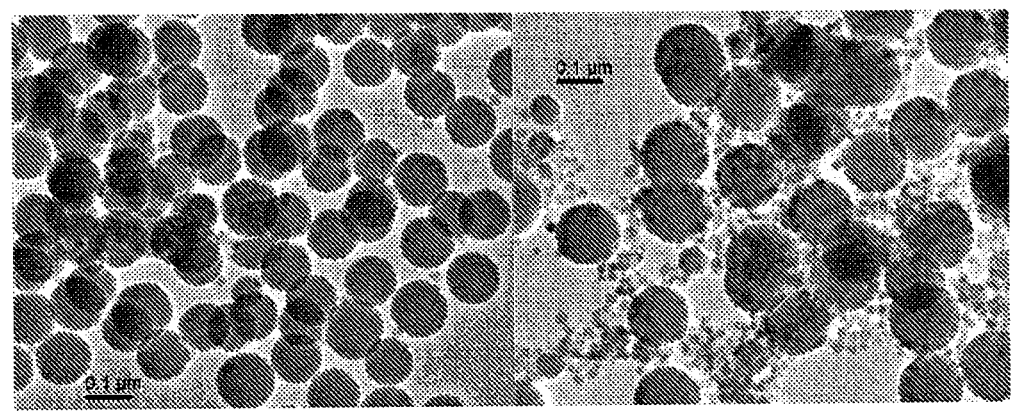
c (bar = 100 nm) FIG. 32C   d (bar = 100 nm) FIG. 32D
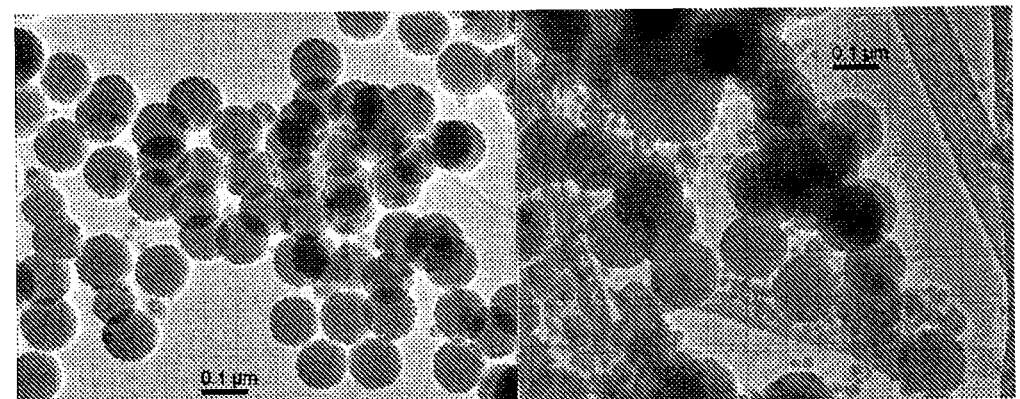
e (bar = 100 nm) FIG. 32E   f (bar = 100 nm) FIG. 32F

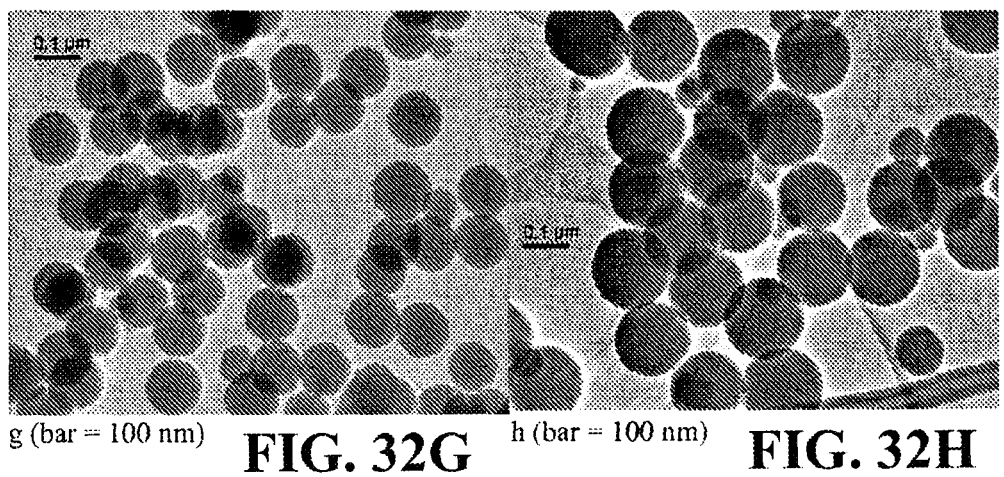
g (bar = 100 nm) FIG. 32G   h (bar = 100 nm) FIG. 32H

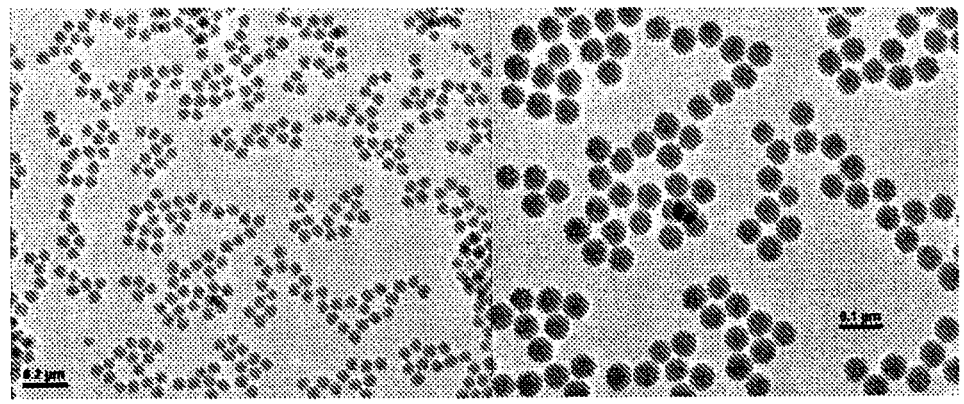
a: seed (bar=200 nm)　　　(bar=100 nm)　FIG. 34A
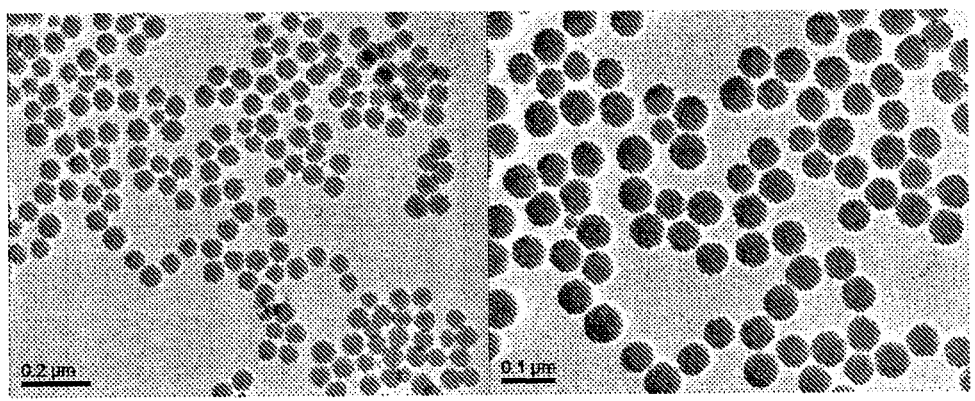
b: core+1-layer (bar=200 nm)　　(bar=100 nm)　FIG. 34B
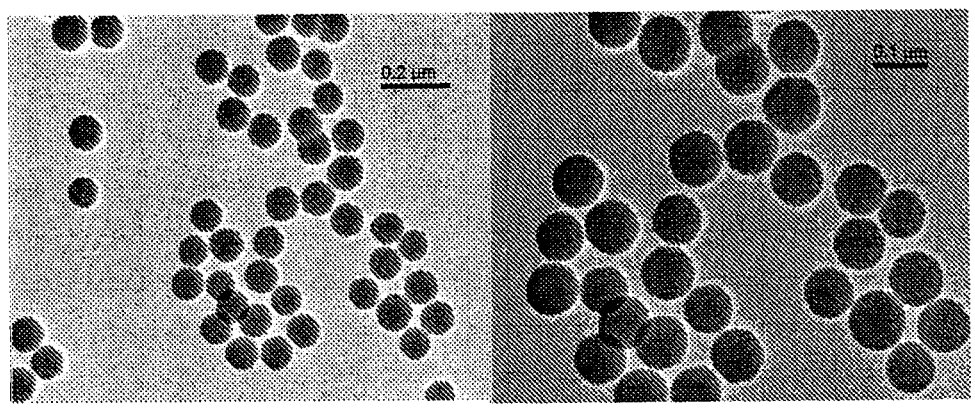
c: core+2-layers (bar=200 nm)　　(bar=100 nm)　FIG. 34C

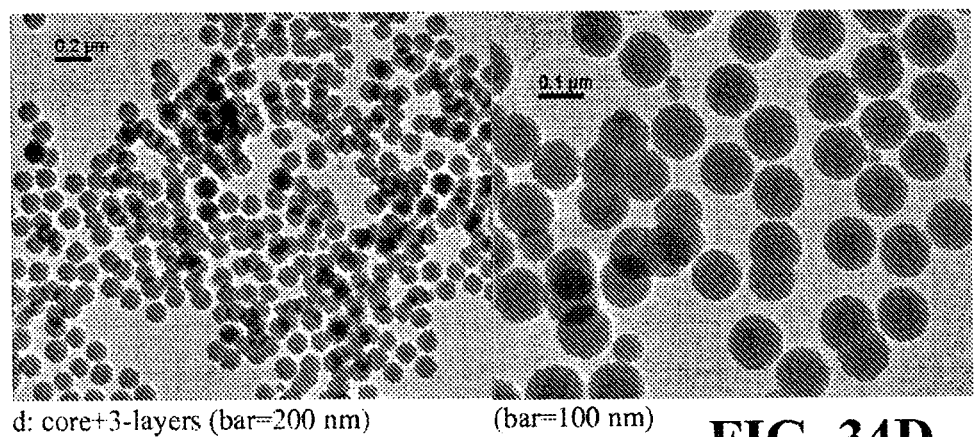
d: core+3-layers (bar=200 nm)     (bar=100 nm)    FIG. 34D
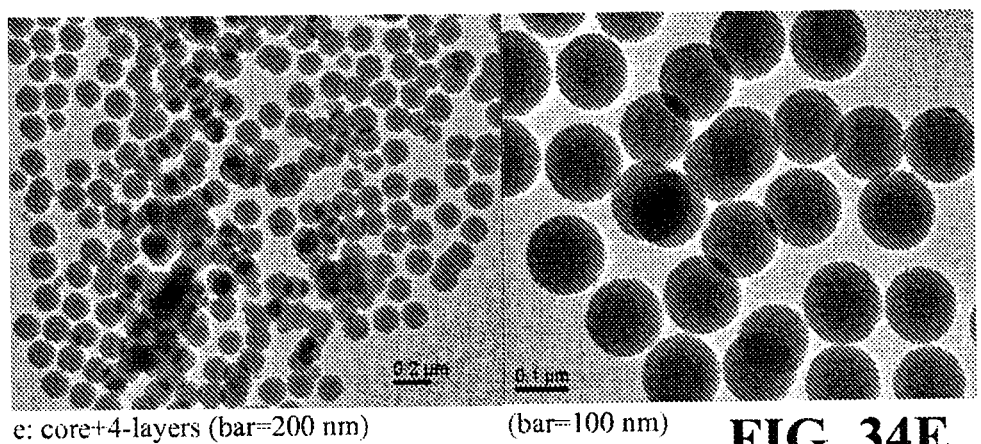
e: core+4-layers (bar=200 nm)     (bar=100 nm)    FIG. 34E
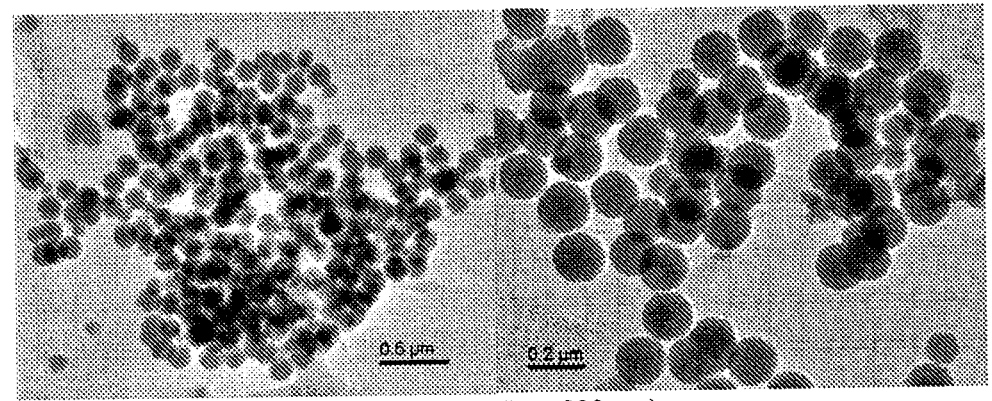
f: core+5-layers (bar=500 nm)     (bar=200 nm)    FIG. 34F

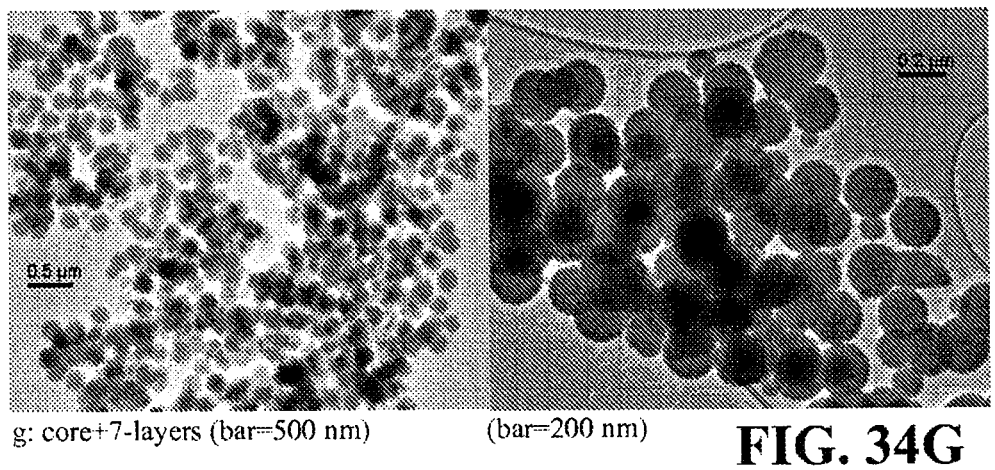
g: core+7-layers (bar=500 nm)　　(bar=200 nm)　FIG. 34G

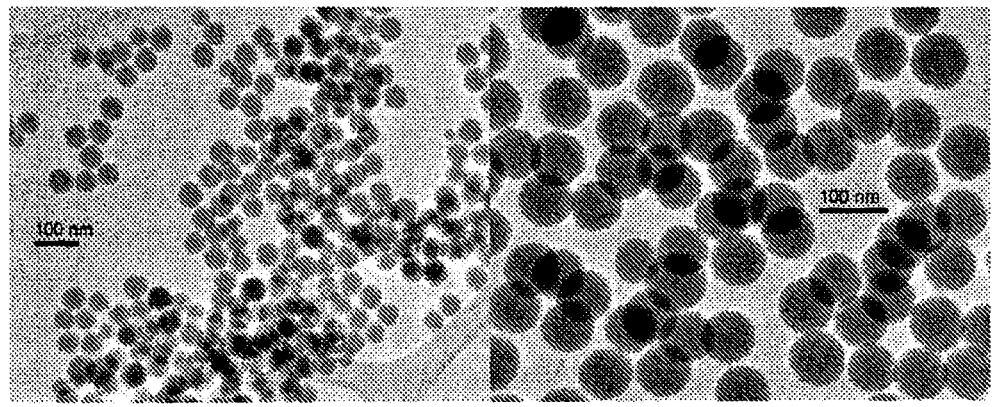
a: core (bar=100 nm) FIG. 35A
b: core+1-layer (bar=100 nm) FIG. 35B
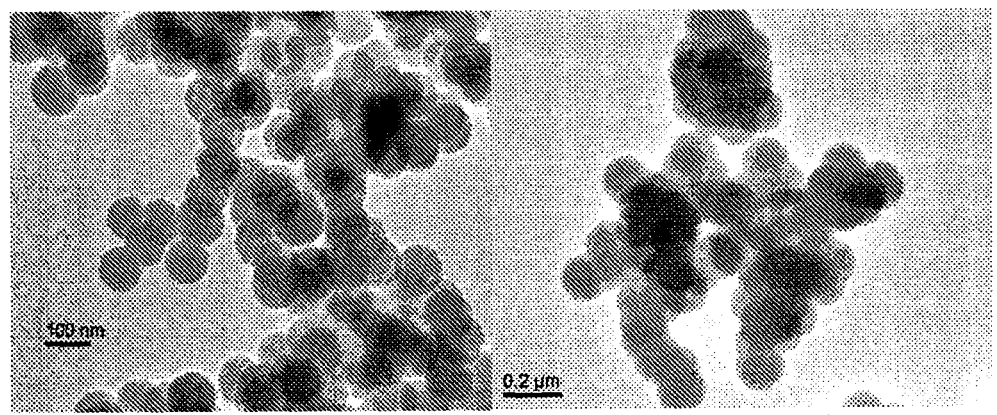
c: core+2-layer (bar=100 nm) FIG. 35C
d: core+3-layer (bar=200 nm) FIG. 35D
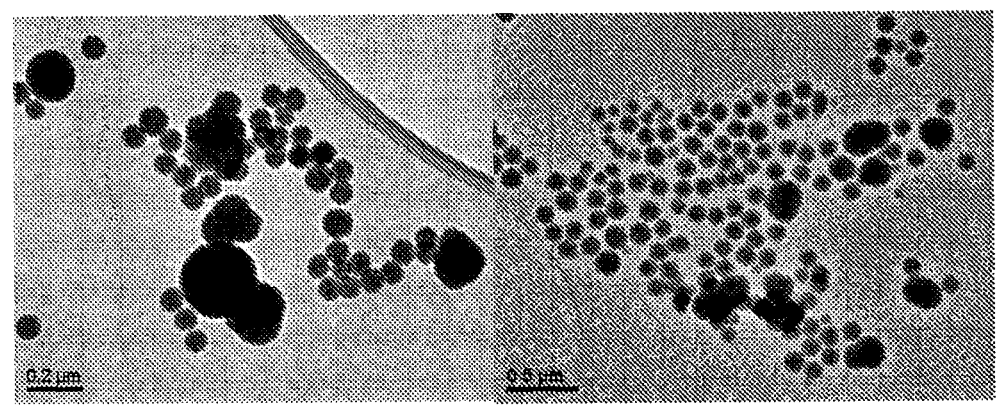
e: core+4-layer (bar=200 nm) FIG. 35E
f: core+5-layer (bar=500 nm) FIG. 35F

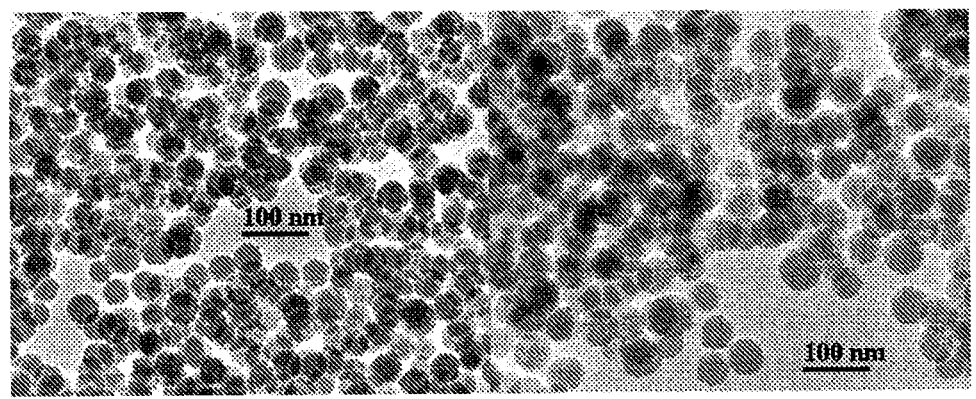
a (bar=100 nm) FIG. 36A   b (bar=100 nm) FIG. 36B
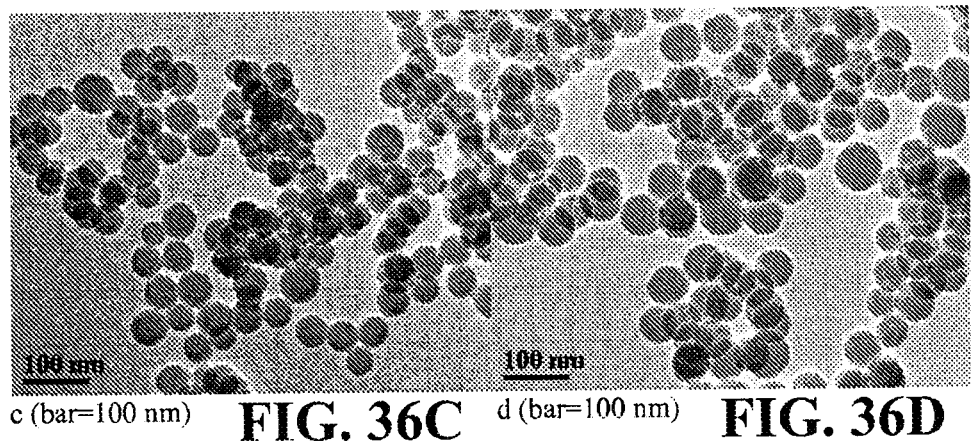
c (bar=100 nm) FIG. 36C   d (bar=100 nm) FIG. 36D

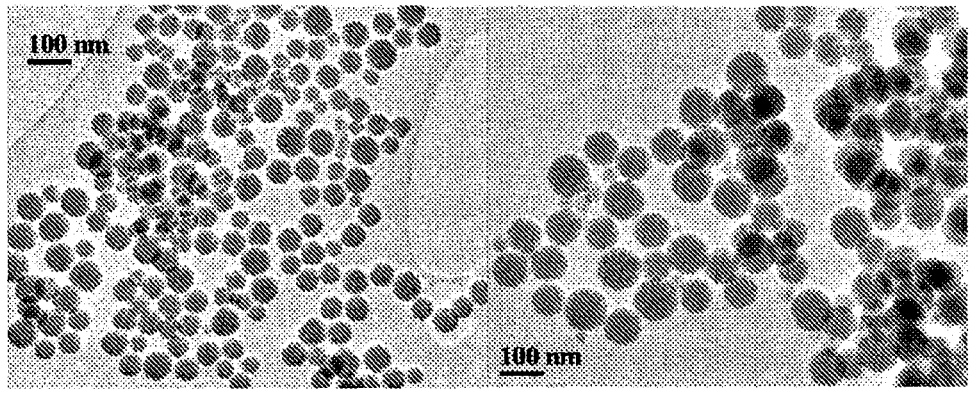
a (bar=100 nm) FIG. 37A  b (bar=100 nm) FIG. 37B
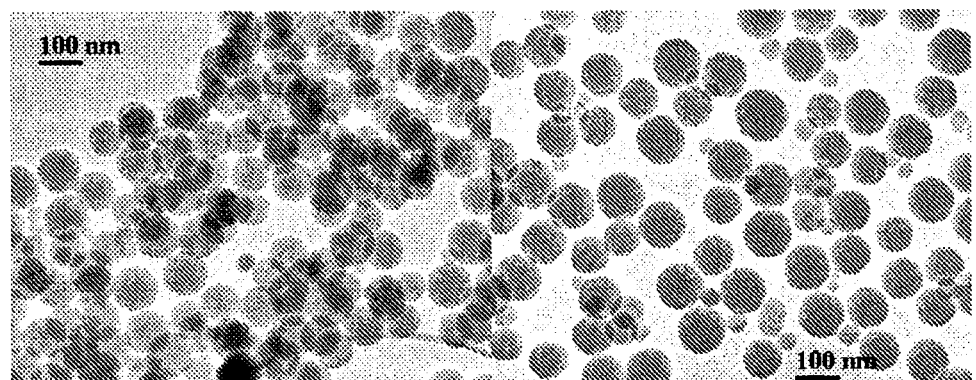
c (bar=100 nm) FIG. 37C  d (bar=100 nm) FIG. 37D
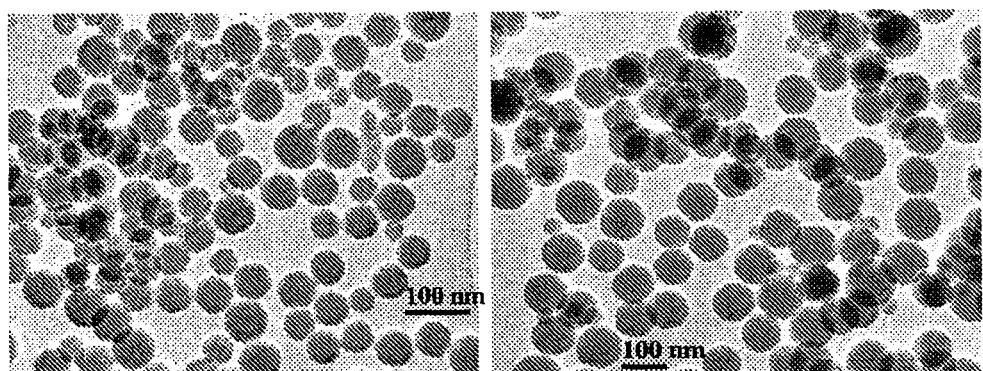
e (bar=100 nm) FIG. 37E  f (bar=100 nm) FIG. 37F

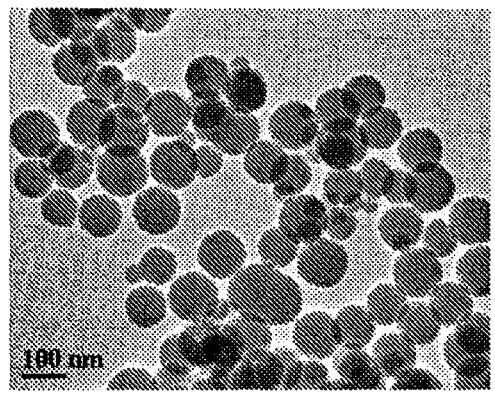
g (bar=100 nm) FIG. 37G a (bar=100 nm)

b (bar=100 nm)

c (bar=100 nm)

LAYERED NANOPARTICLES

This application is a divisional of U.S. application Ser. No. 11/816,052, which was filed on Oct. 23, 2007, which in turn is a national stage entry of International Application No. PCT/AU2006/000193, which was filed on Feb. 14, 2006, which in turn claims priority to Australian Application No. 2005900677, which was filed on Feb. 14, 2005, wherein the entireties of said patent applications are incorporated herein by reference.

TECHNICAL FIELD

The present invention relates to layered nanoparticles, and to processes for making them.

BACKGROUND OF THE INVENTION

It is generally believed that controlled drug delivery is capable of improving the safety and clinical efficacy of cancer chemotherapeutic drugs, which typically produce severe side effects due to non-specific toxicity. One approach to this problem is to preferentially deliver cytotoxic drugs to the tumour. It has been established by several research groups that nanospherical particles in the 50-250 nm diameter range, possessing the appropriate physico-chemical properties, can be selectively distributed into tumour masses from the general circulation, over a period of one to two days after intravenous injection. This occurs by virtue of the aberrant structure of the micro-vasculature within many tumours. Various types of nanoparticulate delivery systems have been used experimentally but most have significant limitations that have precluded their final use for medical applications.

The major limitations are as follows:
1) Their physical stability is too poor to provide long enough blood circulation to ensure accumulation into the tumour (e.g. liposomes),
2) The rate of release from most types of nano-particles is too fast to provide a concentrated dose to the tumour,
3) The stable nano-particles developed to date have very low drug loading and slow release rate which are insufficient to deliver the appropriate therapeutic dose,
4) Many types of nanoparticulate systems are rapidly detected by the immune system (i.e. reticulo-endothelial system) and eliminated from the blood stream, resulting in a small proportion of the drug reaching the tumour.

Most of the materials used as drug delivery vehicle are organic in nature: polymers, liposomes, dendrimers, etc. In contrast, the ceramic materials provide many advantages over the organic delivery matrices. For example silica particles are biologically inert and have hydrophilic surfaces. They are also non-toxic, highly biocompatible and can be synthesised at low temperature in order to preserve the molecular structure of the drug. Furthermore, their size and porosity remain stable within a wide range of chemical environment. Sol-gel technology, an inorganic room temperature polymerisation technique (see FIG. 1), has been used to successfully encapsulate organic molecules inside oxide matrices.

During the last several years, the present inventors have developed a technology for producing ceramic particles for controlled release applications (WO01/62332). This technology allows active molecules to be encapsulated in ceramic particles using a combination of sol-gel chemistry and water-in-oil (W/O) emulsion synthesis. The size of the particle is controlled by the size of the emulsion droplets and the release kinetics is controlled by the sol-gel chemistry. To produce monodisperse nanoparticles using this method, stable microemulsions are used. In such systems, the water droplet size is usually restricted to several to a few tens of nanometers limiting the final particle size to less than 100 nm even in the presence of important Ostwald ripening. Larger particle sizes can be obtained using unstable emulsion systems but the resulting particles present a broad size distribution which is undesirable in such application as for example the passive targeting of tumours where a precise control over the particle size is desirable. Although such a precise control over the size can be achieved using the Stöber process (seeded growth in diluted media), this type of process does not provide the compartmentalisation achieved in emulsions which is necessary to ensure encapsulation of the active materials during gelation. Thus the Stöber process is inadequate for the synthesis of particles for controlled release applications. Another limitation of the technology outlined in patent WO01/62332 is its inability to produce particles with delayed, sequential or pulsed release sequences. Once the ceramic particles are introduced in a liquid, they start to release immediately. This disadvantage might be overcome by producing a core-shell structure with the active molecule located in core surrounded by an empty shell which acts as a diffusion barrier and prevents the active to leach rapidly.

Substantial work has been performed during the last decade to try to achieve complex and tailored release pattern of active molecules from specific matrices. The delayed-release, timed-release, or sequential release of drug(s) from a variety of delivery vehicles have been investigated. To achieve these complex release patterns, the delivery system is either based on the modification of physico-chemical properties of the delivery materials or the modification of the morphology of the system such as using multi-layered structure. All these systems use an organic matrix in various forms: polymer gel, liposome, fibre, microcapsule, tablet etc. Particles, and more specifically nanoparticles, have not been investigated for these kinds of applications.

Core-shell colloidal materials with tailored structural, optical, and surface properties have been intensely investigated over the last decade. The research in this area was driven by the potential applications of such colloids in a wide range of fields. Most of the research effort has concentrated on changing the surface properties of a given particle by coating or encapsulating it within a shell of a different material. The core may be a metal oxide, a semiconductor, a quantum dot, a magnetic particle, a crystalline particles etc., while the shell usually changes the charge, the functionality, and the reactivity of the particle surface, and may also enhance the stability and dispersibility of the colloidal core. In other words, the material of core is different from shell materials, and the most commonly reported core-shell structures are ceramic core with polymer shell, or vice versa. Ceramic cores containing encapsulated actives and coated with a different kind of ceramic materials have also been reported in the literature.

Several methods have been reported in the literature to grow ceramic particles using sol-gel synthesis via W/O microemulsion. One such method depends on obtaining a larger particle size by adjusting the synthesis parameters. Although the particle size can be adjusted by controlling parameters such as the precursor concentration, water concentration, pH, temperature, ion strength, reaction time, there is a limitation on the particle growth. It is difficult using this method to produce monodisperse particles larger than 100 nm due to the intrinsic characteristics of the reverse micelles. Another method reported in the literature consist in extracting the particle seeds, drying them and then redispersing these seeds in a fresh W/O microemulsion, followed by the addition of more alkoxide precursors to grow the particles. There are two shortcomings regarding this method. First, during the extraction and drying steps the particles can aggregate irreversibly into micron size agglomerates, and second, the procedure introduces an additional separation step to recover the solid particles from liquid, which can significantly decrease the overall yield. Yet another process that can be used to increase particle size is described in FIG. 2. However, in this case the active molecules can only be encapsulated in the core. In addition the particles growth is limited by the fact that the alkoxide precursor needs to consume water for reaction. Since the amount of water is dictated by the formation of W/O microemulsion, only a limited supply of water is available. In fact, not all of the water introduced in the system is available for sol-gel reaction, as some water is bonded to the surfactant. As more alkoxide is being added more water is being consumed and less is available for further hydrolysis and growth.

There is therefore a need for a layered nanoparticle in which a dopant is located in, and restricted to, the core of the nanoparticle and/or one or more of the layers surrounding the core, and for a process for making such a nanoparticle. There is also a need for a process capable of making core-shell ceramic nanoparticles with more than one encapsulated molecular species (dopant) or with the active (dopant) encapsulated in different discrete locations or layers (i.e. shells). Such a process may open up a wide range of novel potential applications such as optical storage, data encryption or security ink in addition to the controlled release of drugs described above.

OBJECT OF THE INVENTION

It is an object of the present invention to overcome or substantially ameliorate at least one of the above disadvantages. It is a further object to at least partially satisfy at least one of the above needs.

SUMMARY OF THE INVENTION

In a broad form of the invention there is provided a process for forming a layered nanoparticle, comprising exposing a catalyst to a reagent in the presence of a core particle, whereby the reagent reacts to form a layer on the core particle to form the layered nanoparticle. The catalyst, reagent and core particle may be disposed in a fluid. The fluid may be a liquid. The catalyst may be located on and/or in and/or around the core particle. The catalyst may be a catalyst for reaction of the reagent. The catalyst may be located on the surface of the particle. The reaction may comprise one or more of hydrolysis, condensation, polycondensation, crosslinking, polymerisation, precipitation and gelation. There may be a dopant surrounding the core particle, and the reaction of the reagent may encapsulate the dopant in the layer. The core particle may form the core of the layered nanoparticle. Thus the layered nanoparticle, once formed, may comprise the core particle at least partially surrounded or encapsulated by the layer. The core particle may be completely surrounded or encapsulated by the layer. The core particle may be a single particle or an agglomerate of two or more particles. The core particle may comprise the same material as the layer or it may comprise a different material.

In one form the present invention provides a process for forming a layered nanoparticle, comprising:
  providing a suspension comprising a core particle in a first liquid; and
  exposing a catalyst to a reagent in the presence of the core particle,
whereby the reagent reacts to form a layer on the core particle to form the layered nanoparticle.

The step of providing the core particle in the liquid may comprise forming the core particle in the first liquid. In an embodiment, the particle is not separated from the first liquid before the step of exposing. The first liquid may be non-polar.

The step of exposing may be repeated one or more times, thereby forming a plurality of layers. The step of exposing may comprise the steps of:
  adding a second liquid to the suspension, said second liquid comprising the catalyst; and
  adding the reagent, or a precursor for the reagent, to the suspension;
whereby, if the reagent is added to the suspension, the reagent reacts to form a layer on the core particle, and if a precursor for the reagent is added to the suspension, the precursor is converted to the reagent, and the reagent to reacts to form a layer on the core particle. The catalyst may be dissolved in the second liquid. The second liquid may be immiscible with the first liquid. The catalyst may be a catalyst for conversion of the precursor to the reagent and/or for formation of the layer from the reagent.

In another form the present invention provides a process for making a layered nanoparticle comprising:
  providing a suspension comprising a core particle in a first liquid;
  adding a second liquid to the suspension, said second liquid comprising a catalyst for reaction of a reagent; and
  adding the reagent, or a precursor for the reagent, to the suspension so as to cause the reagent to react to form a layer on the core particle.

In another form the present invention provides a process for forming a layered nanoparticle, comprising:
  providing a suspension comprising a core particle in a first liquid;
  adding a second liquid to the suspension, said second liquid being immiscible with the first liquid; and
  adding a reagent, or a precursor for the reagent, to the suspension comprising the second liquid;
whereby, if the reagent is added to the suspension comprising the second liquid, the reagent reacts to form a layer on the core particle, and if a precursor for the reagent is added to the suspension comprising the second liquid, the precursor is converted to the reagent, and the reagent thus formed reacts to form a layer on the core particle, to form the layered nanoparticle. The second liquid may comprise a catalyst. If the second liquid does not comprise a catalyst, the reagent may be such as to be capable of forming the layer without a catalyst, and/or the precursor may be capable of forming the reagent without a catalyst. For example, if the second liquid is aqueous, the precursor may be a silane that hydrolyses in the absence of a catalyst.

In another form, the process comprises:
  providing a suspension comprising a core particle in a first liquid;
  adding a second liquid to the suspension, said second liquid comprising a catalyst for reaction of a reagent; and
  adding a precursor for the reagent to the suspension so as to cause the precursor to be converted to the reagent, and so as to cause the reagent to react to form a layer on the core particle.

The second liquid may be immiscible with the first liquid. The step of adding the second liquid may comprise depositing the second liquid on the core particle, for example on the surface of the core particle. If a precursor is added to the suspension, the precursor may be capable of reacting with the second liquid to form the reagent, i.e. it may be a precursor for the reagent. The reagent may be a condensable species, a crosslinkable species or a polymerisable species. The reaction of the reagent may form a solid layer or a gel layer on the core particle, and may comprise condensation, crosslinking and/or polymerisation of the reagent. The core particle may be a nanoparticle and may be between about 5 and 150 nm in diameter, or may be a submicron particle, and may be less than about 500 nm in diameter. The core particle and/or the layer may be solid, and may be porous, for example microporous and/or mesoporous. The second liquid may comprise a dopant, whereby the formation of the layer encapsulates the dopant in the layer. The step of adding the second liquid and adding the reagent may be repeated one or more times, thereby forming a plurality of layers. The core particle and each layer independently may or may not have a dopant, and the dopants, if present, may be the same or different. The or each dopant may be a releasable substance, and may be releasable from the nanoparticle. The process may generate a nanoparticulate substance comprising a plurality of layered nanoparticles, whereby the step of providing a suspension comprises providing a suspension comprising a plurality of core particles in the first liquid. The core particles, and independently the layered nanoparticles of the nanoparticulate substance, may be homogeneous in shape or may be heterogeneous in shape. They may be monodispersed, or may have a narrow particle size distribution, or they may have a broad particle size distribution.

In one aspect of the invention there is provided a process for making a layered nanoparticle comprising:
  a) providing a suspension comprising a core particle, a first surfactant and optionally a first cosurfactant in a first non-polar liquid;
  b) adding an aqueous liquid to the suspension, said aqueous liquid comprising a catalyst for condensation of a condensable species and optionally also comprising a dopant or a combination of dopants;
  c) adding a second non-polar liquid, a second surfactant and optionally a second co-surfactant, said second non-polar liquid being miscible with the first non-polar liquid; and
  d) providing the condensable species (the reagent) to the suspension such that the condensable species condenses in the presence of the catalyst to form a layer at least partly surrounding the core particle to generate the layered nanoparticle.

The second non-polar liquid may be the same as or different to the first non-polar liquid. The second surfactant may be the same as or different to the first surfactant. The second co-surfactant may be the same as or different to the first co-surfactant. The second non-polar liquid, second surfactant and second co-surfactant may be added such that the ratios of first non-polar liquid plus second non-polar liquid to first surfactant plus second surfactant and to first co-surfactant plus second co-surfactant remain constant on a v/v. v/w, w/w, v/mol or w/mol basis. The suspension may be provided at a temperature of between about 1 and 70° C., or the process may comprise bringing the suspension to a temperature between about 1 and 70° C., commonly between about 15 and 40° C., and more commonly between 20 and 30° C., i.e. ambient temperature. Lower temperatures may be used provided that the temperature is such that neither the dispersed phase nor the continuous phase freezes. Higher temperatures may at times be used, depending on the volatility and boiling point of the two phases and the inversion temperature of the surfactant. Step d) may comprise providing a hydrolysable species to the suspension to form the layered nanoparticle, said hydrolysable species being capable of hydrolysing in the aqueous liquid to form the condensable species. Step d) may comprise the steps of hydrolyzing the hydrolysable species in the aqueous liquid and of condensing the condensable species in the aqueous liquid to form the layer. The process may comprise the step of maintaining the suspension at a sufficient temperature (for example between about 1 and 70° C.) for a sufficient time (for example between about 6 and 96 hours) to hydrolyse the hydrolysable species, and optionally also to condense the condensable species. Steps b) to d) may be repeated at least once, or may be repeated 2, 3, 4, 5, 6, 7, 8, 9, 10 or more than 10 times. In each repetition, the aqueous liquid may comprise a dopant or a combination of dopants, or may comprise no dopant, and the dopant in any repetition, if present, may be the same as or different to the dopant in any other repetition. Each repetition may form a layer, and each layer may comprise a dopant, or may comprise no dopant. The or each dopant may be a releasable substance, or may be a non-releasable substance. The core particle may be between about 5 and 150 nm in diameter or may be less than 500 nm in diameter. The or each layer may have a mean thickness between about 1 and 100 nm, or between about 1 and 50 nm, 5 and 75 nm or 5 and 30 nm. The process may be capable of controlling the thickness of the or each layer. The core particle may be porous, and may be microporous and/or may be mesoporous and may have a pore size between about 0.5 and 20 nm. The core particle may comprise a dopant, which may be the same as or different to the dopant in the layer, or in any or all of the layers. The hydrolysable species in any repetition may be the same as or different to the hydrolysable species in any other repetition. One or both of the suspension and the aqueous liquid may comprise a surfactant. The process may generate a nanoparticulate substance comprising a plurality of layered nanoparticles, whereby the step of providing a suspension comprises providing a suspension comprising a plurality of core particles in the first non-polar liquid.

The process may additionally comprise one or more of the following steps:
  e) at least partially separating the layered nanoparticle, or nanoparticulate substance, from the first non-polar liquid;
  f) washing the layered nanoparticle, or nanoparticulate substance, with an aqueous liquid;
  g) washing the layered nanoparticle, or nanoparticulate substance, with an organic liquid;
  h) drying the layered nanoparticle, or nanoparticulate substance.

Step f) may be conducted at room temperature, or may be conducted as high as 80° C. (e.g. at about 20, 30, 40, 50, 60, 70 or 80° C.). The organic liquid of step g) may be polar or non-polar. Its polarity may be selected depending on the solubility of dopants in the organic liquid. Step g) may be conducted at room temperature, or may be conducted as high as 70° C. (e.g. at about 20, 30, 40, 50, 60 or 70° C.), but should be conducted at or below the boiling point of the organic liquid. Steps f and g may be conducted more than once, and may be conducted in any order, or one or both may be omitted. For example, the process may comprise (in that order) steps e and h, or steps e, f and h, or steps e, g and h, or steps e, f, g and h, or steps e, g, f and h, or steps e, g, f, g and h, or may comprise some other order of steps. Step h may be conducted in a manner that prevents or inhibits aggregation, for example step h may comprise freeze drying as described in W01/62332 (Barbé and Bartlett, "Controlled Release Ceramic Particles, Compositions thereof, Processes of Preparation and Methods of Use"). Step h may be performed directly after step e. In that case, the large amount of surfactant present at that stage may prevent physical contact between the particles and thus inhibit aggregation.

In an embodiment there is provided a process for making a layered nanoparticle having a dopant therein or thereon, comprising:
- a) providing a stable suspension comprising a core particle, a surfactant and optionally a cosurfactant in a non-polar liquid;
- b) adding an aqueous liquid to the suspension, said aqueous liquid comprising the dopant and a catalyst for condensation of a condensable species;
- c) adding a second non-polar liquid, a second surfactant and optionally a second co-surfactant; and
- d) adding a hydrolysable species to the suspension to form the layered nanoparticle having the dopant therein or thereon, said hydrolysable species being capable of hydrolysing in the aqueous liquid to form the condensable species.

One or both of the suspension and the aqueous liquid may comprise a surfactant. The surfactant may be dissolved in the aqueous liquid or in the suspension or in both.

In another embodiment the process comprises:
- a) providing an emulsion comprising aqueous droplets dispersed in a non-polar liquid, said emulsion additionally comprising a surfactant and optionally a co-surfactant, wherein the droplets comprise a catalyst for condensation of a first condensable species upon hydrolysis;
- b) adding a first hydrolysable species to the emulsion, said first hydrolysable species being capable of hydrolyzing in the aqueous droplets to form the first condensable species, thereby forming a suspension of core particles in the non-polar liquid;
- c) adding an aqueous liquid to the suspension, said aqueous liquid comprising a catalyst for condensation of a second condensable species;
- d) adding a solution of a second surfactant, and optionally a second cosurfactant, to the suspension; and
- e) adding a second hydrolysable species to the suspension, said second hydrolysable species being capable of hydrolysing in the aqueous liquid to form the second condensable species.

The emulsion may be a water-in-oil (W/O) emulsion. Following the addition of the first hydrolysable species (step b) or the second hydrolysable species (step e), the hydrolysable species may hydrolyse to form the first or second condensable species respectively, which may then condense due to the action of the catalyst(s) to form a layer at least partially surrounding the core particles. The first hydrolysable species and the second hydrolysable species may be the same or they may be different. Steps c) to e) may be repeated at least once, or may be repeated 2, 3, 4, 5, 6, 7, 8, 9, 10 or more than 10 times, whereby each repetition forms a layer at least partially surrounding the core particles. In each repetition, the aqueous liquid may comprise a dopant or may comprise no dopant, and the dopant in any repetition may be the same as or different to the dopant in any other repetition. The emulsion and/or the aqueous liquid may comprise a dopant, and at least one region selected from the group consisting of the core particles and the layer(s) may comprises at least one dopant.

In another embodiment there is provided a process for making layered nanoparticles comprising:
- a) providing a surfactant solution comprising a surfactant and a non-polar liquid, and optionally a co-surfactant;
- b) adding to the surfactant solution an aqueous solution comprising a catalyst for condensation of a first condensable species and, optionally, also comprising a first dopant (core dopant);
- c) forming an emulsion from the surfactant solution and the aqueous solution;
- d) adding a first hydrolysable species to the emulsion, said first hydrolysable species being capable of hydrolysing in the aqueous solution to form the first condensable species;
- e) maintaining the emulsion at a sufficient temperature for sufficient time for formation of a suspension of core particles from the first hydrolysable species;
- f) adding an aqueous liquid to the suspension, said aqueous liquid comprising a catalyst for condensation of a second condensable species, and optionally a second dopant (layer dopant);
- g) adding a solution of a second surfactant, and optionally a second cosurfactant, to the suspension; and
- h) adding a second hydrolysable species to the suspension to form the layered nanoparticles, wherein the second hydrolysable species is capable hydrolysing in the aqueous liquid to form the second condensable species.

Following the addition of the first hydrolysable species or the second hydrolysable species, the hydrolysable species may hydrolyse to form the first or second condensable species respectively, which may then condense due to the action of the catalyst(s).

The emulsion may be a microemulsion.

In another embodiment there is provided a process for making layered nanoparticles comprising:
- a) providing a surfactant solution comprising a surfactant and a non-polar liquid, and optionally a co-surfactant;
- b) adding to the surfactant solution an aqueous solution comprising a catalyst for condensation of a first condensable species and, optionally, also comprising a first dopant;
- c) forming an emulsion from the surfactant solution and the aqueous solution;
- d) adding a first hydrolysable species to the emulsion, said first hydrolysable species being capable of hydrolysing in the aqueous solution to form the first condensable species;
- e) maintaining the emulsion at a sufficient temperature for sufficient time for formation of a suspension of core particles from the first hydrolysable species;
- f) adding an aqueous liquid to the suspension, said aqueous liquid comprising a catalyst for condensation of a second condensable species, and optionally a second dopant;
- g) adding a solution of a second surfactant, and optionally a second cosurfactant, to the suspension;
- h) adding a second hydrolysable species to the suspension to form layered nanoparticles, wherein the second hydrolysable species is capable hydrolysing in the aqueous liquid to form the second condensable species;
- i) at least partially separating the layered nanoparticles from the non-polar liquid;
- j) washing the layered nanoparticles with an organic liquid;
- k) washing the layered nanoparticles with an aqueous liquid;
- l) washing the layered nanoparticles with an organic liquid (which may be the same as or different to the organic liquid of step j; and
- m) drying the layered nanoparticles.

In another aspect of the invention there is provided a layered nanoparticle comprising a core particle (i.e. core) and one or more layers at least partially surrounding said core particle. The layered nanoparticle may be spherical. The core particle may be a solid, and may be a porous solid, for example a microporous or mesoporous solid, and may be spherical or non-spherical. The mean diameter of the core may be between about 5 and 500 nm. The or each layer may, independently, be a solid layer or a gel layer. At least one region of the layered nanoparticle selected from the group consisting of the core and the one or more layers may comprise a dopant, or a plurality (for example 2, 3, 4, 5 or more than 5) of dopants. Thus there may be a core dopant and/or one or more layer dopants. The or each dopant may be substantially homogeneously distributed in the region that comprises said dopant. Thus for example, if the nanoparticle comprises a core and a single layer, and the core comprises a core dopant and the layer comprises a layer dopant, then the core dopant may be substantially homogeneously distributed in the core, and the layer dopant may be substantially homogeneously distributed in the layer. The layered nanoparticle may be a microporous or mesoporous ceramic nanoparticle. The core and the one or more layers may each, independently, be microporous or mesoporous. The or each layer, and optionally the core particle, may, independently, comprise a hydrolysed silane, for example a hydrolysed alkoxysilane, and may comprise silica and/or a polysilsesquioxane. The or each layer, and optionally the core particle, may, independently, comprise a ceramic or an oxide, e.g. a metal oxide. If more than one of the core and the one or more layers comprises a dopant, then the dopants in each of these may be the same or they may be different. The or each dopant may independently be releasable or non-releasable. The layered nanoparticle may be capable of sequential release and/or delayed release of one or more of the releasable dopants. The layered nanoparticle may have a mean diameter between about 10 and 500 nm. The core and the or each layer may, independently, be microporous or mesoporous, and may have pores between about 0.5 and 10 nm. The or each layer may, independently, have a mean thickness between about 1 and 50 nm. The dopant may be an inorganic substance or an organic substance. It may be a salt, or a dye, a catalyst, an active material or active substance, e.g. a biologically active substance (for example a protein, polysaccharide, enzyme, drug, peptide etc.), a magnetic substance, a radioactive species, a radioactive tracer or some other type of dopant.

In one embodiment there is provided a layered nanoparticle comprising a porous core particle comprising a first dopant and a porous layer comprising a second dopant at least partially surrounding said core particle. At least one of the first and second dopants may be releasable from the layered nanoparticle. Thus the nanoparticle may comprise a porous core particle comprising a first releasable dopant and a porous layer comprising a second releasable dopant at least partially surrounding said core particle. The nanoparticle may be capable of releasing the second releasable dopant and the first releasable dopant sequentially.

In another embodiment there is provided a layered nanoparticle comprising a porous core particle comprising a first releasable dopant, a first porous layer surrounding the core particle, said first layer comprising no releasable dopant, and a second porous layer comprising a second releasable dopant at least partially surrounding the first porous layer. The nanoparticle may be capable of releasing the second releasable dopant and the first releasable dopant sequentially, with a delay between release of the second and first dopants. The length of the delay may be dependent on the thickness and porosity of the first layer.

In another embodiment there is provided a layered nanoparticle comprising a core particle comprising no releasable dopant and a porous layer comprising a releasable dopant at least partially surrounding said core particle. The core particle may comprise a non-releasable dopant, for example a non-releasable pigment for colouring the nanoparticle. The core may be porous or non-porous. The core may comprise a magnetic material, so that the layered nanoparticle is magnetic.

In another embodiment there is provided a layered nanoparticle comprising a non-porous core particle comprising, optionally consisting of, a releasable dopant and a porous layer comprising no releasable dopant, said porous layer at least partially surrounding the core particle. The nanoparticle may be capable of releasing the dopant after a delay. The length of the delay may be dependent on the thickness and porosity of the porous layer. The layer may have a non-releasable dopant, for example a non-releasable pigment for colouring the nanoparticle.

There is also provided a nanoparticulate substance comprising a plurality of layered nanoparticles according to the invention. The nanoparticulate substance may be monodispersed, or may have a narrow particle size distribution.

There is also provided a layered nanoparticle when made by the process of the invention. Also there is provided a nanoparticulate substance comprising a plurality of layered nanoparticles according to the invention or when made by the process of the invention.

In another aspect of the invention there is provided a method for delivering a releasable substance to a fluid comprising exposing a layered nanoparticle according to the invention, or a plurality of layered nanoparticles according to the invention, to the fluid, wherein the layered nanoparticle(s) has a releasable substance therein and/or thereon (e.g. in at least one of the layers or the core particle), and the fluid is capable of at least partially releasing the releasable substance from the layered nanoparticle(s).

The fluid may be an aqueous fluid, for example a biological fluid, or may be a non-aqueous fluid, for example an organic solvent. The exposing may comprise stirring, shaking, swirling, sonicating or otherwise agitating the layered nanoparticle(s) with the fluid. The method may comprise releasing the releasable substance into the fluid, and may comprise releasing the releasable substance in a controlled manner. The release of the releasable substance may be controlled variable release, whereby the rate of release of the releasable substance is variable with time in a controlled and/or predetermined manner.

In an embodiment the releasable substance is a drug, and the fluid is a bodily fluid e.g. blood in a patient. This embodiment comprises a method for administering the drug to the patient, said method comprising delivering to the patient, e.g. to the blood of the patient, a layered nanoparticle according to the invention, or a plurality of layered nanoparticles according to the invention, said layered nanoparticle(s) having the drug therein and/or thereon. The drug may be for example an anticancer drug. The layered nanoparticle(s) may have a diameter between about 10 and 500 nm, or between about 50 and 300 nm. The delivery may be intravenous (IV) delivery, and may comprise injecting into the patient a suspension comprising the nanoparticle(s). The suspension may comprise a suspending fluid. Suitable suspending fluids for injections are well known, and may comprise saline, Ringer's solution, glucose solution, fructose solution, dextrose solution, amino acid solution, protein hydrolysate, sodium lactate solution or some other aqueous liquid. There is also provided the use of a layered nanoparticle according to the invention for administering a drug to a patient, said layered nanoparticle having the drug therein and/or thereon.

In another aspect of the invention there is provided a layered nanoparticle according to the invention, or a plurality of layered nanoparticles according to the invention, when used for delivering a releasable substance to a fluid.

The invention also provides for use of a layered nanoparticle according to the invention for selective sorption of at least one component of a mixture. The invention further provides for a layered nanoparticle when used for selective sorption of at least one component of a mixture.

BRIEF DESCRIPTION OF THE DRAWINGS

A preferred form of the present invention will now be described by way of example with reference to the accompanying drawings wherein:

FIG. 1 shows a sol-gel reaction sequence in the presence of base;

FIG. 5 shows TEM images of uniform silica particles with a core-shell structure;

FIG. 7-$b$ shows a TEM micrograph of silica particles produced in the microemulsion system b) NP-9/1-pentanol/cyclohexane/NH4OH/TMOS:

FIG. 7-$c$ shows a TEM micrograph of silica particles produced in the microemulsion system c) Triton X-100/toluene/NH4OH/TMOS:

FIG. 11-$b$ shows a TEM micrograph of core-shell structure having: b) a dark field image (bright areas indicate heavier elements);

FIG. 15-$b$ shows TEM micrographs of particles grown using different dilution ratios, where the dilution rates (volume of fresh emulsion/volume of seed emulsion) were: A) 2, B) 3, C) 4, D) 5 for sample 2, silica core copper doped, the extra added aqueous phase 1.333 mol/L NH4OH without copper;

FIG. 23-$b$ shows photographs of samples with composition listed in Table 4 that is b) suspended in Milli-Q water;

FIG. 27-$b$ shows a release rate curve of b) Sample LNK-824 (0.6055 g of freeze-dried powder in 20 mL SBF at 37° C., max=450 nm), wherein the freeze dried powders contain 15 wt % of SiO2 and 85 wt % of NaCl;

FIG. 28$b$ shows a diagrammatic representation of an embodiment of layered nanoparticles according to the present invention;

FIG. 28$c$ shows a diagrammatic representation of an embodiment of layered nanoparticles according to the present invention;

FIG. 28$d$ shows a diagrammatic representation of an embodiment of layered nanoparticles according to the present invention;

FIG. 28$e$ shows a diagrammatic representation of an embodiment of layered nanoparticles according to the present invention;

FIG. 28$f$ shows a diagrammatic representation of an embodiment of layered nanoparticles according to the present invention;

FIG. 32 shows TEM images of silica particles at various surfactant concentrations: (a, b) seed particles made by 0.2 mol/L NP-9 and 0.2 mol/L 1-pentanol, 74-86 nm; (c) core+2-layers particles by 0.4 mol/L NP-9 without 1-pentanol, 109-123 nm; (d) core+3-layers particles by 0.4 mol/L NP-9 without 1-pentanol, 132-152+20 nm; (e) core+2-layers particles by 0.6 mol/L NP-9 without 1-pentanol, 106-126 nm; (f) core+3-layers particles by 0.6 mol/L NP-9 without 1-pentanol, 132-145+20 nm; (g) core+2-layers particles by 0.4 mol/L NP-9, 0.4 mol/L 1-pentanol, 100-131 nm; (h) core+3-layers particles by 0.4 mol/L NP-9, 0.4 mol/L 1-pentanol, 128-179 nm;

FIG. 34 shows TEM images of silica particles produced by combining two growth techniques at mole ratio [$H_2O$]/[surfactant]=6: (a) Seed: 50-60 nm, TEOS 1.2 mmol, $H_2O$ 36 mmol, [$H_2O$]/[TEOS]=30; (b) Core+1-layer: 61-76 nm, TEOS 4.8 mmol, $H_2O$ 36 mmol, [$H_2O$]/[TEOS]=7.5; (c) Core+2-layer: 95-113 nm, TEOS 9.6 mmol, $H_2O$ 72 mmol, [$H_2O$]/[TEOS]=7.5; (d) Core+3-layer: 100-135 nm, TEOS 14.4 mmol, $H_2O$ 72 mmol, [$H_2O$]/[TEOS]=5; (e) Core+4-layer: 136-166 nm, TEOS 24 mmol, $H_2O$ 144 mmol, [$H_2O$]/[TEOS]=6; (f) Core+5-layer: 146-172 nm, TEOS 33.6 mmol, $H_2O$ 144 mmol, [$H_2O$]/[TEOS]=4.3; (g) Core+7-layer: 200-240 nm, TEOS 52.8 mmol, $H_2O$ 216 mmol, [$H_2O$]/[TEOS]=4.1;

FIG. 35 shows TEM images of silica particles produced by combining two growth techniques at mole ratio [$H_2O$]/[surfactant]=9: (a) Seed: 50-61 nm, TEOS 1.2 mmol, $H_2O$ 54 mmol, [$H_2O$]/[TEOS]=45; (b) Core+1-layer: 70-87 nm, TEOS 4.8 mmol, $H_2O$ 54 mmol, [$H_2O$]/[TEOS]=11.3; (c) Core+2-layer: 95-117 nm, TEOS 9.6 mmol, $H_2O$ 162 mmol, [$H_2O$]/[TEOS]=16.9; (d) Core+3-layer: 158-172 nm, TEOS 14.4 mmol, $H_2O$ 162 mmol, [$H_2O$]/[TEOS]=11.3; (e) Core+4-layer: two size nanoparticles, TEOS 24 mmol, $H_2O$ 378 mmol, [$H_2O$]/[TEOS]=15.8; (f) Core+5-layer: broad size nanoparticles, TEOS 33.6 mmol, $H_2O$ 378 mmol, [$H_2O$]/[TEOS]=11.3;

FIG. 36 shows TEM images of silica nanoparticles synthesised at high temperatures with mole ratio of [$H_2O$]/[surfactant]=6: (a) 35-50 nm ageing 20 hrs at 35±2° C.; (b) 48-62 nm ageing 48 hrs at 35±2° C.; (c) 37-52 nm ageing 20 hrs at 50±2° C.; (d) 48-70 nm ageing 48 hrs at 50±2° C.;

FIG. 37 shows TEM images of silica nanoparticles synthesised at high temperatures with mole ratio of [$H_2O$]/[surfactant]=8: (a) Seed: 35-68 nm at room temperature 35±2° C. ageing 48 hrs: Core-shell particles; (b) 75-100 nm, ageing 20 hrs at 35±2° C.; (c) 78-113 nm, ageing 28 hrs at 35±2° C.; (d) 81-117 nm, ageing 48 hrs at 35±2° C.; (e) 78-105 nm, ageing 20 hrs at 50±2° C.; (f) 80-107 nm, ageing 28 hrs at 50±2° C.; (g) 86-120 nm, ageing 48 hrs at 50±2° C.

DETAILED DESCRIPTION OF THE PREFERRED EMBODIMENTS

Figure 2:
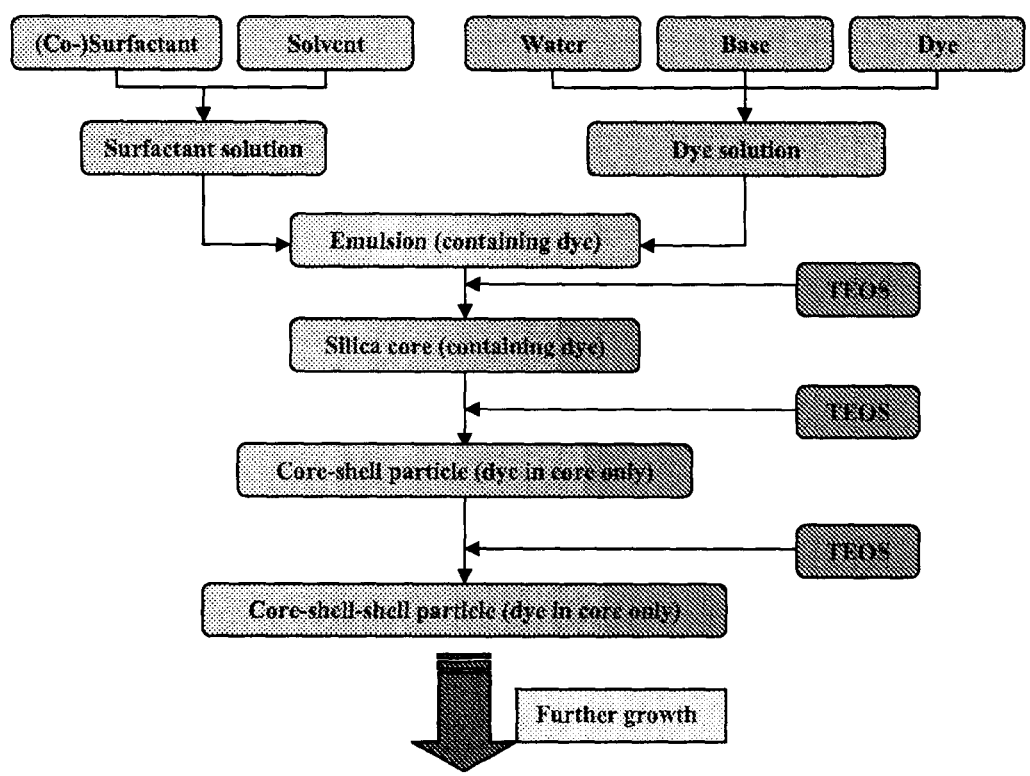
FIG. 2 shows a flow chart of a process for producing multilayered nanoparticles with dopants contained in the core only.

The present invention relates to inorganic/inorganic particles core shell particles and, in some embodiments, to particles made out of ceramic materials, with a ceramic core and one or more ceramic layer, or shell. The invention is applicable to a variety of porous metal oxide shells and non-porous or porous (oxide or non oxide) cores for example silica.

Silica core-shell particles can be divided into:
Silica particles with incorporated dyes
Silica coated metal clusters
Core-shell organosilicon with incorporated dyes The first and third categories are of particular interest for the encapsulation and release from core-shell particles. The particles of the present invention differ from the prior art in that a dopant may be doped in any of the layers. Thus in many of their embodiments the particles of the present invention may be considered as being multi-layered nanoparticles with at least one of the shell and a layer containing at one or more dopants being homogeneously distributed throughout the layer and capable of being released.

To be able to tailor the composition of each of the individual layers of the multi-layer particles it is possible to exploit the ability to change the micelle pool compositions. This may be achieved, as described herein, by sequential addition of the surfactant/water and a reagent precursor. It may be important to maintain the emulsion composition (i.e. the same spot in the ternary phase diagram: Surfactant-Oil-Water) that allows production of homogeneous multi-layered particles with identical core-shell structures and does not lead to generation of particles with different composition. Thus the present invention provides a cyclic addition of emulsion and precursor that facilitates production of multilayered particles.

The present specification discloses a sol-gel process for producing layered nanoparticles via a water-in-oil microemulsion (W/O) system. The nanoparticles may be multi-layered. The resulting nanoparticles may contain one or more active molecules, encapsulants and/or dopants, encapsulated in different locations within the nanoparticles, which may be released in a controlled fashion. The nanoparticles may be ceramic nanoparticles. They may be synthesised by sequentially adding (different) active molecules (dopants) and (different) precursors (or organically modified precursors), as well as fresh W/O emulsions. The overall particle size as well as the core diameter and each layer thickness may be tailored by controlling the amount of precursor added. The thickness of each layer may be controlled between about 1 and 50 nm. The precursor may be a hydrolysable species, e.g. a hydrolysable silane. It may be capable of hydrolyzing to form the reagent. The precursor may be varied from silicon alkoxide to other metal alkoxide or a mixture of metal alkoxides. Depending on their location in the multilayered particles, the active molecules may be released sequentially or in segmented fashion (e.g. release-no release-release). Thus for example if a nanoparticle is constructed having a releasable substance in the core and in an outer layer, with an inner layer between the outer layer and the core having no releasable substance, then release of the releasable substance would proceed stepwise, with release-no release-release steps occurring sequentially.

In the process of the present invention, the core particles may be formed in situ or they may be added as preformed particles. The core particles may be any species of powder, for example silica particles (such as fumed silica, colloidal silica or silica fume), metal oxide particles (such as indium oxide), mixed metal oxide particles (such as indium oxide doped silica particles), semiconductor particles, quantum dots, magnetic particles, crystalline particles or some other type of particles. The core particles may be spherical, or cubic, or may be in the shape of a triangular prism, a tetrahedron, a polyhedron (for example with 4, 5, 6, 7, 8, 9, 10, 11, 12, 13, 14, 15, 16, 17, 18, 19 or 20 or more than 20 faces), a flake or an irregular shape. The core particles may be crystalline or non-crystalline, or may be partly crystalline. It may be porous or non-porous. The core particles may be between about 5 and 500 nm in diameter, or between about 5 and 450, 5 and 400, 5 and 300, 5 and 200, 5 and 100, 5 and 50, 5 and 20, 10 and 500, 10 and 400, 10 and 200, 10 and 100, 50 and 500, 50 and 400, 50 and 200, 50 and 100, 100 and 500, 100 and 400, 100 and 200, 200 and 500 or 300 and 500 nm, for example about 5, 10, 15, 20, 25, 30, 35, 40, 45, 50, 60, 70, 80, 90, 100, 150, 200, 250, 300, 350, 400, 450 or 500 nm in diameter, or some other diameter. The non-polar liquid (or each non-polar liquid independently if two or more are used in different steps) may be a hydrocarbon, and may have between 5 and 16 carbon atoms, or between 5 and 12, 5 and 8, 6 and 12 or 6 and 10, and may have 5, 6, 7, 8, 9, 10, 11, 12, 13, 14, 15 or 16 carbon atoms. It may be straight chain, branched, cyclic and may be aliphatic or aromatic. It may be a mixture of hydrocarbons. Alternatively it may be some other non-polar liquid, for example a haloalkane or haloaromatic liquid or a low viscosity silicone, for example a low viscosity dimethylsilicone or a low viscosity fluorosilicone. The low viscosity silicone may be a linear silicone or a cyclic silicone. The viscosity of the silicone may be below about 100 cS, or below about 50, 20, 10, 5, 2 or 1 cS, and may be about 0.5, 1, 2, 3, 4, 5, 10, 20, 30, 40, 50, 60, 70, 80, 90 or 100 cS. The linear silicone may be a trimethylsiloxy ended silicone. The cyclic silicone may be a D3, D4, D5, D6, D7 or D8 cyclic silicone or may be a mixture of any two or more of these. A typical hydrocarbon that may be used is cyclohexane. The non-polar liquid may be recyclable. The catalyst may be a catalyst for the sol-gel process. It may be a catalyst for condensation of the condensable species, and may be for example a strong acid (such as sulfuric acid, hydrochloric acid), an organic acid (such as acetic acid, trifluoroacetic acid), a base (for example a hydroxide such as KOH, NaOH, aqueous ammonia), an amine (for example ORMOSIL functionalized with amine such as APTES (aminopropyltriethoxysilane)), a fluoride (for example HF, NaF, KF, NH$_4$F) or a transition metal alkoxide (for example titanium alkoxide, vanadium alkoxide). The concentration of the catalyst in the aqueous liquid may be between about 0.1 and 5M and may be between about 0.1 and 2, 0.1 and 1, 0.1 and 0.5, 0.5 and 5, 1 and 5, 3 and 5, 0.5 and 2 or 1 and 2M, and may be about 0.1, 0.2, 0.3, 0.4, 0.5, 0.6, 0.7, 0.8, 0.9, 1, 1.1, 1.2, 1.3, 1.4, 1.5, 2, 2.5, 3, 3.5, 4, 4.5 or 5M. The pH of the aqueous liquid may be between about 8 and 14, or between about 8 and 13, 8 and 12, 8 and 11, 8 and 10, 9 and 13, 10 and 13, 11 and 13, 9 and 12, 10 and 12 or 11 and 12, and may be about 8, 8.5, 9, 9.5, 10, 10.5, 11, 11.5, 12, 12.5, 13, 13.5 or 14. The ratio of the aqueous liquid to the suspension of core particles on a v/v basis may be between about 0.1 and 10%, or between about 0.1 and 5, 0.1 and 2, 0.1 and 1, 0.5 and 10, 1 and 10, 5 and 10, 0.5 and 5, 0.5 and 2 or 1 and 2%, and may be about 0.1, 0.5, 1, 1.5, 2, 2.5, 3, 3.5, 4, 4.5, 5, 5.5, 6, 6.5, 7, 7.5, 8, 8.5, 9, 9.5 or 10%. The ratio of the hydrolysable species to the aqueous liquid may be between about 0.5 and 10% on a w/w, w/v, v/v or molar basis, and may be between about 0.5 and 5, 0.5, and 2, 0.5 and 1, 1 and 10, 5 and 10 or 2 and 5%, and may be about 0.5, 1, 1.5, 2, 2.5, 3, 3.5, 4, 4.5, 5, 5.5, 6, 6.5, 7, 7.5, 8, 8.5, 9, 9.5 or 10% on a w/w, w/v, v/v or molar basis. The hydrolysable species may be a hydrolysable metal species, for example a hydrolysable silicon, aluminium or titanium species. The hydrolysable species may be an alkoxide, such as a metal alkoxide (e.g. silicon alkoxide, titanium alkoxide or aluminium alkoxide). The alkoxide may be a C1 to C6 straight chain or branched chain alkoxide or may be a mixture of such alkoxides. Alternatively the hydrolysable species may be an aryloxide, for example phenoxide, a silicon alkanoate, for example a silicon propionate, and aminosilane, an amidosilane or some other hydrolysable silane. The metal may have between 2 and 4 hydrolysable groups per molecule on average, and may have about 2, 2.5, 3, 3.5 or 4 hydrolysable groups per molecule on average. Suitable hydrolysable species include, but are not restricted to, tri- and tetra-alkoxysilanes such as tetramethoxysilane (TMOS), tetraethoxysilane (TEOS), tetrabutoxysilane (TBOS), tetrapropoxysilane (TPOS), methyltrimethoxysilane (MTMS), methyltriethoxysilane (MTES), ethyltriethoxysilane (ETES), ethyltrimethoxysilane (ETMS), octyltriethoxysilane (OTES), octyltrimethoxysilane (OTMS), hexadecyltrimethoxysilane (HDTMS), hexadecyltriethoxysilane (HDTES), octadecyltrimethoxysilane (ODTMS), octadecyltriethoxysilane (ODTES), as well as methyl polysilicate (MPS), ethyl polysilicate (EPS), polydiethoxysilane (PDES), hexamethyl disilicate, hexaethyl disilicate or functional trialkoxysilanes such as methacryloyloxypropyltrimethoxysilane, phenyltriethoxysilane (PTES), phenyltrimethoxysilane (PTMS), glycidoxypropyltrimethoxysilane (GLYMO), glycidoxypropyltriethoxysilane (GLYEO), mercaptopropyltriethoxysilane (MPTES), mercaptopropyltrimethoxysilane (MPTMS), aminopropyltrimethoxysilane (APTMS), aminopropyltriethoxysilane (APTES), 3-(2-aminoethylamino)propyltrimethoxysilane (DATMS), 3-[2-(2-aminoethylamino)ethylamino]propyltrimethoxysilane (TATMS), [2-(cyclohexenyl)ethyl]triethoxysilane (CHEETES), vinyltrimethoxysilane (VTMS), vinyltriethoxysilane (VTES) and mixtures of these. The hydrolysable species may be capable of hydrolysing to produce a condensable species. The condensable species may be a partial or complete hydrolysate of any of the above hydrolysable species. It may be a silanol species, and may have 1, 2, 3 or 4 silanol groups per molecule, or more than 4 silanol groups per molecule. It may be an at least partially condensed material having 1 or more silanol groups per molecule. It may be a mixture of silanol species. Thus the core and the one or more layers may, independently, comprise silica, polysilsesquioxane, alumina, titania or some other metal oxide. If the hydrolysable species is organofunctional, this may provide a condensable species which is similarly organofunctional, and ultimately may lead to a nanoparticle which is similarly organofunctional, optionally selectively organofunctional in one or more of the core and the layer(s). This may provide selective affinity for a dopant or other species for the organofunctional core and/or layer(s). Alternatively, it may be possible to provide a particle with core having a precursor to a desired compound, and one or more layers surrounding the core having a catalyst and/or reagent(s) for converting the precursor into the desired compound. In use, the precursor may be released from the core, and be converted into the desired compound by the catalyst and/or reagent(s) for release from the particle. This may be of particular use if the desired compound is of limited stability, and/or if the precursor is more stable than the desired compound.

The sufficient temperature to hydrolyse may be between about 1 and 70° C., or between about 1 and 50, 1 and 30, 1 and 20, 1 and 10, 1 and 5, 10 and 50, 10 and 40, 10 and 30, 10 and 20, 15 and 40, 20 and 50, 50 and 70, 30 and 50, 20 and 40 or 20 and 30° C., and may be about 1, 2, 3, 4, 5, 6, 7, 8, 9, 10, 15, 20, 25, 30, 35, 40, 45, 50, 55, 60, 65 or 70° C. The sufficient time may be between about 6 and 96 hours, or between about 6 and 72, 6 and 48, 6 and 24, 12 and 96, 24 and 96, 36 and 96, 48 and 96, 60 and 96, 12 and 72, 24 and 60, 36 and 60 or 36 and 48 hours, and may be about 6, 12, 18, 24, 36, 48, 60, 72, 84 or 96 hours, or may be more than 96 hours. The core particles may be provided at a temperature between about 1 and 70° C., or may be brought to a temperature between about 1 and 70° C., or between about 10 and 70° C. or between about 1 and 10° C. or between about 1 and 50° C. or between about 1 and 20° C. or between about 10 and 50° C., or between about 10 and 40, 10 and 30, 10 and 20, 20 and 50, 50 and 70, 30 and 60, 30 and 50, 20 and 40 or 20 and 30° C., and may be about 1, 2, 3, 4, 5, 6, 7, 8, 9, 10, 15, 20, 25, 30, 35, 40, 45, 50, 55, 60, 65 or 70° C.

The dopant may be a salt (e.g. comprising a metal complex ion such as copper tetramine), a dye, a catalyst, a biologically active substance (for example a protein, polysaccharide, enzyme, drug, peptide etc.), a magnetic substance, a radioactive tracer or other radioactive species, or some other type of dopant. There may be different dopants in different locations within the nanoparticles (e.g. the core and each of the one or more layers may comprise different dopants). The same dopant may be located in different locations within the nanoparticles (e.g. the core and one of the one or more layers may comprise the same dopant). The or each dopant may be releasable or non-releasable. If more than one dopant is present, at least one dopant may be releasable and at least one dopant may be non-releasable, or all dopants may be releasable or all dopants may be non-releasable. A dopant in the core or a layer may be distributed through said core or layer, and may be distributed evenly or unevenly through said core or layer. It will be understood that where reference is made to a dopant, this may include a plurality of dopants (for example 2, 3, 4, 5 or more than 5 dopants). If the core particle or any of the layers comprises a plurality of dopants, they may be all releasable, or at least one may be releasable and at least one non-releasable, or they may be all non-releasable. For example a layer may comprise a mixture of releasable dopants to be released simultaneously, or it may comprise a mixture of non-releasable dopants (e.g. a dye and a magnetic dopant) to impart either a plurality of properties to the layer or a composite property (as for example if two different dyes were incorporated into a single layer), or it may comprise a releasable dopant for release to the environment surrounding the particle, together with a non-releasable dopant (for example a dye).

The dopant in the core particle, if present, may be substantially homogeneously distributed through the core particle. The dopant in the layer, or any of the layers (if more than one layer is present) may be substantially homogeneously distributed through that layer.

In an example, the layered nanoparticle may comprise a core particle having a non-releasable dye (e.g. red), and the core particle may be surrounded by a porous layer comprising a releasable dye of a different colour (e.g. green). Thus the layered nanoparticle may adopt the colour of the releasable dye (e.g. green), or a composite colour of the releasable and non-releasable dyes (e.g. brown). When the layered nanoparticle adopts the colour of the non-releasable dye (e.g. red), then a user may be alerted to the fact that the releasable dye has been released. In a particular example, the porous layer comprises a second releasable dopant (e.g. a reagent for a chemical reaction) in addition to the releasable dye. When the layered nanoparticle adopts the colour of the non-releasable dye, a user may be alerted to the fact that it is necessary to add further nanoparticles in order to ensure continued release of the releasable dopant.

The core particle may, for example, comprise a quantum dot, which may function as a non-releasable dye. The core particle may be any suitable particle, for example a porous or non-porous particle. It may be a nanoparticle.

The dopant may comprise an immobilised reagent or catalyst. For example, a nanoparticle may comprise a core particle and layer surrounding the core particle. The core particle may comprise a dopant (e.g. a prodrug) which is a precursor to a compound (e.g. a drug) to be released to the environment of the nanoparticle, and the layer may comprise a catalyst for converting the dopant into the compound. When the nanoparticle is exposed to a suitable environment, the dopant may pass from the core particle through the layer, where it would be converted under the influence of the catalyst into the compound, which would then be released from the nanoparticle. This may be useful in the case of a compound which is of limited long term stability.

A layer may comprise a release rate modifier, either in the form of a non-releasable dopant or in the form of the material of the layer itself. The release rate modifier may be capable of modifying the release rate of a releasable dopant incorporated in the layer or in a layer closer to the core particle or in the core particle. The release rate modifier may be capable of accelerating or decelerating the release of a releasable dopant. For example the core may comprise a releasable dopant which has acidic groups. A layer surrounding the core may comprise amine groups, which would slow the release of the releasable dopant.

The core or one or more layers may comprise a sorbent, either in the form of a non-releasable dopant or in the form of the material of the layer itself. For example, the core particle or a layer may comprise a non-releasable amine dopant, or the material of the core particle or layer may comprise amine groups (for example derived from aminopropyltriethoxysilane used in making the core particle or the layer), for sorbing acidic species. An example of the use of such a material may be the selective sorption of low molecular acids in the presence of high molecular weight acids. Thus a porous core particle having amine groups, for example derived from aminopropyltrimethoxysilane, aminopropyltriethoxysilane or aminoethylaminopropyltrimethoxy- or trimethoxy-silane, may have a neutral porous layer applied to it to form a nanoparticle according to the present invention. On exposure to a liquid comprising low and high molecular weight acids, the low molecular weight acids would be capable of penetrating the layer to be sorbed into the core particle, whereas higher molecular weight acids may be prevented from accessing the core particle. The high molecular weight acids would be shielded from the amine groups in the core particle, thus preventing coagulation of the liquid due to an interaction between the nanoparticles and the higher molecular weight acids. In that manner, the low molecular weight acids may be selectively removed from the mixture without coagulation of the liquid. Another example of the use of such a material may be the sorption of highly toxic materials. Thus, for example, the nanoparticle having a porous core particle with amine groups surrounded by a neutral porous layer may be used for sorbing highly toxic acidic materials safely. On exposure to a liquid comprising the toxic acidic material, the nanoparticle may sorb the toxic acidic material from the liquid into the amino functional core particle, leaving the neutral porous layer essentially free of the toxic acidic material. The resultant nanoparticle with adsorbed toxic acidic material may be safe to handle, since the outer layer of the nanoparticle would be free of the toxic acidic material.

More generally, the layered nanoparticle may comprise (in the core and/or in one or more layers) chelating and/or complexing groups that are capable of interacting specifically with a particular chemical species or class of chemical species in order to provide selective sorption of that chemical species or class of chemical species. The chelating and/or complexing groups may be either in the form of a non-releasable dopant or in the form of the material of the layer itself, or both. Such layered nanoparticles may be used for example for sorption of toxic chemicals, such as heavy metals. Thus a layered nanoparticle having a non-releasable dopant comprising a group capable of chelating lead (e.g. a bound EDTA group) may be used for removing lead from a solution.

The mean nanoparticle bulk density may be in the range $0.075$ g/cm$^3$ to $2.2$ g/cm$^3$, or about 0.15 to 1.5, 0.18 to 1.0, 0.5 to 1.0, 0.5 to 0.75 or 0.25 to 0.5 g/cm$^3$, and may be about 0.075, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1 or 2.2 g/cm$^3$.

The nanoparticulate substance may be monodispersed, or may have a narrow particle size distribution. The particle size distribution may be such that more than 50% of particles lie within 10% of the mean particle size, or more than 45%, 40%, 35%, 30%, 25%, 20%, 15% or 10%, and may be such that about 10, 20, 30, 40, 50, 60, 70 or 80% of particles lie within 10% of the mean particle size.

The nanoparticulate substance may have a mean particle diameter between about 10 and 500 nm, or between about 10 and 100, 50 and 500, 50 and 300, 50 and 100, 100 and 500, 250 and 500, 100 and 300 or 200 and 300 nm, and may have a mean particle diameter of about 10, 20, 30, 40, 50, 100, 150, 200, 250, 300, 350, 400, 450 or 500 nm, or may have a larger mean particle diameter. The particles of the nanoparticulate substance may comprise a core and between 1 and 10 layers, or layers, at least partially surrounding the core. There may be between 1 and 8, 1 and 5, 1 and 3, 2 and 10, 5 and 10, 2 and 8 or 2 and 5 layers, and may be 1, 2, 3, 4, 5, 6, 7, 8, 9 or 10 layers, or may be more than 10 layers. The mean diameter of the core may be between about 5 and 500 nm, or between about 5 and 150, 100 and 500, 100 and 500, 100 and 400, 100 and 300, 100 and 200, 100 and 150, 5 and 125, 5 and 100, 5 and 80, 5 and, 50, 5 and 30, 10 and 100, 30 and 100, 50 and 100, 100 and 150, 100 and 130, 130 and 150, 10 and 80, 20 and 70 or 30 and 70 nm, and may be about 5, 10, 15, 20, 25, 30, 35, 40, 45, 50, 55, 60, 65, 70, 75, 80, 85, 90, 95, 100, 110, 120, 130, 140, 150, 200, 250, 300, 350, 400, 450 or 500 nm. The mean thickness of each layer or layer may, independently, be between about 1 and 50 nm, or between about 1 and 30, 1 and 20, 1 and 10, 5 and 30, 5 and 10, 10 and 50, 10 and 40, 10 and 30, 10 and 20, 20 and 50, 30 and 50, 40 and 50, 20 and 40 or 20 and 30 nm, and may be about 1, 2, 3, 4, 5, 10, 15, 20, 25, 30, 35, 40, 45 or 50 nm. If more than one layer or shell is present, they may be different thicknesses or the same thickness. The core and/or the layers may be porous and may be microporous, or mesoporous, and may have a mean pore size of between about 0.5 and 20 nm, or between about 0.5 and 10, 0.5 and 5, 0.5 and 4, 0.5 and 3, 0.5 and 2, 0.5 and 1.7, 0.5 and 1, 1 and 5, 2 and 5, 3 and 5, 4 and 5, 5 and 10, 7 and 10, 10 and 20, 5 and 15, 5 and 7, 1 and 3 or 1 and 2 nm, and may have a pore size about 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9, 10, 11, 12, 13, 14, 15, 16, 17, 18, 19 or 20 nm. Thus, for example, both the core and all layers may be porous, or the core may be non-porous and the layers may be porous, or the core and an inner layer may be non-porous, and an outer layer may be porous. The core particle and the or each layer may, independently, have a porosity of between about 0 and 80%, or between about 0 and 70, 0 and 60, 0 and 50, 0 and 40, 0 and 30, 0 and 20, 0 and 10, 2 and 80, 10 and 80, 30 and 80, 50 and 80, 10 and 50, 30 and 50, 20 and 60 or 20 and 40%, and may have a porosity about 0, 10, 20, 30, 40, 50, 60, 70 or 80%. The dopant may represent between about 0 and 100 wt % of the core (i.e. the core may have no dopant or may be an active material which may or may not also be a dopant in one or more layers: the core may for example comprise a micronised drug particle or marker or quantum dot, as in the example of the $In_2O_3$ nanocrystals). The dopant may represent between about 0 and 50, 0 and 25, 0 and 10, 0 and 5, 10 and 100, 50 and 100, 5 and 95, 10 and 50 or 25 and 50 wt % of the core, and may represent about 0, 1, 2, 3, 4, 5, 10, 15, 20, 25, 30, 35, 40, 45, 50, 55, 60, 65, 70, 75, 80, 85, 90, 95, 96, 97, 98, 99 or 100 wt % or the core The dopant may represent between about 0 and 25 wt % of any particular layer surrounding the core, or between about 0 and 20, 0 and 15, 0 and 10, 0 and 5, 5 and 25, 10 and 25, 15 and 25, 20 and 25, 5 and 20 or 10 and 20 wt %, and may represent about 0, 0.1, 0.5, 1, 2, 3, 4, 5, 6, 7, 8, 9, 10, 11, 12, 13, 14, 15, 16, 17, 18, 19, 20, 21, 22, 23, 24 or 25 wt % of any particular layer surrounding the core.

The step of at least partially separating the layered nanoparticle(s) may comprise filtering, microfiltering, centrifuging, ultracentrifuging, settling, decanting or a combination of these. It may also comprise the step of destabilising the suspension, and the destabilising may be performed before said filtering, microfiltering, centrifuging, ultracentrifuging or settling.

The step of destabilising may comprise adding to the suspension a destabilising liquid. The destabilising liquid may be polar, and may be miscible with the non-polar liquid. The destabilising liquid may be miscible with water. It may be for example acetone, ethanol, methanol or some other liquid. The step of destabilising may comprise changing temperature, for example to a temperature at which the suspension is not stable. Depending on the phase diagram, the changing may be heating or may be cooling.

The steps of washing may comprise contacting the layered nanoparticle(s) with a washing liquid (either aqueous or organic) and separating the layered nanoparticle(s) from the washing liquid. For example any or all of the steps of washing may comprise suspending the layered nanoparticle(s) in the washing liquid, optionally agitating the combined washing liquid and the layered nanoparticle(s), and separating the layered nanoparticle(s) from the washing liquid, for example using any of the separation methods described above. Alternatively any or all of the steps of washing may comprise passing the washing liquid past and/or through the layered nanoparticle(s), which may be retained, for example in a filter. The washing may be performed inside a decantation funnel by phase separation. The aqueous washing liquid may be water or an aqueous liquid, for example a salt solution. The organic washing liquid may be a solvent, and may be a polar or a non-polar solvent, for example methanol, ethanol, isopropanol, acetone, dichloromethane, chloroform, ethyl acetate, toluene or some other solvent, and may be a mixture of solvents. The step of washing may also comprise heating or cooling the suspension to between about 10 and 70° C., or between about 10 and 50, 10 and 30, 10 and 20, 20 and 70, 50 and 70, 20 and 50 or 30 and 50° C., and may comprise heating or cooling the suspension to about 10, 15, 20, 25, 30, 35, 40, 45, 50, 55, 60, 65 or 70° C. The heating or cooling may be to a temperature which prevents the system from forming a single stable phase by changing the phase diagram of the system. The system may also be prevented from forming a single stable phase by using a mixture of solvents to change the phase diagram.

The step of drying may comprise heating the layered nanoparticle(s). The heating may be to a temperature below the temperature at which the dopant(s), if present, decomposes or deteriorates, and may be for example between about 30 and 80° C., or between about 30 and 60, 30 and 40, 40 and 80, 60 and 80 or 40 and 60° C., and may be about 30, 35, 40, 45, 50, 55, 60, 65, 70, 75 or 80° C. Alternatively or additionally the step of drying may comprise freeze-drying, for example as described in W01/62332 (Barbé and Bartlett, "Controlled Release Ceramic Particles, Compositions thereof, Processes of Preparation and Methods of Use"). The step of drying may additionally or alternatively comprise passing a stream of gas over and/or through the layered nanoparticle(s). The gas may be a gas that is inert to the layered nanoparticle(s) and to any dopant therein and/or thereon, and may be for example air, nitrogen, argon, helium, carbon dioxide or a mixture of these, and may be dried. The step of drying may additionally or alternatively comprise applying a partial vacuum to the layered nanoparticle(s). The partial vacuum may have an absolute pressure of for example between about 0.01 and 0.5 atmospheres, or between about 0.01 and 0.1, 0.01 and 0.05, 0.1 and 0.5, 0.25 and 0.5, 0.05 and 0.1 or 0.1 and 0.25 atmospheres, and may have an absolute pressure of about 0.01, 0.05, 0.1, 0.2, 0.3, 0.4 or 0.5 atmospheres.

In an embodiment of the process of the invention the step of providing a suspension comprising a core particle in a non-polar liquid comprises the steps of:

providing an emulsion comprising aqueous droplets dispersed in a non-polar liquid, wherein the droplets comprise a catalyst for hydrolysis of a first hydrolysable species, said first hydrolysable species being capable of producing a first condensable species upon hydrolysis; and adding the first hydrolysable species to the emulsion so that the first hydrolysable species hydrolyses within the droplets to form a suspension of core particles in the non-polar liquid.

The aqueous droplets may be between about 5 and 150 nm in diameter, or between about 5 and 125, 5 and 100, 100 and 130, 120 and 150, 5 and 80, 5 and, 50, 5 and 30, 10 and 100, 30 and 100, 50 and 100, 10 and 80, 20 and 70 or 30 and 70 nm, and may be about 5, 10, 15, 20, 25, 30, 35, 40, 45, 50, 55, 60, 65, 70, 75, 80, 85, 90, 95, 100, 110, 120, 130, 140 or 150 nm in diameter.

The step of providing an emulsion may comprise the steps of:

providing a surfactant solution comprising a surfactant and a non-polar liquid, and optionally a co-surfactant;

adding to the surfactant solution an aqueous solution comprising a catalyst for condensation of a first condensable species and, optionally, also comprising a first dopant;

forming an emulsion from the surfactant solution and the aqueous solution;

The surfactant may be an anionic, cationic, non-ionic or zwitterionic surfactant, and may be a monomeric or polymeric surfactant. Suitable surfactants include nonylphenoxypolyethoxyethanol, $C_9H_{19}C_6H_4(OCH_2CH_2)_nOH$ (NP series), or octylphenoxypolyethoxyethanol $C_8H_{17}C_6H_4(OCH_2CH_2)_nOH$ (Triton series), where n is between 4 and 15, or between 4 and 9 or 9 and 15 or 7 and 12, and may be 4, 5, 6, 7, 8, 9, 10, 11, 12, 13, 14 or 15. Suitable cosurfactants include C5 to C10 n-alcohols (1-pentanol, 1-hexanol, 1-heptanol, 1-octanol, 1-nonanol, 1-decanol). The concentration of the surfactant in the surfactant solution may be sufficient to form a stable microemulsion in combination with suitable amounts of water and cosurfactant, and may be between about 0.05 and 1M, or between about 0.05 and 0.5, 0.05 and 0.2, 0.05 and 0.1, 0.1 and 1, 0.5 and 1, 0.1 and 0.5 or 0.1 and 0.2M, and may be about 0.05, 0.06, 0.07, 0.08, 0.09, 0.1, 0.15, 0.2, 0.25, 0.3, 0.4, 0.5, 0.6, 0.7, 0.8, 0.9 or 1M, or may be some other suitable concentration. The concentration of the cosurfactant in the surfactant solution may be between about 0 and 1M, or between about 0.05 and 1, 0.05 and 0.5, 0.05 and 0.2, 0.05 and 0.1, 0.1 and 1, 0.5 and 1, 0.1 and 0.5 or 0.1 and 0.2M, and may be about 0, 0.05, 0.06, 0.07, 0.08, 0.09, 0.1, 0.15, 0.2, 0.25, 0.3, 0.4, 0.5, 0.6, 0.7, 0.8, 0.9 or 1M. The molar ratio of cosurfactant to surfactant may be between 0 and 10 or between about 0 and 5, 0 and 2, 0 and 1.5, 0 and 1, 0 and 0.5, 0 and 0.2, 0 and 0.1, 0.5 and 2, 1 and 2, 1.5 and 2, 0.5 and 1.5 or 0.8 and 1.2, 0.5 and 10, 1 and 10, 2 and 10, 5 and 10, 0.5 and 5 or 1 and 5 and may be about 0. 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9 or 10. The ratio of water in the aqueous liquid to the surfactant may be between about 2:1 and 10:1, or between about 2:1 and 5:1, 3:1 and 10:1, 4:1 and 10:1, 5:1 and 10:1, 3:1 and 8:1 or 4:1 and 6:1, and may be about 2:1, 3:1, 4:1, 5:1, 6:1, 7:1, 8:1, 9:1 or 10:1 on a w/w, w/v, v/v or molar basis.

Synthesis of Nanoparticles

Figure 3:
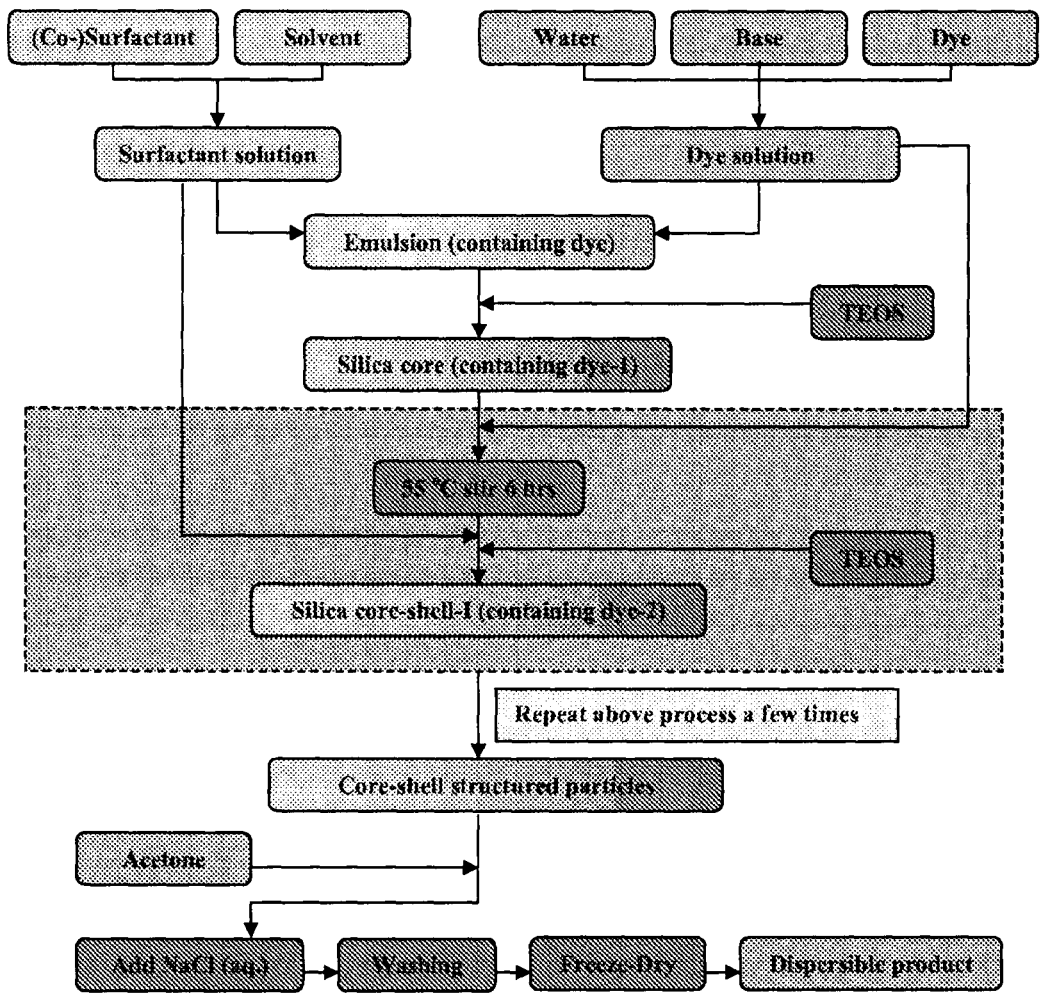
FIG. 3 shows a flow chart of the process for producing multilayered nanoparticles with multiple dopants.

FIG. 3 summarizes a process according to the present invention. The process may be described as follows:

1. A surfactant solution is formed by dissolving a surfactant and a co-surfactant in an non-polar solvent such as cyclohexane.

2. An aqueous solution is formed by mixing the active molecule (dopant) to be encapsulated (e.g. dye or drug) with a catalyst for the sol-gel reaction (e.g. base).

3. A stable microemulsion is then prepared by mixing the surfactant and the aqueous solution as produced above. An alkoxide precursor (e.g. TEOS) is then added to the microemulsion and subsequently slowly diffuses to the water pools (i.e. core of the emulsion droplets) where it is hydrolysed.

4. After hydrolysis and condensation of the metal alkoxide for at least 48 hours, the reaction temperature is increased to 55±5° C. for one hour to ensure completion of the reaction. This stage results in the production of the core (or seed) particles.

5. More aqueous solution (which may contain another active molecule) is then added. The mixture is stirred at 55±5° C. for six hours to allow the added water to be transferred at the surface of the core particles. This is important in order to prevent empty micelle formation, which may be a source of secondary nucleation. A surfactant solution containing surfactant, co-surfactant and non-polar solvent is then added. After the system is cooled to room temperature, further precursor (e.g. TEOS) is added to grow the particles by forming a layer around the original core particles. Synthesis parameters such as water to surfactant molar ratio, surfactant concentration are kept constant during these steps.

6. Steps 4 and 5 are repeated one or more times to produce the required number of layers in the layered nanoparticles. Note that by using this process, different dopants may be incorporated in different locations (i.e. layers) of the layered nanoparticles.

7. After the layered nanoparticles are formed, a polar solvent (e.g. acetone) is added to the mixture to destabilise the emulsion system and to extract the particles by settlement or centrifugation. If required, more solvent is used to remove the residual surfactant.

8. A salt solution is added and the particles are then further washed with chloroform, collected in separation funnel, and freeze-dried using a procedure described in W01/62332 (Barbé and Bartlett, "Controlled Release Ceramic Particles, Compositions thereof, Processes of Preparation and Methods of Use"). The particles may also be processed in suspension. A polar solvent (e.g. acetone) is added to the mixture to destabilise the emulsion system and the particles are extracted by settling or centrifugation. If required, more solvent can be used to further remove the surfactant residues.

Factors that control the final particle size and size distribution include emulsion parameters (e.g. surfactant concentration, surfactant/water ratio, precursor/water ratio), the nature and amount of metal precursor, and the cycle time of step 4 and 5. The number of layers depends on how many times steps 4 and 5 are repeated. The type and concentrations of active molecules (dopants) may be altered at each cycle. The location of each active molecule depends on when it is introduced in the process, and the thickness of each layer may be controlled by the amount of precursor added.

Comparison with Other Growth Method Reported in the Literature

In contrast to the experiments reported in the literature, a process according to the present invention uses a seed growth technique to produce core-shell layered nanoparticles by maintaining the same oil-water-surfactant (optionally with cosurfactant) phase diagram. This may be achieved by adding fresh W/O microemulsion, or fresh surfactant and non-polar solvent, to the reaction system during the growth of each layer. Thus, addition of a second non-polar solvent should not alter the oil-water-surfactant phase diagram significantly, and the second non-polar solvent should be miscible with the non-polar solvent which was used initially. The process may proceed continuously without extracting seeds. Another unique feature of the present invention is the possibility of introducing new active molecules during each addition of fresh microemulsion. Hence a novel approach can be developed to form core-shell layered nanoparticles, by which more than one dopant can be encapsulated in the core or selected shell(s) (layer(s)). The encapsulated molecules may then be released in a predetermined release sequence depending on their location inside the multi-layered structure. This ability to control the payload in each layer enables the design of delayed (empty layer+loaded core), as well as pulsed (alternate empty and filled layer) and sequential release (layers filled with different payload) systems. Furthermore, not only the overall particle size be controlled, but the thickness of the core and each layer can be tailored, thus potentially controlling the length of the release cycles. Although the encapsulation of multi-active molecules in particles or film has not been extensively studied, the inventors believe that this advanced controlled release technology may find applications not only in traditional applications for controlled release systems such as food, chemical, biocide, pesticide, pharmaceutical and cosmetic, but also in other areas such as optical sensor, biosensor, encryption and information technology.

Examples

Materials

NP-9 [nonylphenoxypolyethoxyethanol, $C_9H_{19}C_6H_4(OCH_2CH_2)_nOH$, n=9] (Fluka: MW 630, HLB 13.0) was used as received (i.e. contains less than 0.08 wt. % of water as determined by Karl Fisher titration). Tetraethylorthosilicate (TEOS) (98%) from Sigma-Aldrich was also used as received. Organic solvents (cyclohexane, 1-pentanol, acetone, chloroform) were ACS spectrophotometric grade (99+%) (Sigma-Aldrich). All other chemical reagents used were A.R. grade. High purity Milli-Q water (Millipore) was used for the preparation of all aqueous solutions; its resistivity was above 18.2 MΩ cm. All samples were stored in the dark.

Preparation of Encapsulant (Dopant) Solution:

Preparation of Copper (II) Tetramine Nitrate:

Copper (II) tetramine nitrate solution was prepared by adding 25 wt. % ammonia dropwise to a known quantity of copper (II) nitrate-hydrate, until a dark blue solution was formed. The solution was transferred to 100 mL volume flask and the volume was adjusted to 100 ml by adding diluted 25 volume percent of concentrated ammonia (i.e. 25 wt % $NH_3$). The prepared solution contained copper 16.69 mg/mL and its pH was measured as 11.86.

Preparation of Cobalt (III) Hexamine Nitrate:

Cobalt (III) hexamine nitrate solution was prepared by similar procedure as described above for copper (II) tetramine nitrate solution, except that during dissolution of cobalt nitrate-hydrate by concentrated ammonia (25 wt. % $NH_3$), the solution was heated to boil for twenty minutes leading to formation of soluble cobalt (III) hexamine complexes. The final solution contained cobalt 16.69 mg/mL, and pH was 11.82.

Preparation of Rubpy:

A Rubpy [(tris(2,2'-bipyridyl)dichlororuthenium(II) hexahydrate] solution was prepared by dissolving a fixed amount of ruthenium complex in a fixed volume of diluted ammonia (10 vol % of concentrated 25 wt % $NH_3$) to make a solution with a concentration of 2.5 mg/mL of Rubpy.

Preparation of CuPC:

A CuPC [copper(II) phthalocyanine-tetrasulfonic acid tetrasodium salt] solution was prepared by dissolving a fixed amount of copper complex into a fixed volume of diluted ammonia (10 vol % of concentrated 25 wt % $NH_3$) to make a solution with a concentration of 5 mg/mL of CuPC.

Preparation of FITC:

A fluorescein isothiocyanate solution was prepared by dissolving a fixed amount of fluorescein into a fixed volume of diluted ammonia (10 vol % of concentrated 25 wt. % $NH_3$) to make a solution with a concentration of 5 mg/mL of Fluorescein.

Preparation of In-DTPA or Ga-DTPA Solution:

A known amount of $InCl_3$ or $GaCl_3$ was weighed in 100 mL beaker, 10 g Milli-Q water was added to dissolve the salt. A fixed amount of diethylenetriamine pentaacetic acid (DTPA) was added so that the DTPA to metal element molar ratio was kept at 1.1:1. Concentrated ammonia (25 wt % $NH_3$) was added dropwise as the mixture was stirred magnetically. After all of the DTPA was dissolved, the metal-DTPA chelate was formed with formula as $[Me-DTPA]^{2-}$ and structure as following:

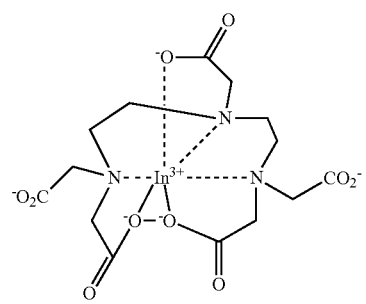

The concentrated ammonia was added continuously until the pH of solution was above 11.50 and total volume was just below 100 mL. The solution was transferred to 100 mL volume flask quantitatively, and water was added to a final volume of 100 mL.

Figure 4:
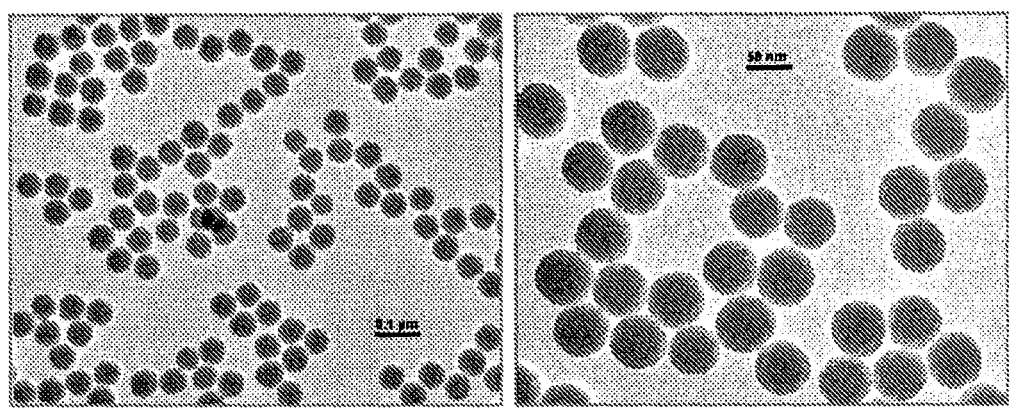
FIG. 4 shows TEM micrographs of particles produced in a NP-9/1-pentanol/cyclohexane/$NH_4OH$/TEOS system (average size 55±5 nm)

Typical Preparation for Producing 50 Nm Silica Core 7.56 g of NP-9 (12 mmol) was dissolved in 60 mL cyclohexane in a 250 mL screw capped container. 1.304 mL (12 mmol) of 1-pentanol was then added. This mixture was shaken vigorously for about 1 minute to prepare the surfactant solution. Then 1.333 mol/L of ammonia solution ($NH_4OH$ (pH~11.86) 1.296 mL (i.e. 72 mmol of water) containing the active molecules, such as a dye, was added. The mixture was stirred vigorously for about thirty minutes to produce the microemulsion system. 0.546 mL of TEOS (2.4 mmol) was added into this magnetically stirred microemulsion, which was then left to stir for a fixed time (48-72 hours) at room temperature, 22±2° C. This was followed by the addition of 50 mL of dry acetone to destabilise the microemulsion. The system was further stirred vigorously for about 10 minutes. The silica particles usually flocculated and could be separated by decantation; if no significant sedimentation was observed, the mixture was centrifuged at 4000 rpm for 10 minutes. After sedimentation or centrifugation, the particles were separated from the organic phase and washed three times with 50 mL of dry acetone (each time) to remove the surfactant. After decantation of the acetone, about 20 mL NaCl aqueous solution was mixed with particles and introduced in a decantation funnel. The resulting suspension was further washed 6 times using chloroform (50 mL each times) to remove the residual surfactant, ultrasonicated and freeze dried using a Flexi-dry-84D freeze-drier (FTS Systems, Inc., Stone Ridge, N.Y.). Using this procedure, 144 mg silica were produced in the formed of nanoparticles homogeneously distributed inside a NaCl matrix. TEM shows the particle size was in the range of 55±5 nm (FIG. 4 and FIG. 5-A). The sodium chloride is used as a protective matrix to prevent the nanoparticles from aggregating and the weight ratio between silica and sodium chloride is kept around 15%.

Typical Experimental Procedures for Preparing, 100 Nm, 150 Nm and 200 Nm Silica Nanoparticles Preparation 2: 100 Nm (Core+1 Shell):
Produce 50 nm seeds using the procedure described above;
Instead of adding acetone to destabilised the microemulsion, increase temperature to 55±5° C. and stir for one hour;
Then add 2.952 mL of 1.333 mol/L $NH_4OH$ (pH~11.86) (i.e. equivalent water 144 mmol) and stir for 6 hours at 55±5° C., then cool down to room temperature;
Add 15.12 g NP-9 (24 mmol) mixed with 2.608 mL 1-pentanol (24 mmol), and 120 mL of cyclohexane and stir for 20 minutes;
Add 2.184 mL TEOS (9.6 mmol) to the mixture;
Stir 48-72 hours;
Wash, extract and dry the particles as described in Typical preparation for producing 50 nm silica core above;

This procedure produces 720 mg of monodisperse 100 nm silica nanoparticles. The corresponding TEM micrographs are presented in FIG. 5-B.

Preparation 3: 150 Nm (Core+2 Shells):
Prepare 100 nm particles as describe above;
Instead of adding acetone to destabilised microemulsion, split the emulsion into two aliquots;
Take one aliquot, increase its temperature to 55±5° C. and stir for one hour. Then add 2.592 mL of 1.333 mol/L $NH_4OH$ (pH~11.86) (i.e. equivalent water 144 mmol) and stir for 6 hours at 55±5° C.;
Add 15.12 g of NP-9 (24 mmol) mixed with 2.608 mL 1-pentanol (24 mmol), and 120 mL of cyclohexane and stir for 20 minutes;
Add 2.184 mL TEOS (9.6 mmol) into the mixture;
Stir for 48-72 hours;
Wash, extract and dry the particles as described in Typical preparation for producing 50 nm silica core above;

This procedure produces 936 mg of relatively monodisperse 150 nm silica nanoparticles. The corresponding TEM micrographs are presented in FIG. 5-C.

Preparation 4: 200 Nm (Core+3 Shells):
Prepare 150 nm particles as described above;
Instead of adding acetone to destabilised microemulsion, split emulsion into two aliquots;
Take one aliquot and heat it up to 55±5° C., stir for one hour, and add 2.592 mL of $NH_4OH$ 1.333 mol/L (pH~11.86) (i.e. equivalent water=144 mmol); stir for an additional 6 hours at 55±5° C.;
Add 15.12 g NP-9 (24 mmol), mixed with 2.608 mL 1-pentanol (24 mmol) in 120 mL cyclohexane and stir for 20 minutes;
Add 2.184 mL TEOS (9.6 mmol) to the system;
Stir for 48-72 hours;
Wash, extract and dry particles as described in Typical preparation for producing 50 nm silica core above;

This procedure produces 1044 mg of relatively monodisperse 200 nm silica nanoparticles. The corresponding TEM micrographs are presented in FIG. 5-D.

Particle Characterisation

The size and morphology of silica particles were monitored using a transmission electron microscope (JEOL 2000 FXII or JEOL 2010F).

Figure 6:
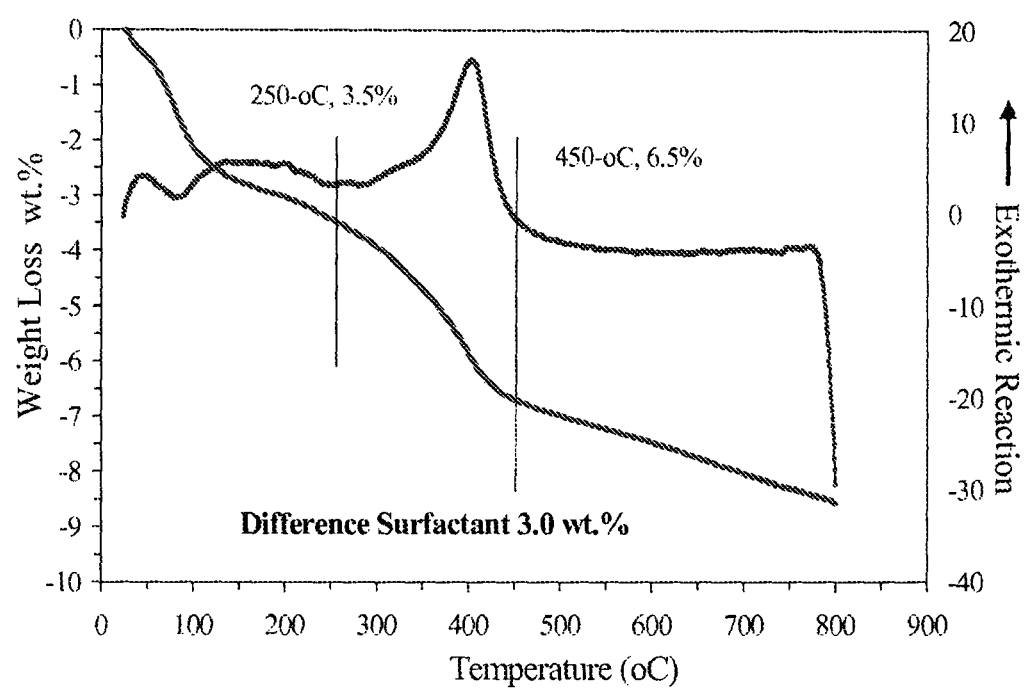
FIG. 6 shows a graph of TGA/DTA measurement of surfactant residue on silica particles.

To monitor the amount of residual surfactant TGA/DTA experiments were performed using a Setaram TGA 24. Undoped samples were heated to 900° C. at a rate of 10° C./min. A typical diagram is shown in FIG. 6. Two different decomposition reactions were observed by DTA: an endothermic reaction at about 100-200° C. associated with the evaporation of water and other volatile components and an exothermic reaction at approximately 400° C. associated with the combustion of the surfactant. The amount of bound surfactant was calculated as the difference between the weight loss at 450° C. and the weight loss at 250° C. The surfactant residue associated with the silica particles after washing five times in chloroform is about 3.0 wt % of the silica dry weight. This corresponds to about 1.65 molecules of NP-9 per 50 nm particle.

Release Rate of Dyes

After separation of the silica particles from the aqueous phase by centrifugation, the particles were resuspended in 20 mL of simulated body fluid (SBF, pH 7.4/25° C.). The composition of SBF can be seen from P. Kortesuo; M. Ahola; S. Karlsson; I. Kangasniemi; A. Yli-Urpo; J. Kiesvaara, "Silica xerogel as an implantable carrier for controlled drug delivery—evaluation of drug distribution and tissue effects after implantation", *Biomater.*, 21, 193-198 (2000). The release was measured by centrifuging at 3000 rpm for half an hour the suspension and measuring the concentration of dopant released in the supernatant using UV-visible spectroscopy. During the release study, the samples were store in 37° C. water bath, and kept in the dark.

Results and Discussion

Influence of the Emulsion Parameters on the Seed Size

Figure 7A:
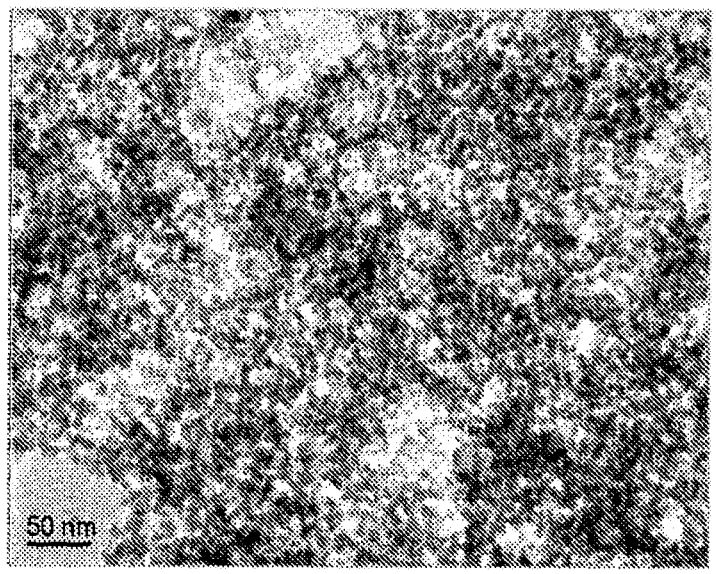
FIG. 7-$a$ shows a TEM micrograph of silica particles produced in the microemulsion system a) NP-5/cyclohexane/NH4OH/TMOS.
Figure 7B:
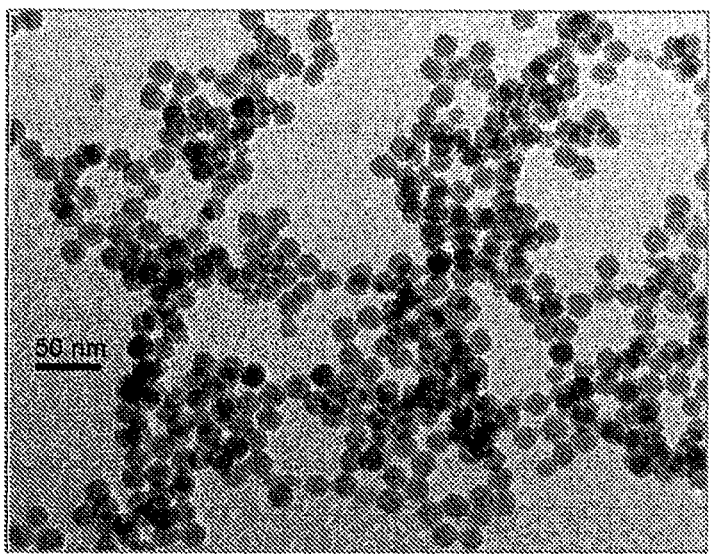
Figure 7C:
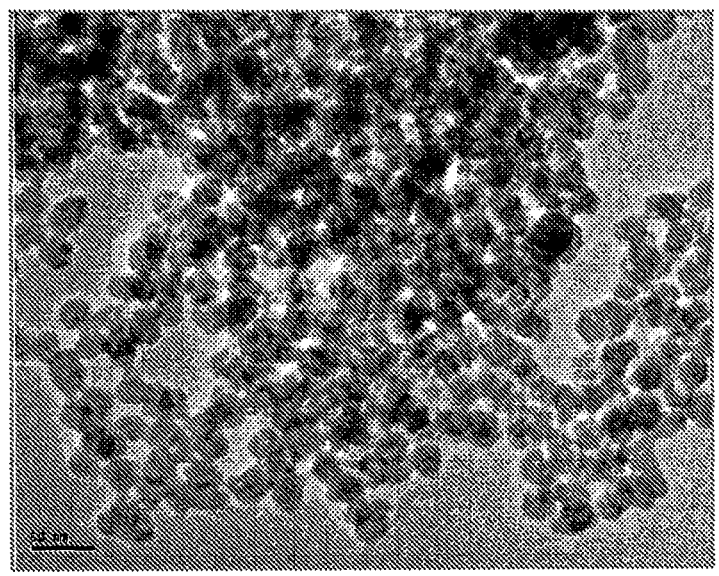
Figure 8A:
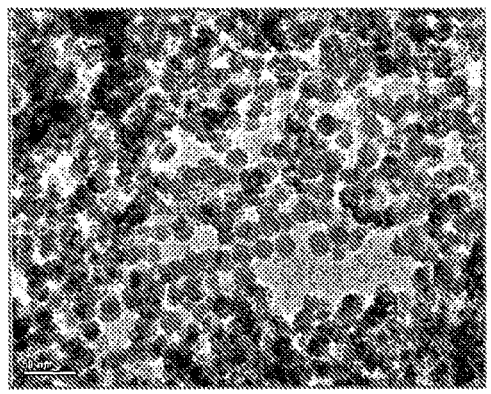
FIG. 8 shows TEM micrographs illustrating particle growth by sequential addition of TMOS: a) core (22 nm), b) 1st addition of 1.2 mmol of TMOS (27 nm), c) 2nd addition (31 nm), d) 3rd addition (33 nm), e) 4th addition (36 nm)
Figure 8B:
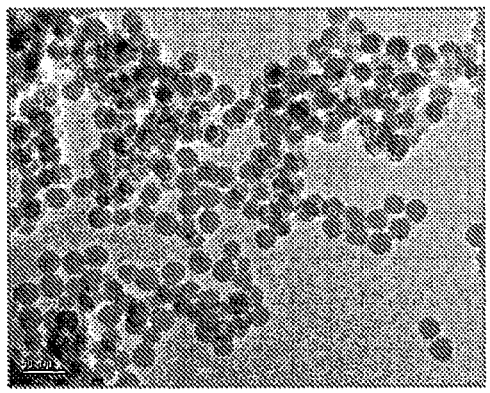
Figure 8C:
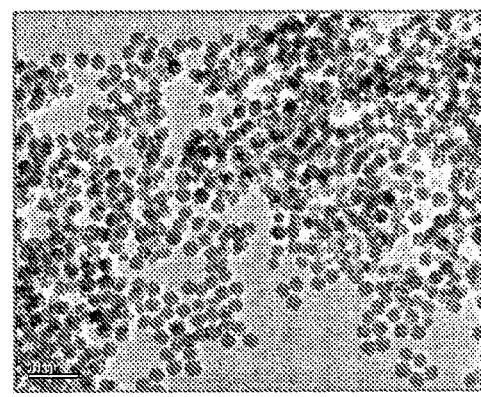
Figure 8D:
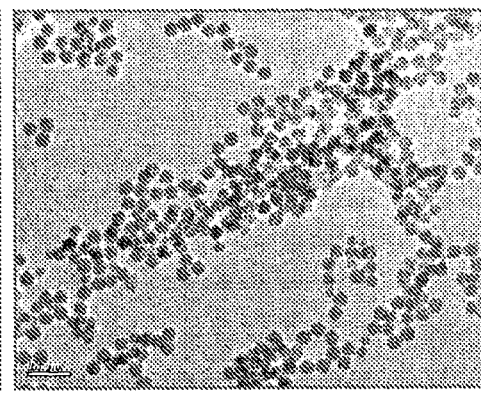
Figure 8E:
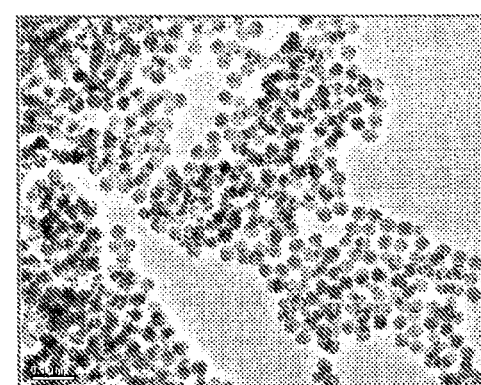
Figure 9A:
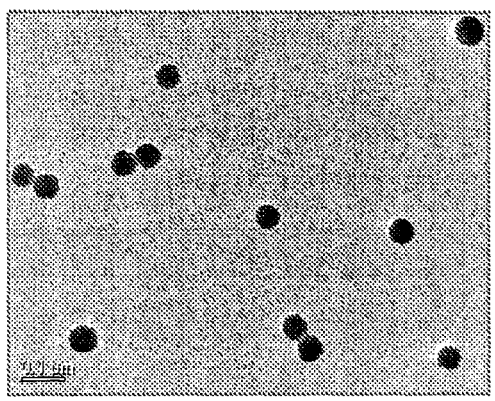
FIG. 9 shows TEM micrographs illustrating particle growth by sequential addition of TEOS: a) core (50 nm), b) 1st addition of 1.2 mmol of TMOS (83-92 nm), c) 2nd addition (91-106 nm), d) 3rd addition (102-120 nm), e) 4th addition (108-129 nm), f) 5th addition (128-146 nm)
Figure 9B:
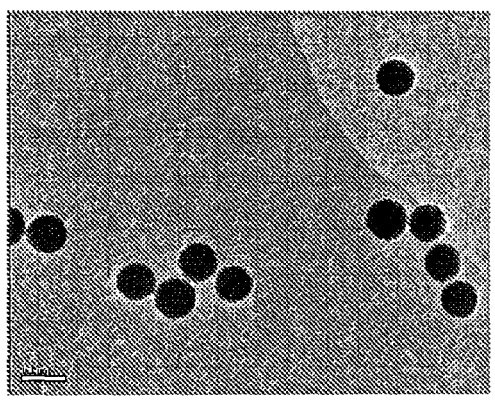
Figure 9C:
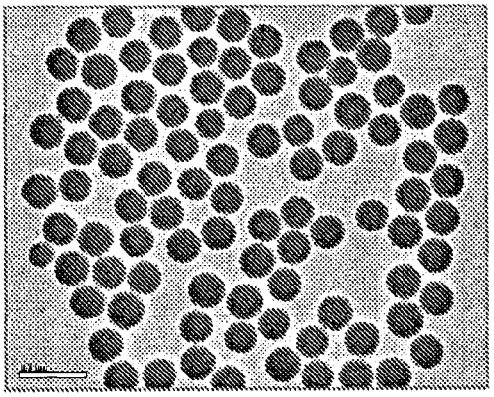
Figure 9D:
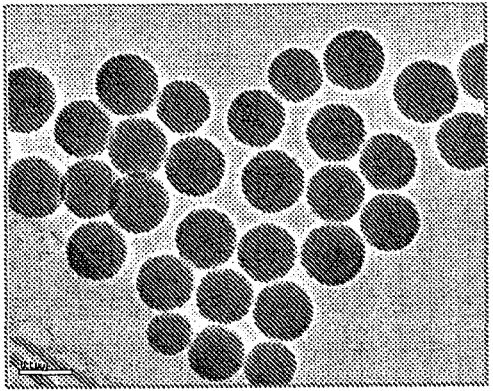
Figure 9E:
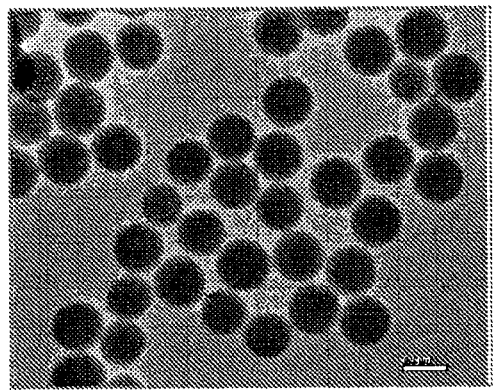
Figure 9F:
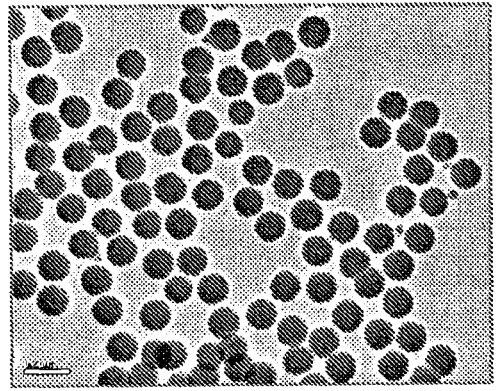

The following three systems show the influence of the water to alkoxide ratio on the size of the core. The corresponding TEM micrographs are presented in FIG. 7.

System 1: NP-5: 0.2 mol/L; cyclohexane 50 mL; catalyst: 1.333 mol/L $NH_4OH$ (pH~11.86); TMOS: 3 mmol; $[H_2O]/[TMOS]=20$, $[H_2O]/[NP-5]=6$; ageing 24 hrs. Particle diameter: 7.6 nm.

System 2: NP-9: 0.2 mol/L; cyclohexane 30 mL, catalyst: 1.333 mol/L $NH_4OH$ (pH~11.86); [NP-9]/[1-pentanol]=1, TMOS: 1.2 mmol; $[H_2O]/[TMOS]=30$, $[H_2O]/[NP-9]=6$; ageing 24 hrs. Particle diameter: ~20 nm.

System 3: Triton X-100: 23.9 wt. %; Toluene: 71.4 wt. %; Water: 4.7 wt. % (5 g); catalyst: 1.333 mol/L $NH_4OH$; TMOS: 8 mmol, $[H_2O]/[TMOS]=34.7$. Particle diameter: ~25 nm.

Particle Growth by Sequential Addition of Precursors (without Extra Emulsion)

Two experiments were conducted using TMOS and TEOS as silicon precursors.

Experiment 1

NP-9: 0.2 mol/L; cyclohexane 50 mL; catalyst: 1.333 mol/L $NH_4OH$; [NP-9]/[1-pentanol]=1, $[H_2O]/[NP-9]=6$. Particle size increases gradually by sequentially adding extra silicon precursor, the growth process is from FIG. 2. The results are displays in series in FIG. 8.

Experiment 2

NP-9: 0.2 mol/L; cyclohexane 30 mL; catalyst: 1.333 mol/L $NH_4O$; [NP-9]/[1-pentanol]=1, $[H_2O]/[NP-9]=6$. Instead of using TMOS, TEOS is used as silicon precursor, TEM images are shown in FIG. 9.

Although it is clear, from the TEM micrographs, that TEOS provides a significantly more important particle growth than TMOS, it is necessary to consider the quantity added in both cases as well as the size of the initial core. In the case of TMOS, the initial core was 22 nm and the average quantity added per cycle was 1.2 mmol to reach an average diameter of 36 after 4 additions. This represent a growth of 3 nm per cycle or 2.5 nm growth per mmol of TMOS added. In contrast, the initial core for TEOS is 50 nm and the average diameter after 5 addition of a total value of 15.6 mmol is 137 nm. This represents a growth of 5.6 nm per mmol of TEOS added. This difference in growth rate may be explained by the difference in the number of nuclei (i.e. core particles) present in both cases. If all the silicon alkoxide is converted into silica, for an equivalent amount of silica the number of the smaller cores observed in the TMOS synthesis should be larger than the number of the larger cores observed in the TEOS synthesis. In fact the difference in core particle population should be inversely proportional to their size since the total volume of silica is constant. Furthermore, for an equivalent addition of silicon alkoxide, if the number of core particles to be coated is twice as large, the increase in the core-shell size would be expected to be approximately twice as small. Hence, the smaller growth observed for the TMOS.

Importance of the Choice of the Microemulsion System

NP-9 was selected for producing microemulsion during the entire particle growing process. It is generally believed that increasing the alcohol concentration leads to the gradual increase of the polydispersity of particles, as the microemulsion phase diagram is sensitive to the alcohol content. This limits the maximum concentration of alkoxide precursor totally added since this precursor produces alcohol during its hydrolysis. The microemulsion with NP-9 as surfactant is less sensitive to alcohol content, thus higher concentration of alkoxide precursor may be utilised during the particle growth process. The presence of 1-pentanol as a cosurfactant makes the reverse micelles more rigid, and thus changes the microemulsion from unstable to stable, and also improves the uniformity of micelle size and subsequently the solid particle size. In addition, NP-9 microemulsions permit higher [water]/[surfactant] values, thus enabling the production of larger particles while maintaining the stability of microemulsion and the uniformity of particle size.

Particle Growth by Sequential Addition of Microemulsion and Silicon Alkoxide

Although it is possible to grow the particles by sequential addition of alkoxide precursor, the particle growth is limited to some extent by the limited supply of free water in the micelle core. In addition, in this method, the active molecules can only be loaded in core of the particles.

Figure 10:
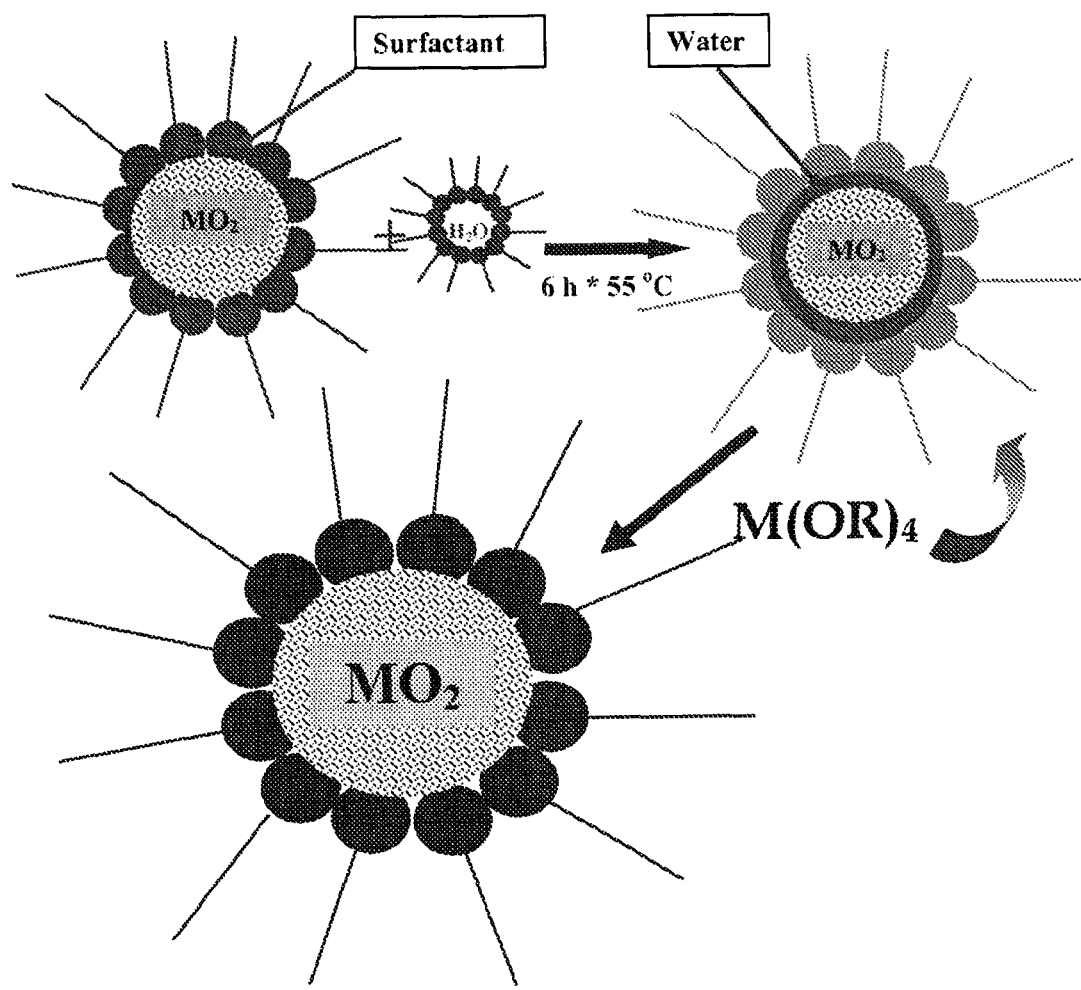
FIG. 10 shows a schematic diagram illustrating the principle of the novel growth process.

The alternative process, described in the present specification, consists in providing an additional supply of water, in the form of additional micro-emulsion, to sustain the alkoxide hydrolysis and condensation, and thus particle growth. A schematic representation of the process is provided in FIG. 10. Once the seed (core) particle is produced, a fresh microemulsion is added to the suspension of seeds (core particles). During the mixing, newly added water droplets from the fresh microemulsion coalesce with the hydrophilic droplets containing the seed particles, and the water adsorbs at the surface of the existing core particles. Upon addition of alkoxide precursor, it reacts with the water adsorbed at the particle surface, hydrolyses and then condenses with the hydroxyl groups present at the particle surface. If the alkoxide concentration is kept below a certain level, the concentration of silicon precursor remains below the supersaturation level and no extra nuclei are formed. The particles grow gradually by a classical monomer to nuclei addition. Examples of particle grown using this method are presented in FIG. 5.

The addition of water, in the form of a micro-emulsion at each cycle enables the introduction of active molecule at different stages with different concentration. This leads to the possibility of encapsulating more than one type of active molecule in different locations inside the ceramic nano-particles. The species in outer shells can then be released earlier than the molecules located inside the core or inner shells.

Figure 11A:
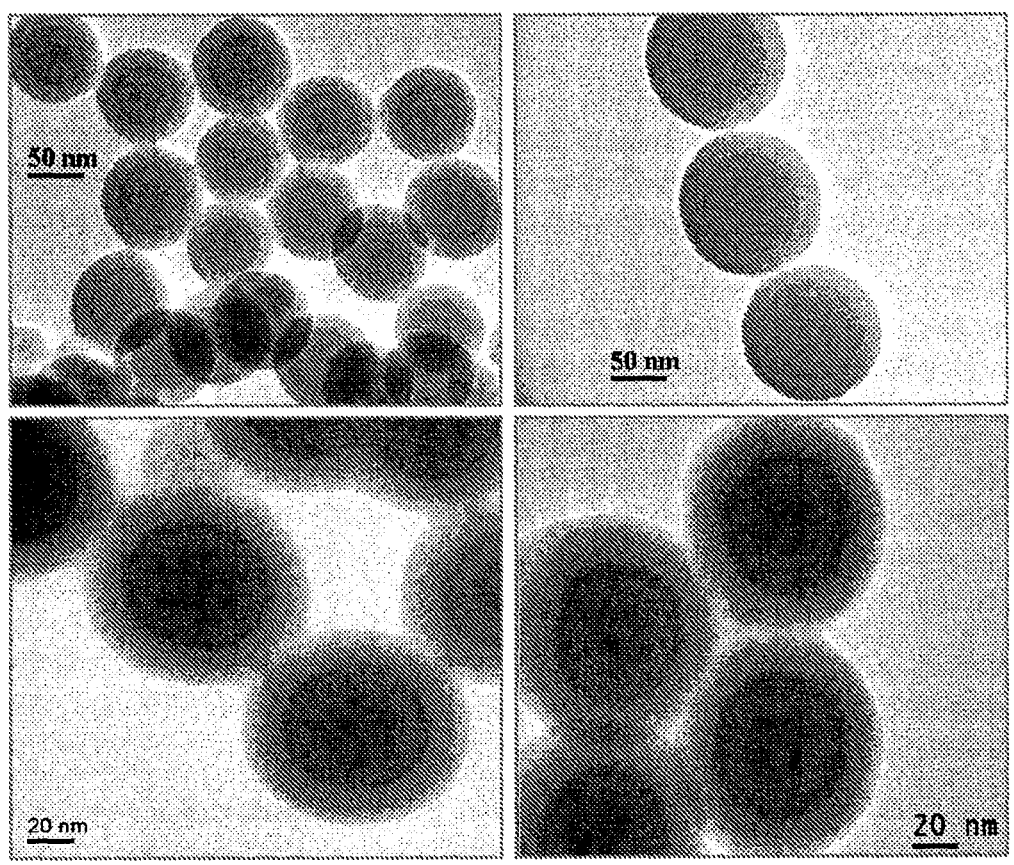
FIG. 11-$a$ shows a TEM micrograph of core-shell structure having: a) a bright field image (dark areas indicate heavier elements)
Figure 11B:
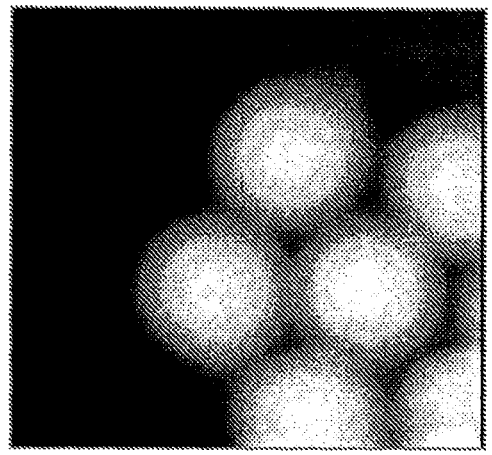
Figure 12A:
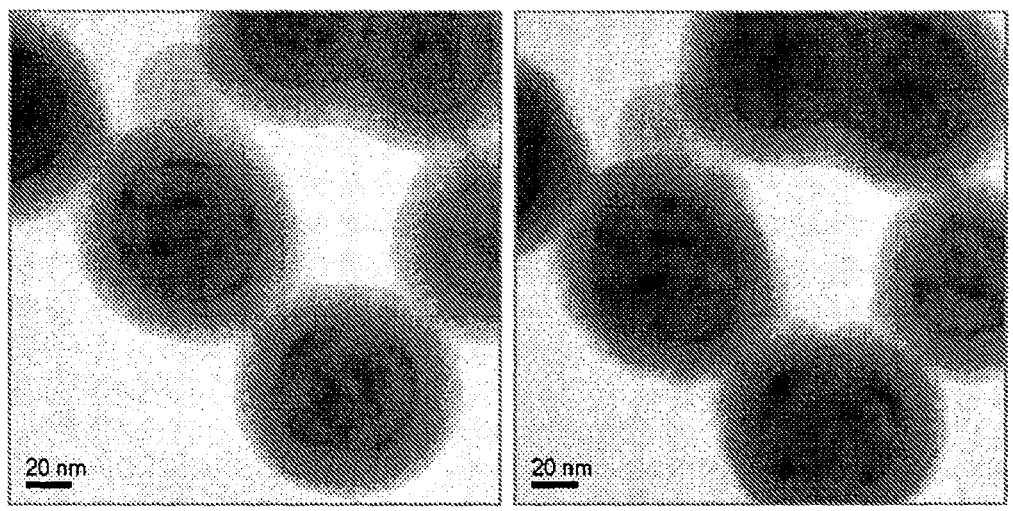
FIG. 12-$a$ shows a TEM micrograph of core-shell structure showing beam damage having: a) a bright field image, FIG. 12-$b$ shows a TEM micrographs of core-shell structure showing beam damage having: b) a dark field image after EDX line profile.
Figure 12B:
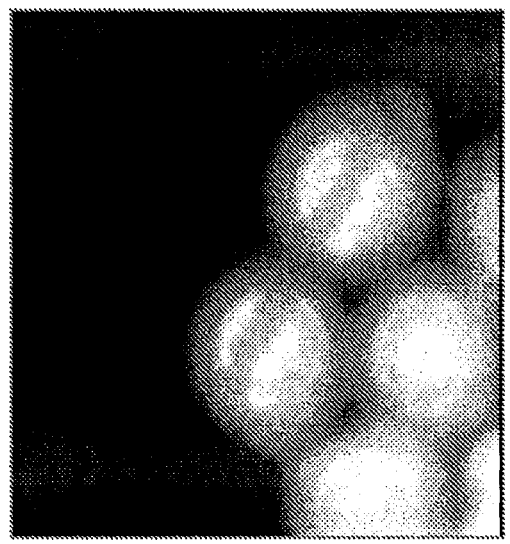

Some typical TEM images of these core-shell structures are shown in FIG. 11. Precise composition analysis of each shell using EDX line profile could not be performed as the electron beam damages the sample and leads to a redistribution of the metals inside the particles (see FIG. 12).

Using this synthesis procedure, monodispersed ceramic particles may be produced in the size range of 50-500 nm, commonly 10-300 nm. The final size of the ceramic particles depends on:
  (a) microemulsion properties including the type of surfactant, co-surfactant, solvent, water surfactant molar ratio, surfactant to co-surfactant molar ratio and pH of water pool;
  (b) type of alkoxide precursor and its concentration;
  (c) number of cycles;
  (d) amount of precursor added at each cycle; and
  (e) other sol-gel reactions conditions such as the temperature, pH etc.

Using the process of the present invention, layered nanoparticles may be produced as discussed above to produce silica particles in the presence of base (pH higher than 11). Using appropriate selection of conditions and reagents the synthesis condition may be shifted to neutral, weak acid, even medium to strong acid environment, possibly using other ceramic materials than silica.

Influence of Different Experimental Parameters on the Particles Polydispersity

Influence of the Method of Addition

Figure 13:
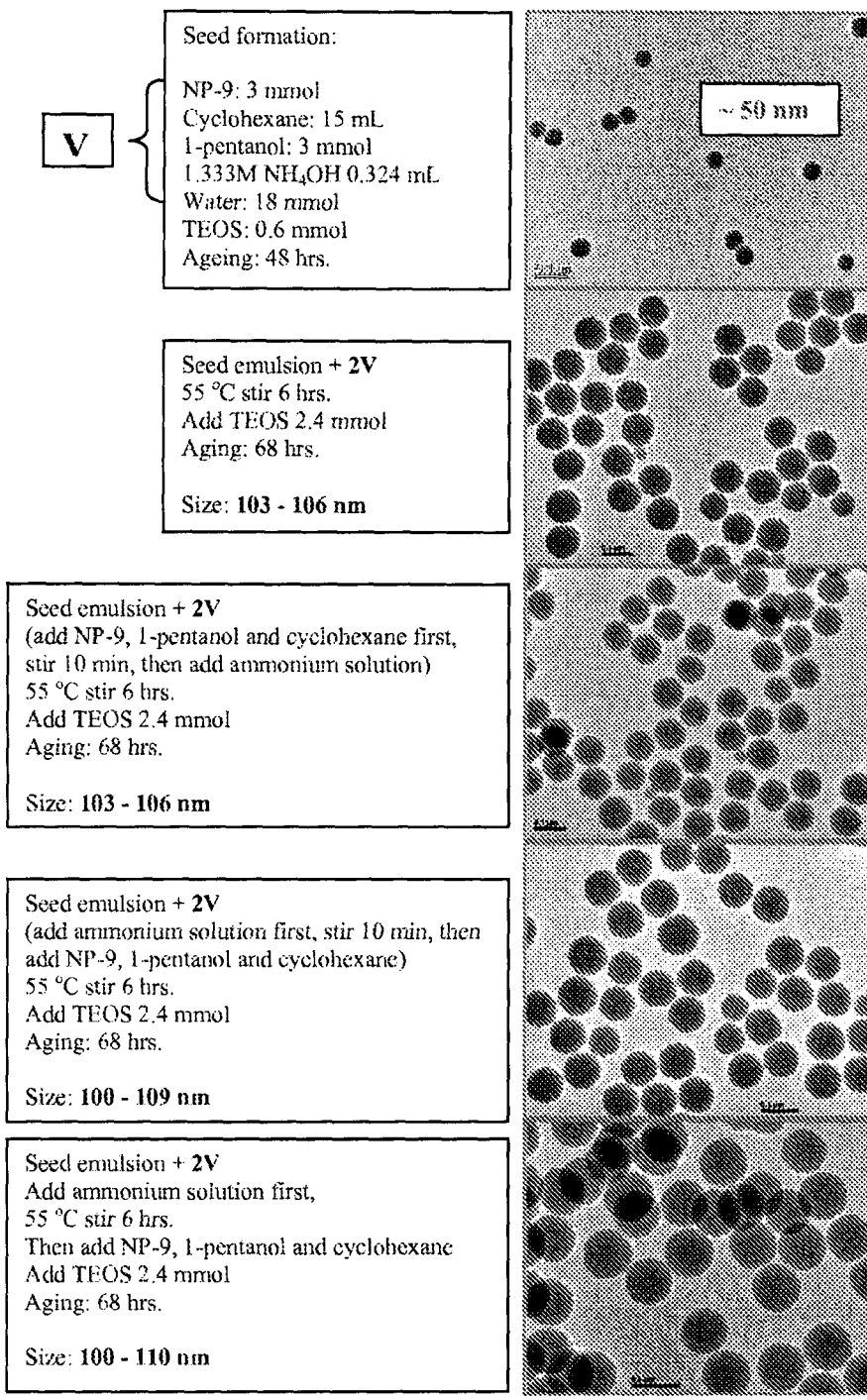
FIG. 13 shows micrographs illustrating the influence of the method of addition on the core-shell particle size.

FIG. 13 shows the different ways of adding the fresh microemulsion composition. The seeds were prepared by using the following system (NP-9 3 mmol, 15 ml of cyclohexane, 1 pentanol 3 mmol, 0.324 ml of $NH_4OH$ 1.33M, water 18 mmol, TEOS 0.6 mmol aged for 48 h). Additional microemulsion (double the volume of initially used for the seeds) and TEOS were then added as follows:

Addition of the micro emulsion, stirring at 55° C. for 6 hours and addition of TEOS followed by aging for 68 hours.
  Addition of the surfactant, 1 pentanol and cyclohexane first followed 10 minutes afterwards by the addition of the ammonia solution. Stirring at 55° C. for 6 hours and addition of TEOS followed by aging for 68 hours.
  Addition of the ammonia solution first followed 10 minutes afterwards by the addition of the surfactant, 1 pentanol and cyclohexane. Stirring at 55° C. for 6 hours and addition of TEOS followed by aging for 68 hours.
  Addition of the ammonia solution first followed by stirring at 55° C. for 6 hours. Then addition of the surfactant, 1 pentanol and cyclohexane followed by the addition of TEOS and aging of the suspension for 68 hours.

All the different methods produced particles with the same size. In all subsequent processes the last method was used.

Influence of the Number of Shells

Figure 14:
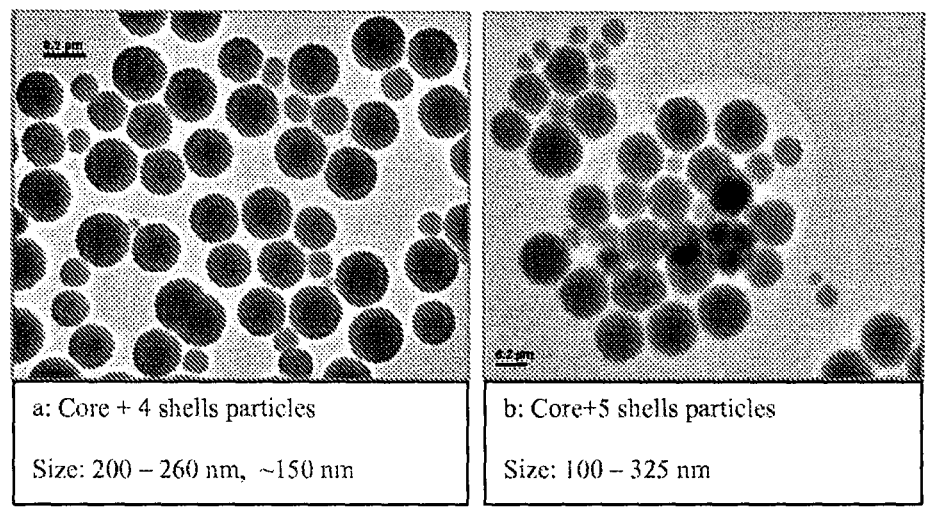
FIG. 14 shows TEM micrographs of particles synthesised using: a) 4 cycle (core+4 shells), and b) 5 cycle (core+5 shells)

To study the size limit on polydispersity, a suspension of 200 nm particles (i.e. core+3 shells) was split into two aliquots. One aliquot was heated to 55±5° C. while stirring for one hour. 2.592 mL of $NH_4OH$ 1.333 mol/L (pH~11.86) (equivalent water 144 mmol) was then added and the resulting mixture stirred for 6 hours at 55±5° C. 15.12 g of NP-9 (24 mmol), 2.608 mL of 1-pentanol (24 mmol), and 120 mL of cyclohexane were then added to the suspension. After stirring for 20 minutes, 2.184 mL TEOS (9.6 mmol) was added to the system which was further stirred for 48-72 hours. The particles were then washed, extracted and dried as described in Typical preparation for producing 50 nm silica core above. The TEM micrographs of the resulting particles (i.e. core+4 shells) are shown in FIG. 14-a. Using the same procedure particles with an extra shell (i.e. core+5 shells) were produced (see FIG. 14-b). FIG. 14 demonstrates that sequential growth beyond 200 nm leads to the production of polydispersed particles. FIG. 14-a reveals a bimodal distribution with in addition to the targeted 230 nm particles a few smaller ones with a size around 150 nm. One more iteration led to a polydisperse size distribution ranging from 100 nm to 325 nm. This gradual appearance of smaller particles suggests the formation of new silica nuclei resulting from incomplete coalescence of the added micro-emulsion with the droplets containing the particles. More generally, the larger the nanoparticles, the broader the size distribution. A possible way to the preserve monodispersity of large (>250 nm) particles may be fractionation by sedimentation and thus elimination of second generation (smaller) nanoparticles.

Another practical limitation, facing the sequential growth of large particles is the time necessary to complete the whole cycle. Typically to build three shells (i.e. 200 nm diameter) it may take 8-10 days. One way to decrease the processing time may be to increase the reaction temperature. Alternatively, using more hydrolysable alkoxide precursor may speed up the particle growth.

Influence of the Fresh Emulsion/Seed Emulsion Volume Ratio

Figure 15A:
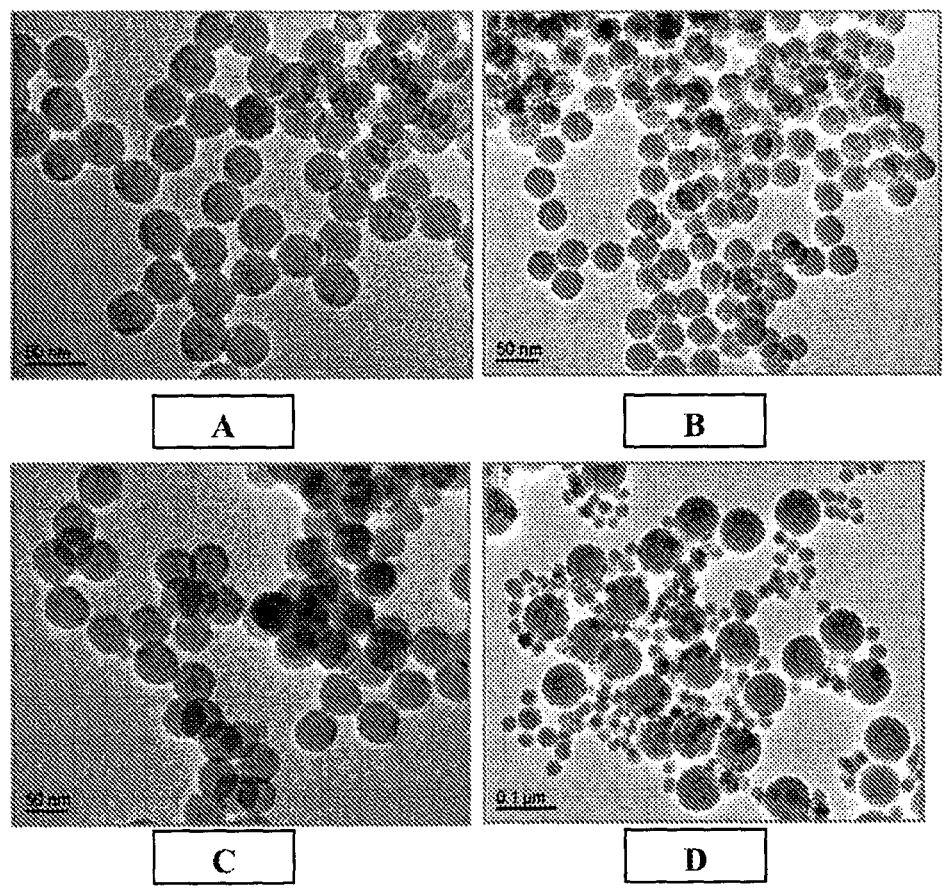
FIG. 15-$a$ shows TEM micrographs of particles grown using different dilution ratios, where the dilution rates (volume of fresh emulsion/volume of seed emulsion) were: A) 2, B) 3, C) 4, D) 5 for sample 1, silica core copper doped, the extra added aqueous phase 1.333 mol/L NH4OH, with Cu 10.14 mg/mL in the form of $Cu(NH_3)_4^{2+}$.
Figure 15B:
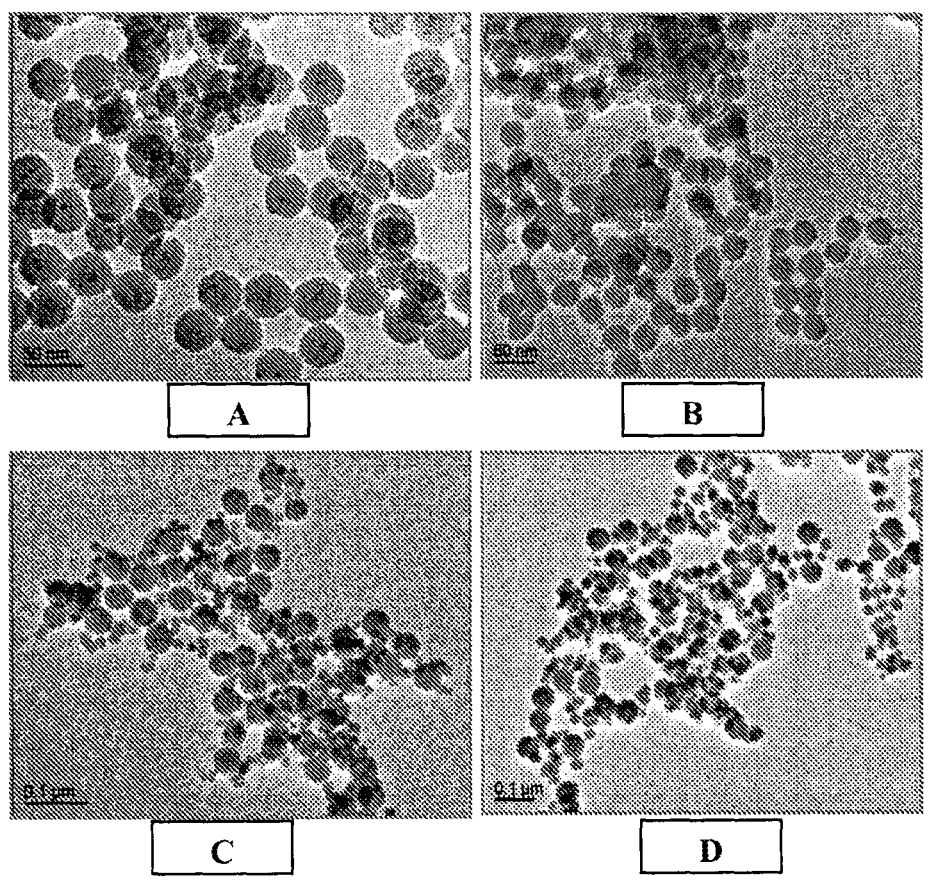

Experimental results (FIGS. 15 a and b) show that dilution of the seed emulsion with fresh microemulsion does not always lead to uniform particles. When the dilution (volume of fresh emulsion/volume of seed emulsion) is higher than 3, it produces polydispersed particles. This suggests that the amount of water that can be incorporated with existing particles cannot beyond certain value. If more water is added then new water-in-oil reverse micelle are formed and act as nucleation centres for the formation of new silica particles, resulting in the production of polydispersed particles.

Influence of the Mixing Method

Figure 16:
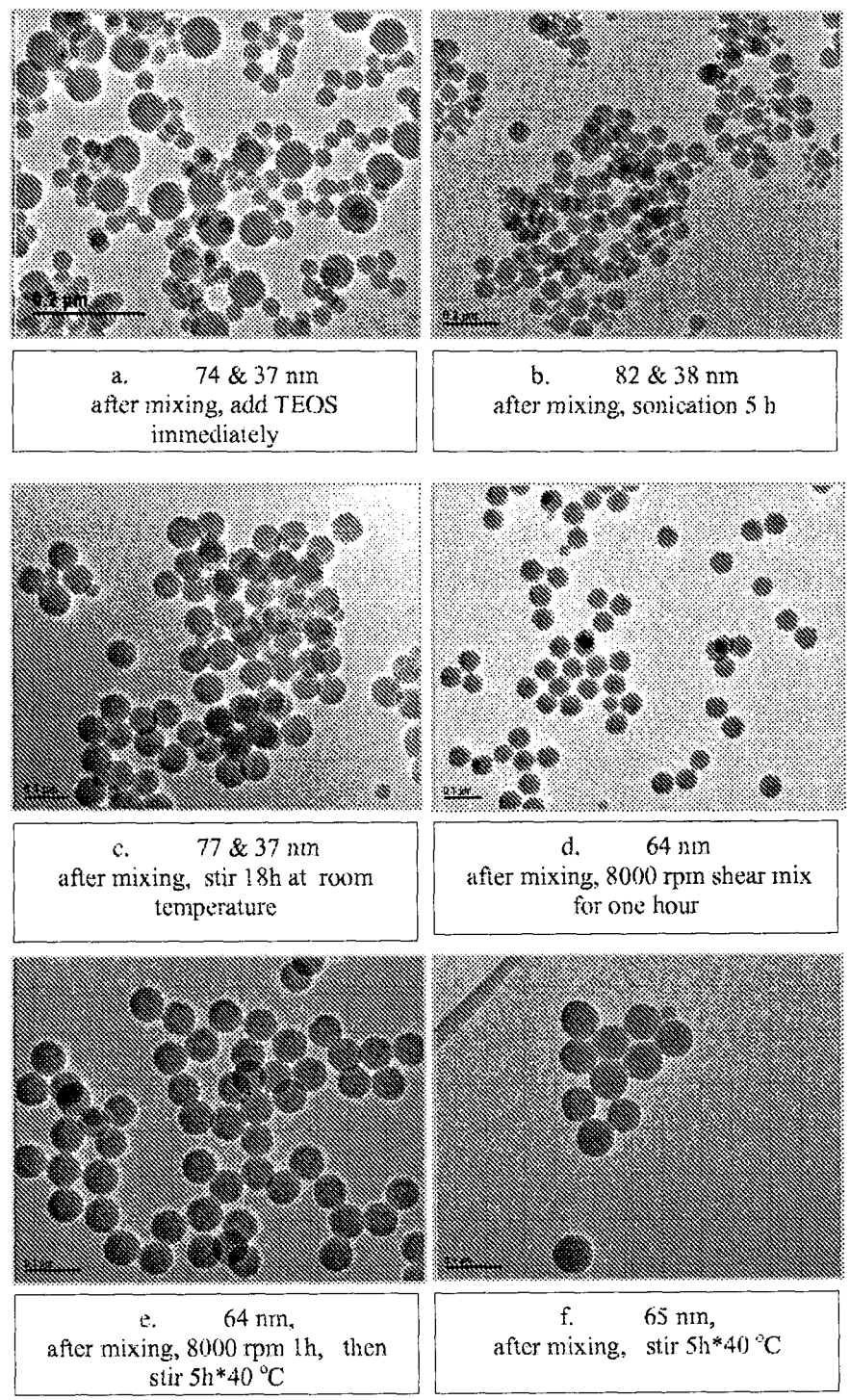
FIG. 16 shows TEM micrographs of particles prepared using different methods for mixing the seed emulsion and the fresh emulsion.

FIG. 16 shows the importance of the method used for mixing the emulsion containing the seed particles and the fresh microemulsion. A few different ways can be used to induce the coalescence of the fresh emulsion droplets with the existing droplets containing the seeds and thus ensuring the production of monodispersed particles. The first approach consists in shear mixing the resulting emulsion mixture at a very high shear rate (8000 rpm) to promote droplet collision and coalescence. The second approach relies on increasing the collision rate of the droplets by increasing the temperature of the mixed emulsion. It is important to note that, although theoretically full coalescence could be achieved at room temperature, the time required to achieve this make it impracticable, as demonstrated by the polydispersed sample obtained after 18 h stirring at room temperature. Sonication (even for long period of time) does not induce droplet coalescence as demonstrated by the bimodal distribution observed in FIG. 16-b.

Influence of the Silicon Precursor Reactivity

Figure 17:
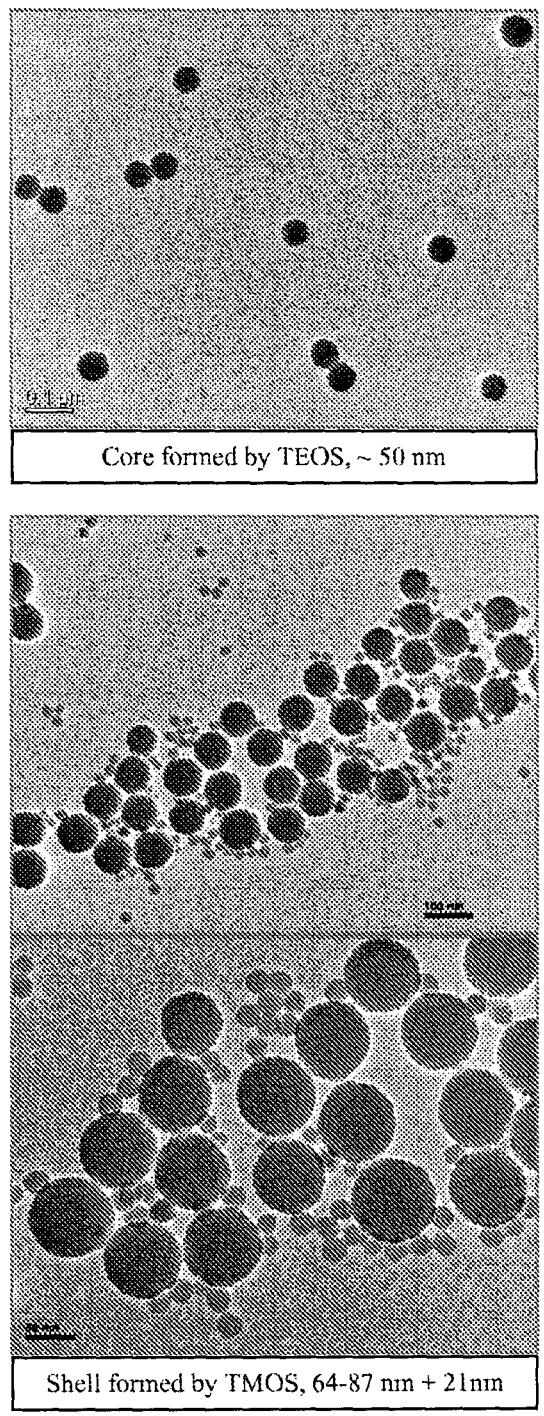
FIG. 17 shows TEM micrographs of particle cores formed using TEOS, and shells using TMOS (synthesis conditions identical to those used for FIG. 5)

As discussed earlier, a less reactive silica precursor such as TEOS produces bigger cores than more reactive precursor like TMOS. When TMOS is added in the same molar ratio as TEOS to the 50 nm pre-formed core particles, a bimodal distribution is obtained with 75 nm core-shell particles and smaller 21 nm secondary particles (see FIG. 17). The 21 nm particles correspond exactly to the core produced using TMOS (see FIG. 7-b). This suggests the presence of a secondary nucleation stage, which results from the concentration of hydrolysed TMOS reaching rapidly supersaturation and being relieved by secondary nucleation rather than condensation with the existing cores. In contrast, for the less reactive TEOS, the concentration of hydrolysed monomers rises more slowly and therefore they can be consumed by reaction with the core surface before their concentration reaches supersaturation and induces nucleation.

Organic Modified Silica (ORMOSIL) Core-Shell Structured Nanoparticles

Sol-gel synthesis in base leads to the production of mesoporous particles (i.e. large pore size: about 4 nm), which generally exhibit a rapid and uncontrolled release of their payload (typically organic dye or small drug molecules <2 nm). In order to keep the encapsulated molecules inside the ceramic nanoparticles and avoid leaching during the washing step, the ceramic matrix may be functionalised with active group (such as —$NH_2$, —SH, —COOH etc.), which will form a chemical bond with the encapsulated molecules. Using such a strategy, a fluorescent dye (fluorescein isothiocyanate (FITC)) has been successfully encapsulated in silica particles functionalised with amine groups (APTES). The release of the dye may then be triggered by screening or cleavage of the active molecule-matrix interaction.

Figure 18:
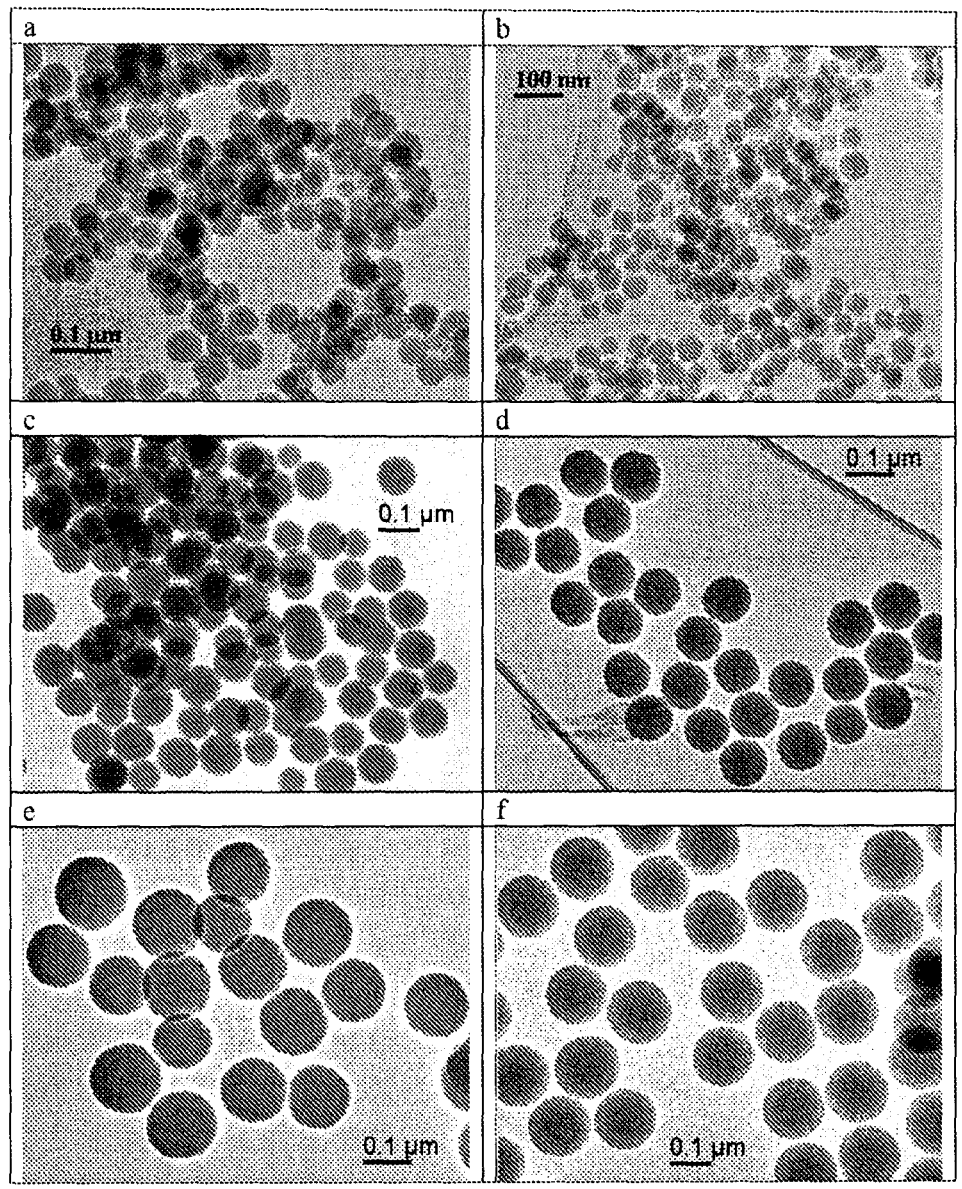
FIG. 18 shows TEM micrographs of silica core coated with Ormosil shell.

Layered nanoparticles were synthesised according to experimental conditions described earlier. The ORMOSIL is either integrated in the particle core or inside the second shell. The proportion of TEOS is either 75 mol % and 25 mol %. The ORMOSIL precursor used in these experiments is aminopropyltriethoxysilane (APTES). The corresponding TEM images are shown in FIG. 18 and the compositions of the ORMOSIL core-shell particles are displayed in Table 1.

Core-Shell Structured Nanoparticles Encapsulated with Two Active Molecules in Different Locations Another advantage of the present process is the possibility of encapsulating more than one dopant in the core particle or in any of the shells. Each molecule may be selectively encapsulated in different locations of the nanoparticles, and its concentration may also be controlled at each growth cycle. Not only is it possible to control the overall size by this process, but both the core size and the thickness of each shell may be tailored, thus potentially controlling the length of the release cycles as well as the different release rates. The following examples are aimed at demonstrating the versatility of this technique as well as the flexibility and control of the encapsulation process.

Figure 19:
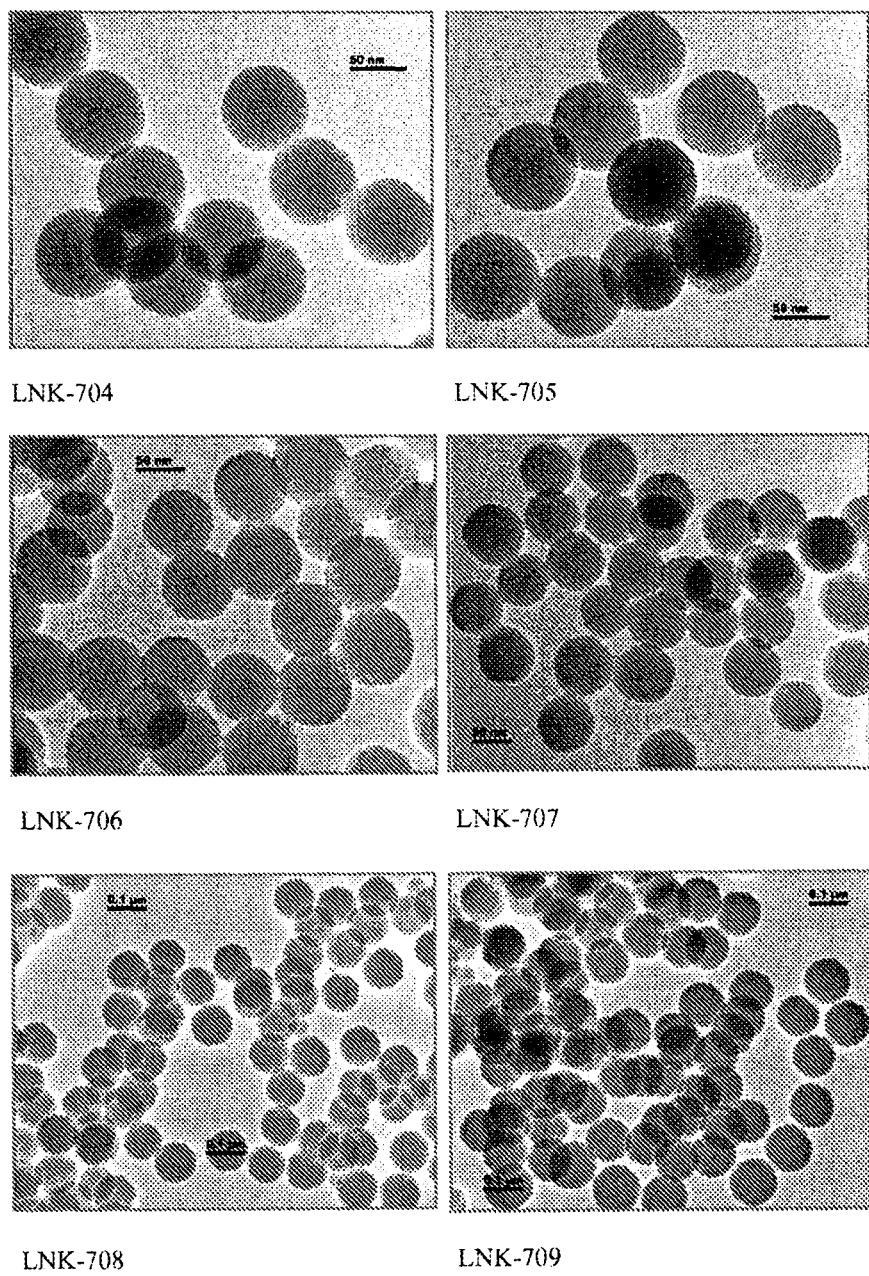
FIG. 19 shows TEM micrographs of samples with composition listed in Table 2.
Figure 20:
FIG. 20 shows photographs of samples with composition listed in Table 1 and suspended in acetone.
Figure 21:
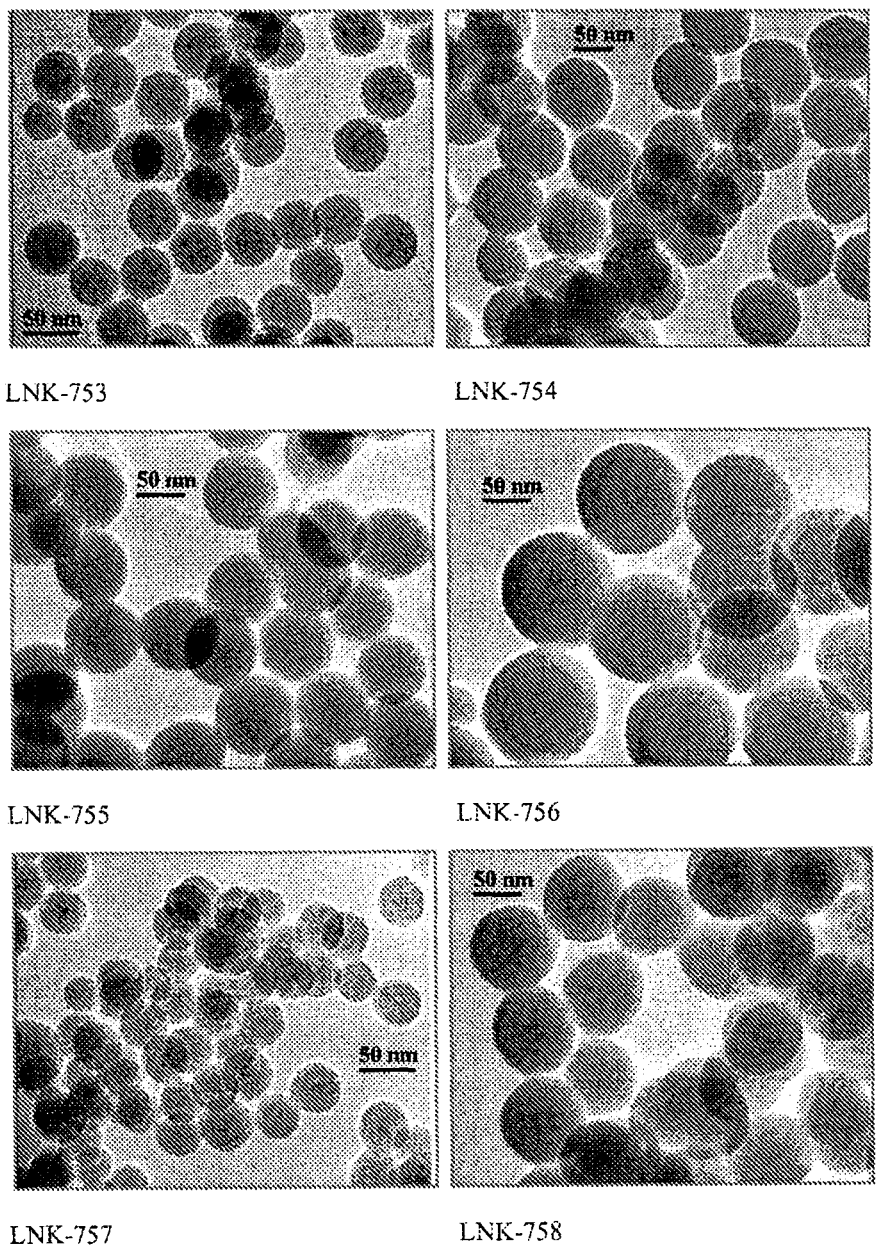
FIG. 21 shows TEM micrographs of samples with composition listed in Table 3.
Figure 21:
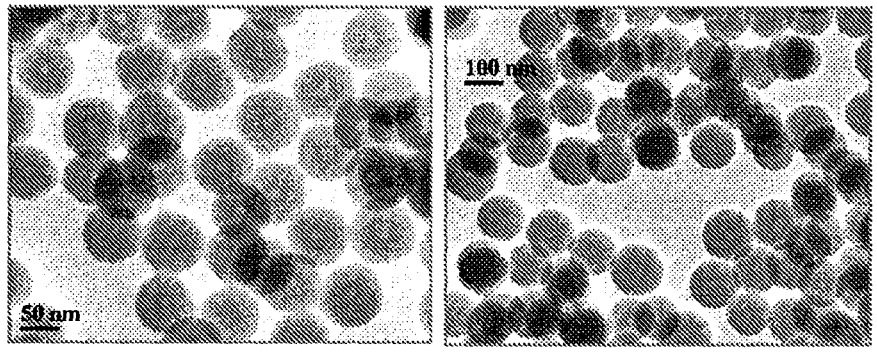
Figure 22:
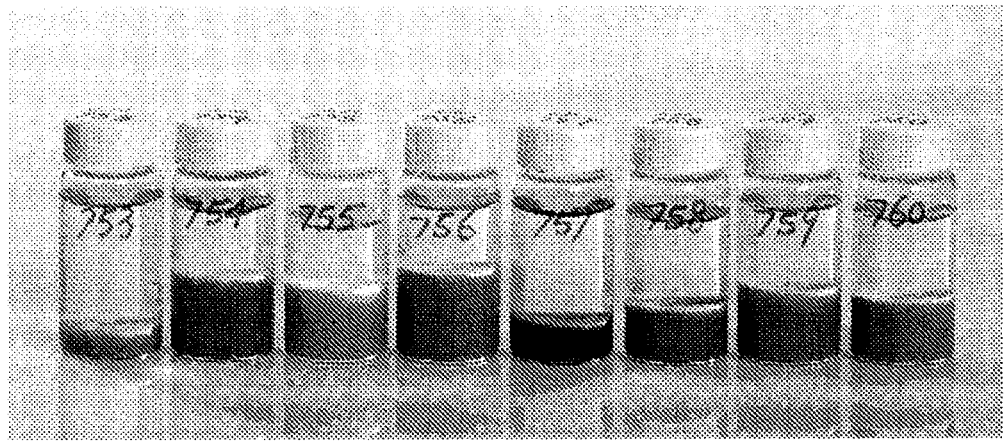
FIG. 22 shows photographs of sample with composition listed in Table 3 and suspended in acetone.
Figure 23A:
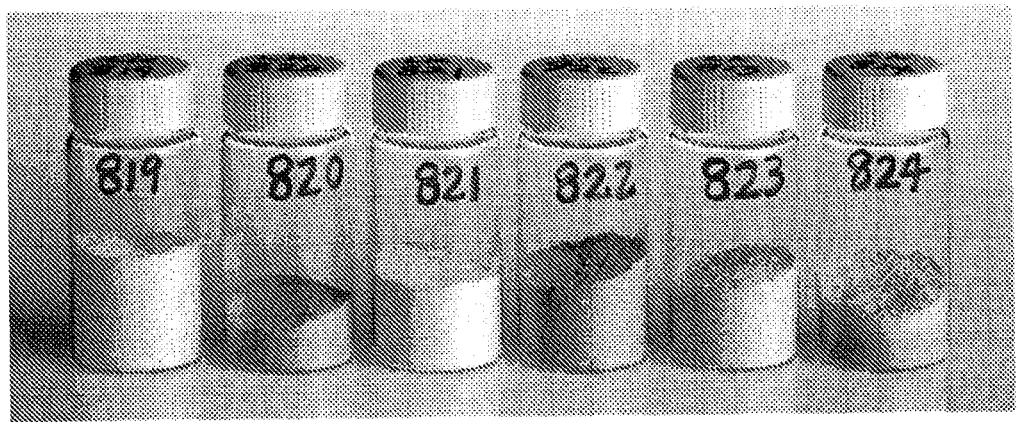
FIG. 23-$a$ shows photographs of samples with composition listed in Table 4 that is a) freeze-dried (SiO2/NaCl weight ratio: 15%)
Figure 23B:
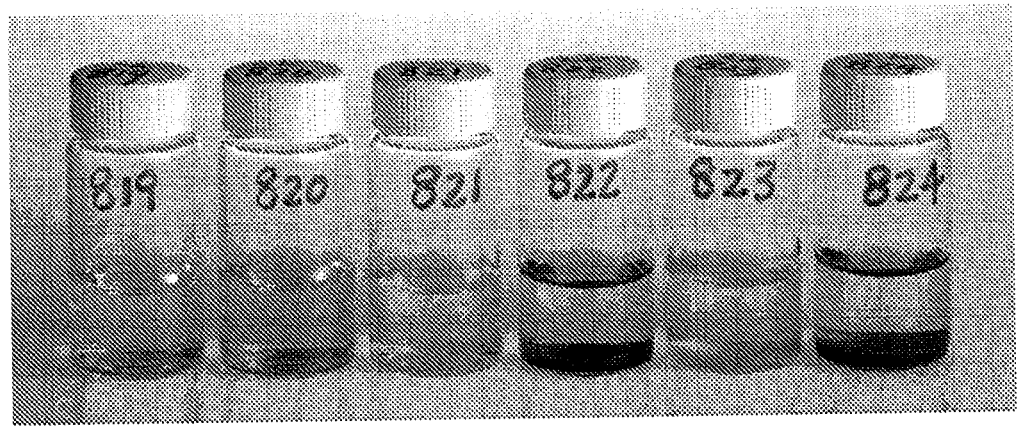

Table 2 lists the composition of different samples with $Cu(NH_3)_4^{2+}$ and $Ru(bPy)_3^{2+}$ doped in different location of the nanoparticles. The corresponding TEM images are presented in FIG. 19 and the photographs of the particles suspended in acetone are showed in FIG. 20. Table 3 lists the composition of different samples with $Cu(NH_3)_4^{2+}$ and $Co(NH_3)_6^{3+}$ doped in different location of the nanoparticles. The corresponding TEM images are presented in FIG. 21 and the photographs of the particles suspended in acetone are showed in FIG. 22. Table 4 lists the composition of different samples with $CuPC^{2-}$ and $Ru(bPy)_3^{2+}$ doped in different location of the nanoparticles. FIG. 23 shows the corresponding freeze-dried powders ($SiO_2$/NaCl weight ratio: 15%) and the particles resuspended in water.

TABLE 2

The components of product 1,
$Cu(NH_3)_4^{2+}$ and $Ru(bPy)_3^{2+}$ as dopants

| Sample | Core | Shell-1 | Shell-2 |
|---|---|---|---|
| LNK-704 | Cu: 10.82 mg<br>$SiO_2$: 72.00 mg | Ru: 3.24 mg<br>$SiO_2$: 288.00 mg | |
| LNK-705 | Ru: 1.62 mg<br>$SiO_2$: 72.00 mg | Cu: 21.63 mg<br>$SiO_2$: 288.00 mg | |
| LNK-706 | Cu: 10.82 mg<br>$SiO_2$: 72.00 mg | $SiO_2$: 288.00 mg | |
| LNK-707 | Ru: 1.62 mg<br>$SiO_2$: 72.00 mg | $SiO_2$: 288.00 mg | |
| LNK-708 | Cu: 10.82 mg<br>$SiO_2$: 72.00 mg | $SiO_2$: 288.00 mg | Ru: 6.48 mg<br>$SiO_2$: 576.00 mg |
| LNK-709 | Ru: 1.62 mg<br>$SiO_2$: 72.00 mg | $SiO_2$: 288.00 mg | Cu: 43.26 mg<br>$SiO_2$: 576.00 mg |

TABLE 1

The composition of ORMOSIL core-shell particles

| Image of FIG. 18 | Core | Shell-1 | Shell-2 | Diameter (nm) |
|---|---|---|---|---|
| Image-a | TEOS (100 mol. %) | | | 48-61 |
| Image-b | TEOS (75 mol. %)<br>APTES (25 mol. %) | | | 43-65 |
| Image-c | TEOS (75 mol. %)<br>APTES (25 mol. %) | TEOS (100 mol. %) | | 80-104 |
| Image-d | TEOS (100 mol. %) | TEOS (100 mol. %) | | 85-90 |
| Image-e | TEOS (75 mol. %)<br>APTES (25 mol. %) | TEOS (100 mol. %) | TEOS (100 mol. %) | 122-152 |
| Image-f | TEOS (100 mol. %) | TEOS (100 mol. %) | TEOS (75 mol. %)<br>APTES (25 mol. %) | 150-160 |

TABLE 3

The components and particle size of product 2,
$Cu(NH_3)_4^{2+}$ and $Co(NH_3)_6^{3+}$ as dopants.

| Sample | Core | Shell-1 | Shell-2 | Diameter |
|---|---|---|---|---|
| LNK-753 | Cu: 10.82 mg<br>$SiO_2$: 72.00 mg<br>$Cu/SiO_2$: 15 wt. % | | | 44-50 nm |
| LNK-754 | Cu: 10.82 mg<br>$SiO_2$: 72.00 mg<br>$Cu/SiO_2$: 15 wt. % | Co: 21.63 mg<br>$SiO_2$: 288.00 mg<br>$Co/SiO_2$: 7.5 wt. % | | 80-90 nm |
| LNK-755 | Cu: 10.82 mg<br>$SiO_2$: 72.00 mg<br>$Cu/SiO_2$: 15 wt. % | $SiO_2$: 288.00 mg | | 76-88 nm |
| LNK-756 | Cu: 10.82 mg<br>$SiO_2$: 72.00 mg<br>$Cu/SiO_2$: 15 wt. % | $SiO_2$: 288.00 mg | Co: 43.26 mg<br>$SiO_2$: 576.00 mg<br>$Co/SiO_2$: 7.5 wt. % | 102-132 nm |
| LNK-757 | Co: 10.82 mg<br>$SiO_2$: 72.00 mg<br>$Co/SiO_2$: 15 wt. % | | | 38-60 nm |
| LNK-758 | Co: 10.82 mg<br>$SiO_2$: 72.00 mg<br>$Co/SiO_2$: 15 wt. % | Cu: 21.63 mg<br>$SiO_2$: 288.00 mg<br>$Cu/SiO_2$: 7.5 wt. % | | 77-88 nm |
| LNK-759 | Co: 10.82 mg<br>$SiO_2$: 72.00 mg<br>$Co/SiO_2$: 15 wt. % | $SiO_2$: 288.00 mg | | 76-87 nm |
| LNK-760 | Co: 10.82 mg<br>$SiO_2$: 72.00 mg<br>$Co/SiO_2$: 15 wt. % | $SiO_2$: 288.00 mg | Cu: 43.26 mg<br>$SiO_2$: 576.00 mg<br>$Cu/SiO_2$: 7.5 wt. % | 104-135 nm |

TABLE 4

The components of product 3, $CuPC^{2-}$ and $Ru(bPy)_3^{2+}$ as dopants.

| Sample | Core | Shell-1 | Shell-2 |
|---|---|---|---|
| LNK-819 | Ru: 1.62 mg<br>$SiO_2$: 72.00 mg | $SiO_2$: 288.00 mg | |
| LNK-820 | CuPC: 3.24 mg<br>$SiO_2$: 72.00 mg | $SiO_2$: 288.00 mg | |
| LNK-821 | Ru: 1.62 mg<br>$SiO_2$: 72.00 mg | $SiO_2$: 288.00 mg | $SiO_2$: 576.00 mg |
| LNK-822 | Ru: 1.62 mg<br>$SiO_2$: 72.00 mg | $SiO_2$: 288.00 mg | CuPC: 12.96 mg<br>$SiO_2$: 576.00 mg |
| LNK-823 | CuPC: 3.24 mg<br>$SiO_2$: 72.00 mg | $SiO_2$: 288.00 mg | $SiO_2$: 576.00 mg |
| LNK-824 | CuPC: 3.24 mg<br>$SiO_2$: 72.00 mg | $SiO_2$: 288.00 mg | Ru: 6.48 mg<br>$SiO_2$: 576.00 mg |

Although as mentioned before, elemental analysis and probing is not possible due to electron beam damage, some clear core shell structure can be evidence by TEM. The presence of an "onion" type structure (see FIG. 21 b, d, e, f, g) confirms the possibility of selectively doping a specific shell with a specific dopant. The colour changes observed in FIGS. 20, 22 and 23 with dopants located in different layer of the nanoparticles further illustrates the potential of this technology for optical applications.

Encapsulation of Solid Core

An additional feature of the present invention is the ability to encapsulate solid particles inside a shell of metal oxide. The core may be any species of powder such as metal oxide, semiconductor, quantum dot, magnetic particles or crystalline particles.

The shell(s) may comprise one metal oxide or a more than one different metal oxides, mixed metal oxides or metal oxide containing a dopant. An example of the preparation and encapsulation of crystalline $In_2O_3$ nanocrystals inside silica shell is detailed below.

$In_2O_3$ nano crystals were prepared as follows: 1.017 g $InCl_3$ was dissolved in 10 mL of pure water. 10 mL of $NH_4OH$ 10M was added dropwise to the solution while stirring and a precipitate was formed. $Cl^-$ and $NH_4^+$ ions were remove by successive washing (5-10 times with 50 mL of water each time) until no smell of ammonia was detectable. 0.92 mL $HNO_3$ (1M) was then added to peptise the precipitate and the suspension stirred overnight at 55±5° C. A further 0.45 mL of $HNO_3$ 1 mol/L was added and the suspension stirred again overnight at 55±5° C. The final pH was measured at 2.284 and the TEM showed 50 nm*10 nm crystallites with well defined facets.

The crystals were then coated using the following method. A solution A containing 6 mmol of NP-9, 6 mmol of 1-pentanol, 30 mL of cyclohexane, 0.972 mL of $NH_4OH$ 6.667 mol/L, was stirred until clear.

A solution B containing 6 mmol of NP-9, 6 mmol of 1-pentanol, 30 mL of cyclohexane, 0.324 mL of the $In_2O_3$ nanocrystals in suspension was stirred until clear.

Figure 24:
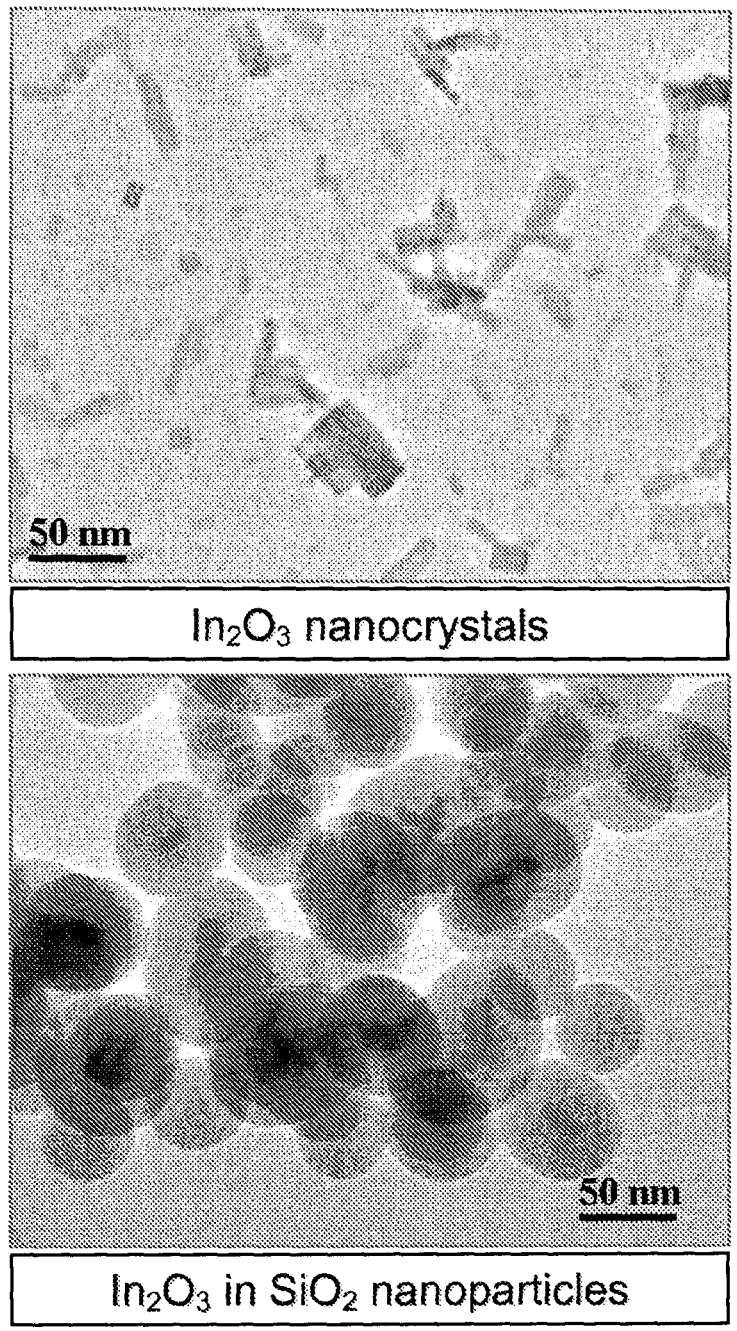
FIG. 24 shows photomicrographs of $In_2O_3$ nanocrystals in suspension and coated with silica shell.

The two solutions A and B were mixed together and 2.4 mmol of TEOS added to the mixture. The solution was aged for 72 hrs. 50 ml of dry acetone was then added to the resulting suspension to destabilise the microemulsion and recover the particles. The particles were washed several times with acetone and examined by TEM (see FIG. 24). The TEM micrographs clearly demonstrated the encapsulation of the 50 nm rods inside silica nano-particles Encapsulation of a Radioactive Tracer in the Core or Shell The encapsulation of chelated species such as In-DTPA and Ga-DTPA in any selected locations (core or selected shell) of silica particles has been successfully achieved. The metal content as analysed by EDS was typically 1-2 wt % of the silica. The particle size and size distribution were found to be independent of the presence or absence of dopants. This confirms the ability to exercise independent control over particle size and internal structure achieved by the process of the present invention.

Radioactive tracers such as $^{67}$Ga-DTPA may also be easily doped inside silica nanoparticles, thus producing particles that are traceable in vivo. Such particles were prepared by the following procedure. $^{67}GaCl_3$ ($t_{1/2}$: 3.261 days) was received from ANSTO-Cyclotron with activity 2 GBq/mL in 0.1 mol/L HCl solution. The solution was diluted 1 in 10 with water. 0.428 mL of concentrated ammonia (25 wt. % $NH_3$) containing DTPA 3.9 mg/l was added to 0.22 mL $^{67}GaCl_3$ solution at pH about 2.

The resulting solution may be used as the aqueous solution in the processes described earlier to produce particle with either active gallium in the core, in the outside shell or throughout the whole particle. These particles may be used in biodistribution studies to investigate the location of silica particles in rats using gamma counting as a detection method. Potential application of such nanoparticles may be envisaged both in radiotherapy and radio-imaging.

Release from Core-Shell Particles

As mentioned previously, base catalysed sol-gel synthesis leads to the production of mesoporous particles (i.e. about 4 nm), which generally exhibit a rapid and uncontrolled release of their payload. The notable exception to this is the encapsulation of organometallic complexes, which may exhibit some interaction between metal cation and silica surface. In this case, the interaction of the surface with the complex ensures encapsulation and temporary locking of the molecule inside the silica nanoparticle structure. As the particles are suspended in aqueous phase, the strong affinity of the silica surface for water can gradually displaced the adsorption equilibrium with the active organometallic complex thus releasing the molecule out of the silica matrix. In most cases the release is achieved by gradual dissolution of the silica matrix.

Figure 25:
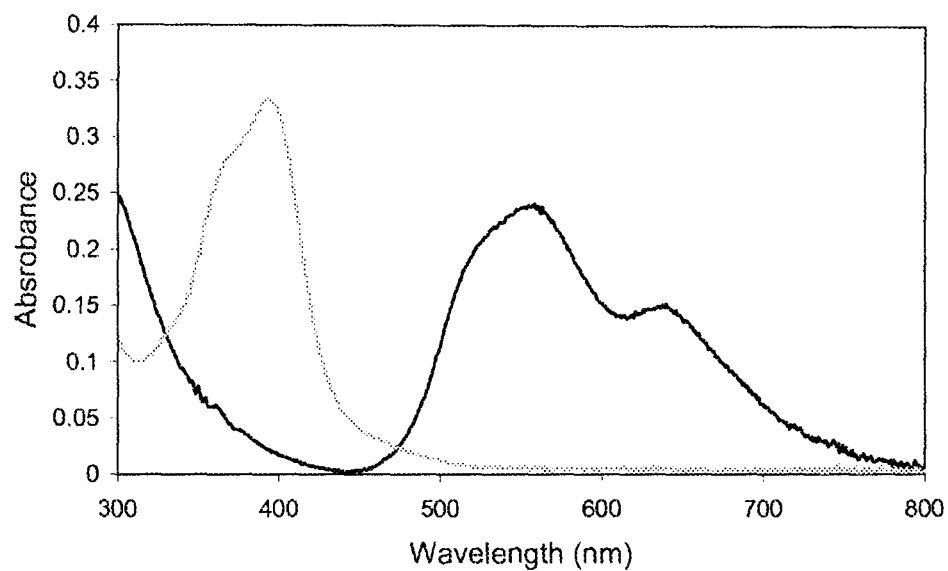
FIG. 25 shows UV-visible spectra of CuPC (black line, $\lambda_{max}$: 556 nm) and Rubpy (grey line, $\lambda_{max}$: 390 nm) in neutral water.
Figure 26:
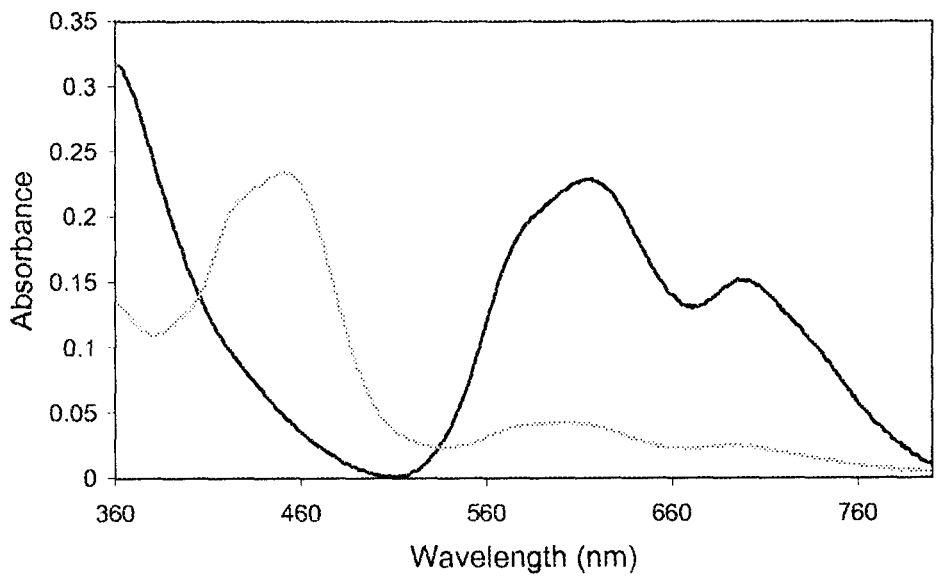
FIG. 26 shows UV-visible spectra of samples LNK-822 (black line, $\lambda_{max}$: 615 nm) and LNK-824 (grey line, $\lambda_{max}$: 450 nm) in SBF after 32 days.

To demonstrate the potential for sequential release, two sets of nanoparticles with different dopants in the core and outer shell were synthesized: a) sample LNK-822 with CuPC in the outer shell and Rubpy in the core, and b) sample LNK-824, with Rubpy in the outer shell and CuPC in the core. The release from those two samples was monitored using UV-vis spectrometry. A UV visible spectrum of the two dyes in water is shown in FIG. 25 and a spectrum of the two samples (LNK 822 and 824) after 32 days of leaching in SBF is shown in FIG. 26. The maximum absorption of CuPC is at 556 nm, and at 390 nm for Rubpy. The overlap between the two peaks is small and can thus be neglected in a first approximation. No shift in the maximum absorption wavelength (for CuPC and Rubpy) with pH is observed in the pH range of 1-12 (corresponding to the particle synthesis range). A red shift of approximately 60 nm is observed for both dyes, from 390 nm to 450 nm for Rubpy and 556 nm to 615 nm for CuPC when the media changes to SBF (see FIG. 26). In sample LNK-824, a slight absorption can be seen in around 615 nm suggesting there is slight amount of CuPC released as there is no absorption for Rubpy at that region. However, due to the existence of slight absorption of CuPC at 450 nm, it is hard to quantify the Rubpy release, especially for such a small amount.

Figure 27A:
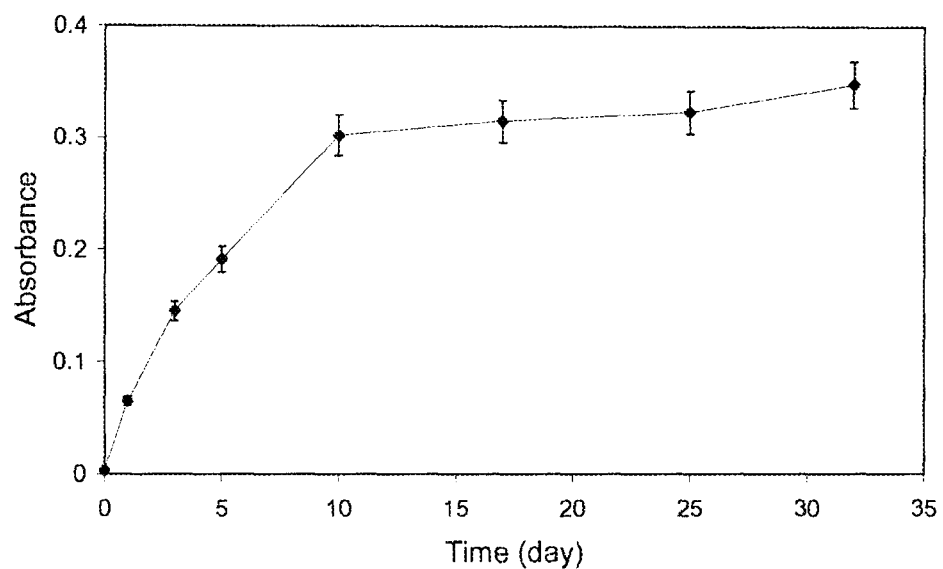
FIG. 27-$a$ shows a release rate curve of a) Sample LNK-822 (1.022 g of freeze dried powder in 20 mL SBF at 37° C., max=615 nm.
Figure 27B:
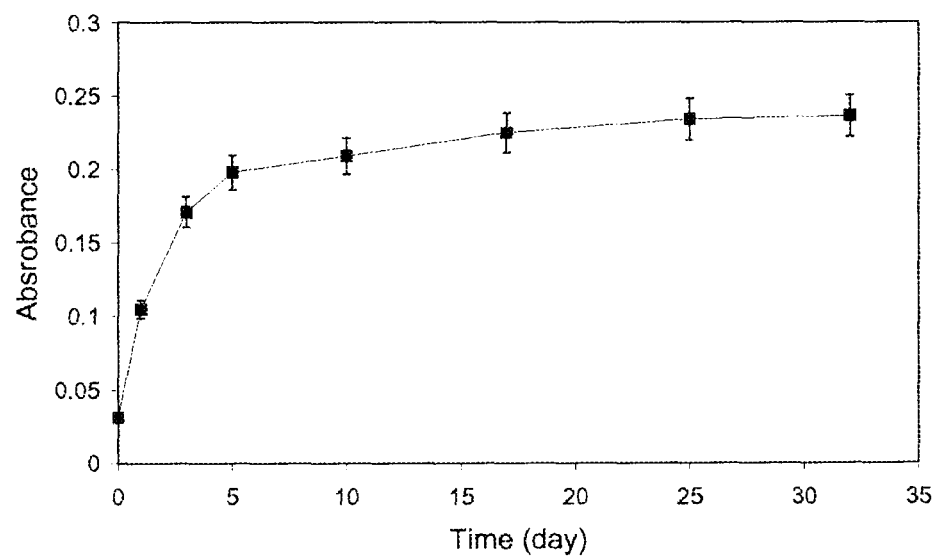

The corresponding release curves for the two core shell particles are shown in FIG. 27. When CuPC was encapsulated in the outer shell, it was released gradually in 10 days. After that time, a constant concentration of CuPC for a few days was observed suggesting that most of dye had been released. A very small amount of the Rubpy from the core was also released although the exact amount is not easily quantifiable. Interestingly, the colour of LNK-822, which was green initially (see FIG. 23), turned to orange (i.e. the colour of Rubpy doped nanoparticles) after release of CuPC from the outer shell, thus confirming visually the sequential release of the CuPC. On the other hand, when Rubpy was doped in the outer shell and CuPC was in core (LNK824) the release curve displays that in 5 days most of Rubpy was leached. No detectable leaching of CuPC from core was observed. During the leaching, the colour of particles changed from yellow to green/blue (the original colour of the particles containing only CuPC). These experiments confirm the potential use of these multilayered particles for sequential release applications.

When no strong interaction between the molecule and the silica pore surface is present, the ceramic matrix may be functionalised with active groups (such as —$NH_2$, —SH, —COOH etc.), which can form a chemical bond with the encapsulated molecules. Using such a strategy, a fluorescent dye (fluorescein isothiocyanate (FITC)) has been encapsulated in silica particles functionalised with amine groups (APTES). The release could then be triggered by screening or cleavage of the active molecule-matrix interaction. Another possibility to encapsulate small molecules inside the mesoporous particles is to conjugate them with larger molecules such as dextran or a dendrimer prior to encapsulation.

The present invention provides a process for manufacture layered nanoparticles, with core-shell structures and which contain one or more active molecules or dopants encapsulated in different locations (i.e. shells or layers) of the nanoparticles. Advantages of the technology include the ability to control precisely the overall particle size, core size, shell thickness, concentration of active species in each shell, as well as the release sequence and release rate of each encapsulated dopant.

The inventors have demonstrated that small organometallic molecules can be encapsulated inside the particles. These molecules include metal complex compound (e.g. copper tetramine, cobalt hexamine, indium-DTPA, gallium-DTPA), inorganic dye such as Rubpy [(tris(2,2'-bipyridyl)dichlororuthenium(II) hexahydrate], CuPC [copper (II) phthalocyanine-tetrasulfonic acid tetrasodium salt], and fluorescence dye FITC (fluorescein isothiocyanate). Even complex objects such as $In_2O_3$ nanocrystals may be encapsulated. More importantly, the inventors have shown that it is possible to encapsulate more than one dopant at different locations inside the nanoparticles with different loading value. The nanoparticle structure i.e. core size and layer thicknesses may be precisely controlled by the processing parameters such as the nature and quantity of precursor added. The monodispersity of the particles may be maintained throughout the growth process by ensuring that all the water added at each cycle migrates to the surface of the existing particles. Residual empty water droplets (i.e. not containing a particle) may act as secondary nucleation centers. Although the growth kinetics may be accelerated by increasing the amount of precursor, adding a catalyst or using less seed materials, polydispersity is introduced after the 4th cycle. Extreme dilution of the seed emulsion also leads to the production of polydispersed nanoparticles.

Although the nanoparticles produce by the present process are suitable for intravenous drug delivery, they may have application in information technology for high-density optical memory storage, specific optical sensors or biosensors, and in the protection/surface modification of nanoparticles from corrosion/oxidation, sintering and coalescence, change of surface properties (surface, charge, zeta potential, suspensibility), etc. In the long term, the technology may be employed to develop nanoparticles comprising core particles containing encapsulated active molecules coated by shell(s) comprising organic modified ceramic precursor exhibiting functional group like —$NH_2$, —SH, —COOH, which may be easily functionalised by antibodies or peptides for active drug targeting application.

FIGS. 28*a* to 28*f* show diagrammatic representations of several different layered nanoparticles according to the present invention. It should be noted that these representations show only a few of the many different types of nanoparticle which may be made according to the invention, and that the particular methods for using the nanoparticles are by way of example only. Other types of particles and methods for using them are possible and are envisaged in the present specification. Thus the descriptions below are to be taken as examples only, and are not to be taken in any way as being limiting with respect to the scope of the invention.

Figure 28A:
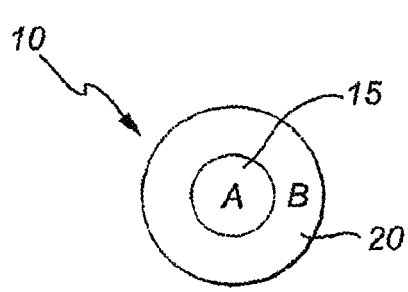
FIG. 28$a$ shows a diagrammatic representation of an embodiment of layered nanoparticles according to the present invention.

With reference to FIG. 28a, layered nanoparticle 10 comprises porous core particle 15 comprising first releasable dopant A and a porous layer 20 comprising second releasable dopant B surrounding core particle 15. When nanoparticle 10 is place in a suitable liquid environment, releasable dopant B is released first from nanoparticle 10, and then releasable dopant A is released. The period of time over which dopant B is released may depend on the thickness of layer 20, and the period of time over which dopant A is released may depend on the thickness of layer 20 as well as the size of core particle 15. The release rates may be dependent on the nature of the dopants as well as the nature and pore size of core particle 15 and layer 20. Alternatively, if dopant A is a non-releasable dye, nanoparticle 10 will appear coloured by dopant A, and will release releasable dopant B. As a further alternative, if dopant B is a non-releasable dye and dopant A is a releasable dopant, then nanoparticle 10 will appear coloured by dopant B, and will release dopant A.

Figure 28B:
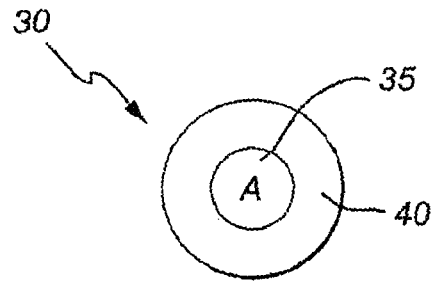

With reference to FIG. 28b, layered nanoparticle 30 comprises porous core particle 35 comprising releasable dopant A and porous layer 40 comprising no releasable dopant. Porous layer 40 surrounds core particle 35. When nanoparticle 30 is placed in a suitable liquid environment, releasable dopant A is released from nanoparticle 10 after a delay. The length of the delay depends on the thickness and porosity of porous layer 40.

Figure 28C:
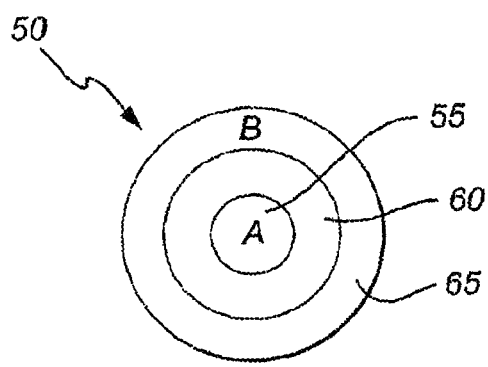

With reference to FIG. 28c, layered nanoparticle 50 comprises porous core particle 55 comprising first releasable dopant A, first porous layer 60 surrounding core particle 55 and second porous layer 65 surrounding first porous layer 60. First layer 60 comprises no releasable dopant and second porous layer 65 comprises second releasable dopant B. When nanoparticle 50 is placed in a suitable liquid environment, second releasable dopant B and first releasable dopant A are released sequentially, with a delay between release of dopants B and A. The length of the delay is dependent on the thickness and porosity of first layer 60.

Figure 28D:
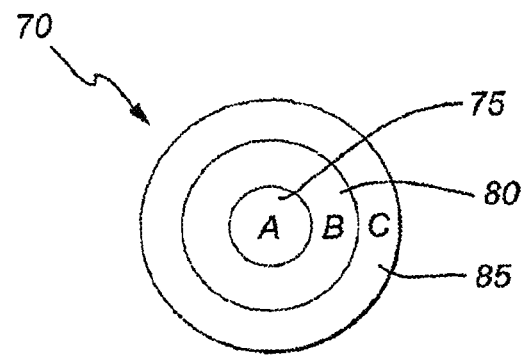

With reference to FIG. 28d, layered nanoparticle 70 comprises porous core particle 75 comprising first releasable dopant A, first porous layer 80 comprising second releasable dopant B surrounding core particle 75 and second porous layer 85 comprising third releasable dopant C surrounding first layer 80. When nanoparticle 70 is place in a suitable liquid environment, releasable dopant C is released first from nanoparticle 70, then releasable dopant B is released and finally releasable dopant A is released. The timing of the release of dopants A, B and C from nanoparticle 70 depend on the thicknesses and porosities of layers 80 and 85 and the size of core particle 75.

Figure 28E:
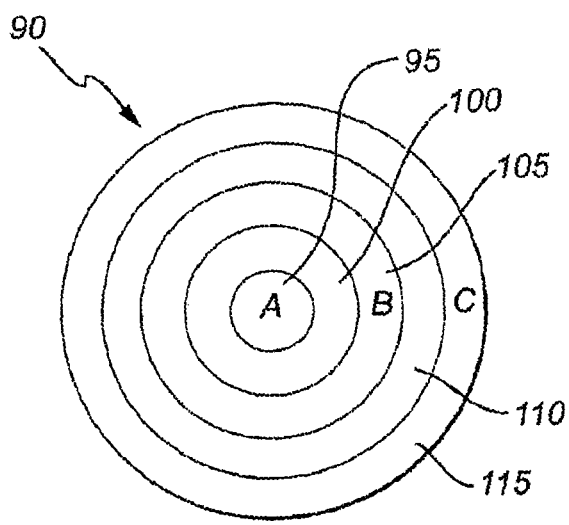

With reference to FIG. 28e, nanoparticle 90 comprises porous core particle 95 with concentric porous layers 100, 105, 110 and 115 surrounding core particle 95. Core particle 95 and concentric layers 105 and 115 comprise releasable dopants A, B and C respectively, whereas layers 100 and 110 contain no releasable dopant. When nanoparticle 90 is place in a suitable liquid environment, releasable dopant C is released first from nanoparticle 70, then releasable dopant B is released and finally releasable dopant A is released. There is a delay between the release of dopant C and dopant B, and another delay between the release of dopant B and dopant A. The delays may be controlled by the thicknesses and porosities of layers 110 and 100 respectively.

Figure 28F:
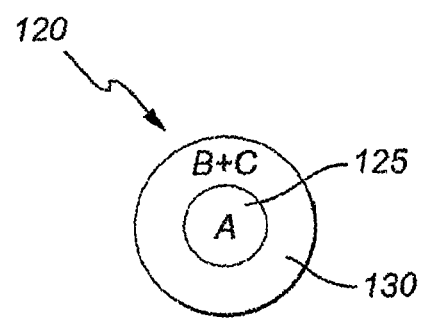

With reference to FIG. 28f, nanoparticle 120 comprises porous core particle 125 comprising releasable dopant A, and porous layer 130 surrounding core particle 125. Porous layer 130 comprises releasable dopants B and C. When nanoparticle 120 is place in a suitable liquid environment, dopants B and C are released first from nanoparticle 120, and then dopant A is released. Alternatively, if dopant A is a non-releasable dye, nanoparticle 120 will appear coloured by dopant A, and will release releasable dopants B and C. As a further alternative, if dopant B is a non-releasable dye and dopants A and C are a releasable dopants, then nanoparticle 120 will appear coloured by dopant B, and will release dopants C and A sequentially.

Multi-Dye Encapsulation

In experiments described above, $CuPC^{2-}$ and $Ru(bPy)_3^{2+}$ have been encapsulated in silica nanoparticles with $CuPC^{2-}$ in core and $Ru(bPy)_3^{2+}$ in outer shell, and vice versa. The amount of each dye in core of sample-I and outer shell of sample-II is different. Hence, these two samples display different colours visually (FIG. 23, sample LNK-822 and LNK-824). In the following experiment, the same amount of each dye was doped in different samples, as shown in Table 5. The particles show identical colour visually after synthesis and freeze-drying, suggesting that the colour of the nanoparticles depends on the dye components and their concentration rather than their location in the nanoparticles.

TABLE 5

| | The component of dye doped nanoparticles. | | |
|---|---|---|---|
| Sample | Core | Shell-1 | Shell-2 |
| LNK-879 | Ru: 3.24 mg<br>$SiO_2$: 72.00 mg | $SiO_2$: 288.00 mg | CuPC: 6.48 mg<br>$SiO_2$: 576.00 mg |
| LNK-880 | CuPC: 6.48 mg<br>$SiO_2$: 72.00 mg | $SiO_2$: 288.00 mg | Ru: 3.24 mg<br>$SiO_2$: 576.00 mg |

Figure 29:
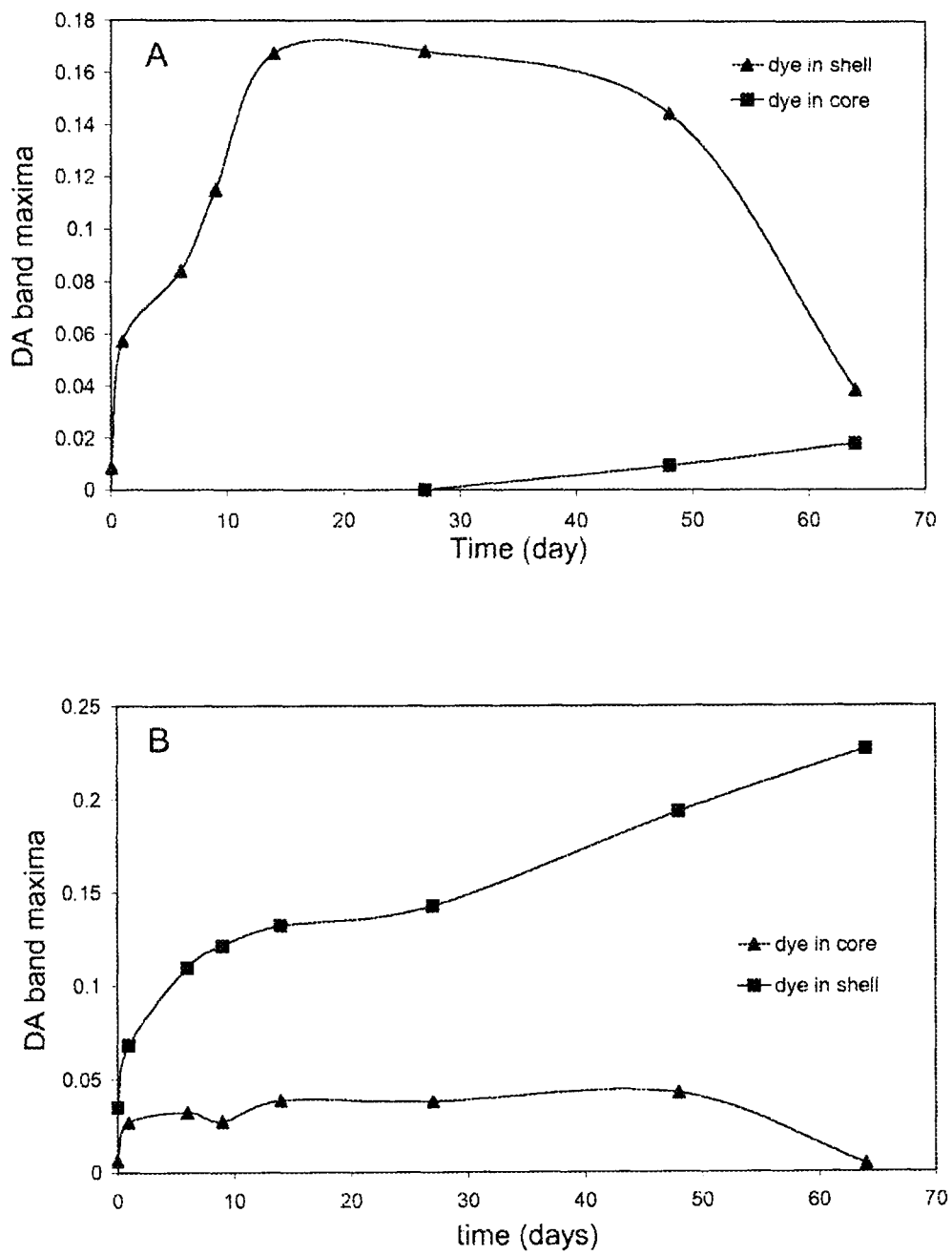
FIG. 29 shows a release rate curve, measured using UV/visible absorption, of samples (A) LNK-879 and (B) LNK-880. 2 g of freeze dried powder suspended in 20 mL SBF, at 37° C. (wherein the freeze dried powders contain 15 wt % of $SiO_2$ and 85 wt % of NaCl): ▲ CuPC, $\lambda_{max}$=615 nm, ■ Rubpy, $\lambda_{max}$=450 nm.

FIG. 29 shows the dye release of each sample in PBS (phosphate buffer solution) at 37° C. Most of the dye released by the multi-layered particles was that encapsulated in the outer shell i.e. CuPc and $Ru(bPy)_3^{2+}$ for LNK879 (FIG. 29-A) and LNK880 (FIG. 29-B) respectively. For LNK879 the concentration of CuPC remained roughly constant between day 18 and day 40. After that, it decreased substantially. The inventors hypothesise that this may have occurred due to decomposition of the CuPC or association of the CuPC with the walls of the container. In the early stages of the release profile, the concentration of CuPC increased or remained substantially constant. The inventors hypothesise that this may indicate that the dye release rate is higher than the rate of decomposition. FIG. 29-A shows that the dye $(Ru(bPy)_3^{2+})$ in the core started to release after about 30 days, suggesting that sequential release of the content of the multi-layer particles did occur. In FIG. 29-B, the dye $(Ru(bPy)_3^{2+})$ in shell showed continuous release up to 64 days, while a slight amount of CuPC was leached simultaneously and then decomposed after 50 days. It appears from these results that the release rate profile may be adjustable depending upon the nature of different dopants in different locations in the particles. FIG. 29 A shows the sequential release, with an initial release of dye from the shell for the first two weeks and the release of another dye from the core after 30 days. The decrease in intensity of the dye from the shell may be explained by degradation with time of CuPc visible also from figure B (CuPc in the core). FIG. 29-B does not show sequential release but a gradual release of the ruthenium dye from the shell and a small burst release from the core.

Formation of ORMOSIL Shell to Enhance the Encapsulation of Organic Dye

Figure 30:
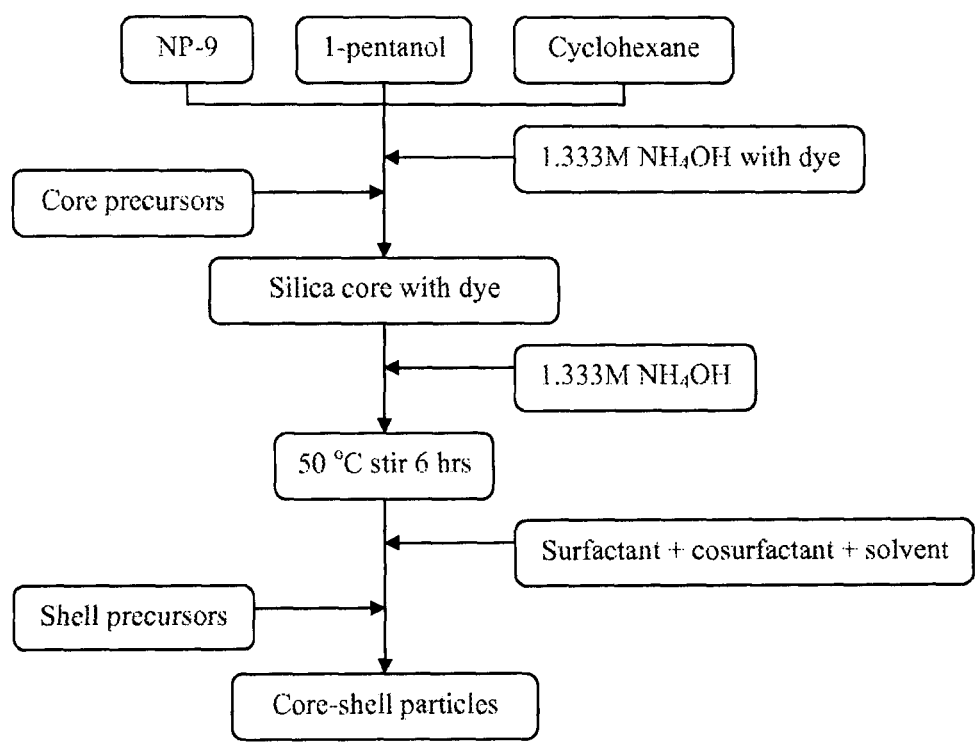
FIG. 30 shows a flow chart of a synthesis of dye encapsulated silica nanoparticles with ORMOSIL surface by adding more emulsion components.
Figure 31:
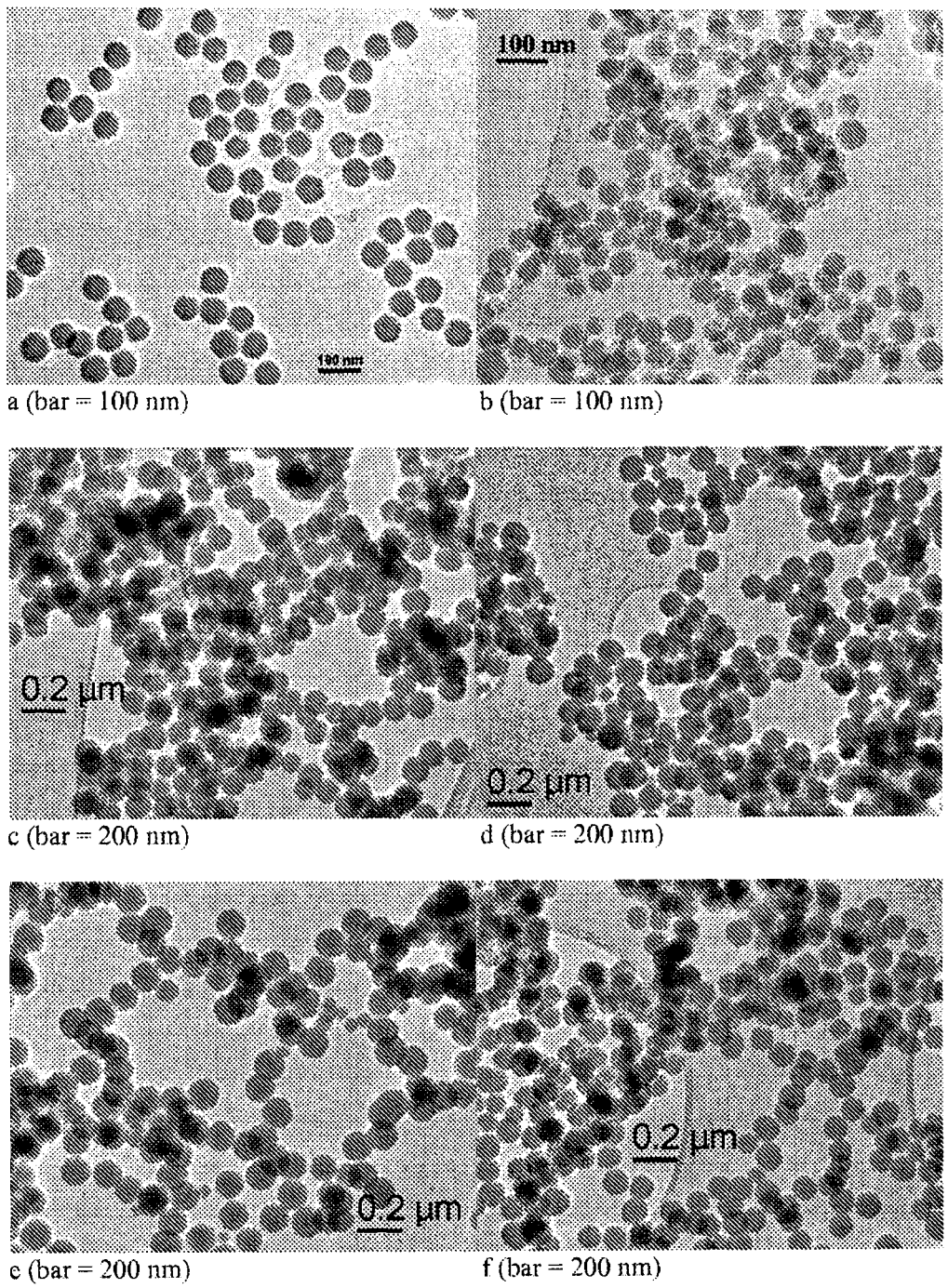
FIG. 31 shows TEM images of silica nanoparticles with ORMOSIL surface produced by adding more emulsion components: (a) seeded by TEOS; (b) seeded by mixed precursors; (c) core-shell particles by TEOS; (d) and (e) silica core with ORMOSIL shell, (f) ORMOSIL core and shell, as detailed in Table 6.

In experiments described earlier, the fluorescent dye fluorescein isothiocyanate (FITC) was encapsulated inside a silica matrix in presence of coupling agent such as APTES because of the chemical bonding between isothiocyanante (—N=C=S) group and amine group. In the present experiment an attempt was made to encapsulate the organic dye inside silica nanoparticles coated with ORMOSIL shell(s). It was expected that this would narrow the pore size and thus decrease the dye release rate. The experimental flow chart is shown in FIG. 30 and the corresponding TEM images are displayed in FIG. 31. The synthesis followed the typical procedure, as described earlier. Several options were explored in order to modify the particle surface. The components of each sample and the corresponding particle size of final products are displayed in Table 6. Particles a represent the initial cores made with TEOS only. Particles b are the core made using a precursor mixture of 75% TEOS and 25% APTES. Particles c are core-shell particles made using TEOS only. Particles d and e have ORMOSIL modified shells, with 30 mol. % APTES for d and 50 mol. % APTES for e. Particles f have ORMOSIL core and ORMOSIL shell. All particles had approximately the same particle size, however ORMOSIL modified particles showed slight broader particle size range.

The encapsulation efficiency of orange-II was measured by UV/Vis absorption after combining the organic phases during synthesis and washing procedures. Orange II is an organic dye, and thus differs significantly different from the previous example of RuBpy and CuPC in that it is purely organic and does not have strong interaction with the silica surface. The values of three samples (LNK 1120, LNK1121 and LNK1123) with either no APTES in the outer shell, or 30 mol % APTES in the outer shell, averaged about 5-14 wt. %, however, the encapsulation efficiency of sample with 50 mol. % APTES in the outer shell (LNK1122) was about 45 wt. %. The encapsulation efficiency of organic dye appears to depend, amongst other factors, on the nature of the dye, its amount, the dye to silica weight ratio, ORMOSIL mole percentage and the thickness of ORMOSIL containing layer. This indicates that the organic groups of ORMOSIL precursor may play a role in preventing the dye leaching from silica matrix during synthesis and washing. Furthermore, this effect appears to be dependent on the function group of each ORMOSIL precursor. It was found that GLYMO (epoxyfunctional silane) was more efficient than most ORMOSILs in preventing dyes from leaching out very rapidly.

Other Methods to Increase Particle Size while Maintaining Particle Monodispersity High Surfactant Concentration It was observed that when the particle size is above 100 nm, the emulsion system becomes cloudy, the particles start to precipitate out of the water droplets and finally form two physical phases without agitation. One could postulate that the co-surfactant loses its function and that a higher concentration of surfactant might maintain particles in suspension. FIG. 32 shows the TEM images of silica particles produced using various surfactant conditions. The initial seeds (core-shell particles with diameter between 74 and 86 nm as shown in FIG. 32, *a* and *b*) were produced using the typical synthesis procedure with 0.2 mol/L NP-9 and 0.2 mol/L 1-pentanol with [water]/[NP-9] mole ratio at 6.

The core+2-layers and core+3-layers particles were formed from the seeds produced above. Without the addition of extra co-surfactant (1-pentanol), the surfactant concentration was increased to 0.4 mol/L ([water]/[NP-9] mole ratio=3 then), and 0.6 mol/L ([water]/[NP-9] mole ratio=2). FIGS. 32 *c* and *e* shows that the addition of the first shell without extra cosurfactant produces particles which are mono-dispersed. However, as another layer grows (FIGS. 32 *d* and *f*), smaller particles with diameter around 20 nm are produced. These results suggest that the presence of co-w surfactant is critical to the formation of monodisperse particles even when the particle are larger than about 100 nm and start to settle.

When both surfactant and cosurfactant are increased from 0.2 mol/L to 0.4 mol/L, the particles with two or three shells retain a narrow size distribution (FIGS. 32 *g* and *h*), but without a significantly larger growth compared to those synthesised with 0.2 mol/L of surfactant.

Combination of Two Growth Processes

As discussed above, the particle size increases gradually with more and more silicon precursor being introduced in the emulsion (FIG. 2). However, the addition of alkoxide only (no additional water) leads to the production of particles with a core containing the active dopants surrounded by an empty shell. Moreover, after the addition of a certain quantity of alkoxide, all the water in the water pool is consumed and no further growth is possible. This is further exacerbated in microemulsions because only a small percentage of the water present in the water pool is free and able to participate in the condensation of the alkoxide. Most of the water is bound to the micellar wall as solvation water for the surfactant polar head.

In one form of practicing the present invention, more emulsion is added and the additional water is transferred onto the existing particle surface by incubation step at higher temperature (about 55° C.) for several hours (FIG. 3). Nevertheless,

TABLE 6

The components and particle size of ORMOSIL shelled particles.

| Sample | LNK-1120 (FIG. 31-c) | LNK-1121 (FIG. 31-d) | LNK-1122 (FIG. 31-e) | LNK-1123 (FIG. 31-f) |
| --- | --- | --- | --- | --- |
| Orange-II in core | 2.592 mg | 2.592 mg | 2.592 mg | 2.592 mg |
| Core precursors | TEOS: 2.4 mmol | TEOS: 2.4 mmol | TEOS: 2.4 mmol | TEOS: 1.80 mmol APTES: 0.60 mmol |
| Core size | 50-60 nm | 50-60 nm | 50-60 nm | 43-65 nm |
| Shell precursors | TEOS: 9.6 mmol | TEOS: 6.72 mmol APTES: 2.88 mmol | TEOS: 4.8 mmol APTES: 4.8 mmol | TEOS: 6.72 mmol APTES: 2.88 mmol |
| Particle size | 95-115 nm | 86-126 nm | 80-130 nm | 84-122 nm |
| Encapsulation efficiency | 13.1 wt. % | 5.0 wt. % | 44.8 wt. % | 13.9 wt. % | after several growth cycles, the silica particles become polydispersed. This may be explained by the fact that during each incubation process, the water is not only distributed on existing particle surface, but it also forms new empty water droplets. Another factor to consider is that with an increase in particle size, the emulsion system is no longer homogeneous and thermodynamically stable and the particles are capable of settling. As a result, the number of incubation process should be kept to a minimum in order to maintain the monodispersity, or as narrow as possible polydispersity.

Figure 33:
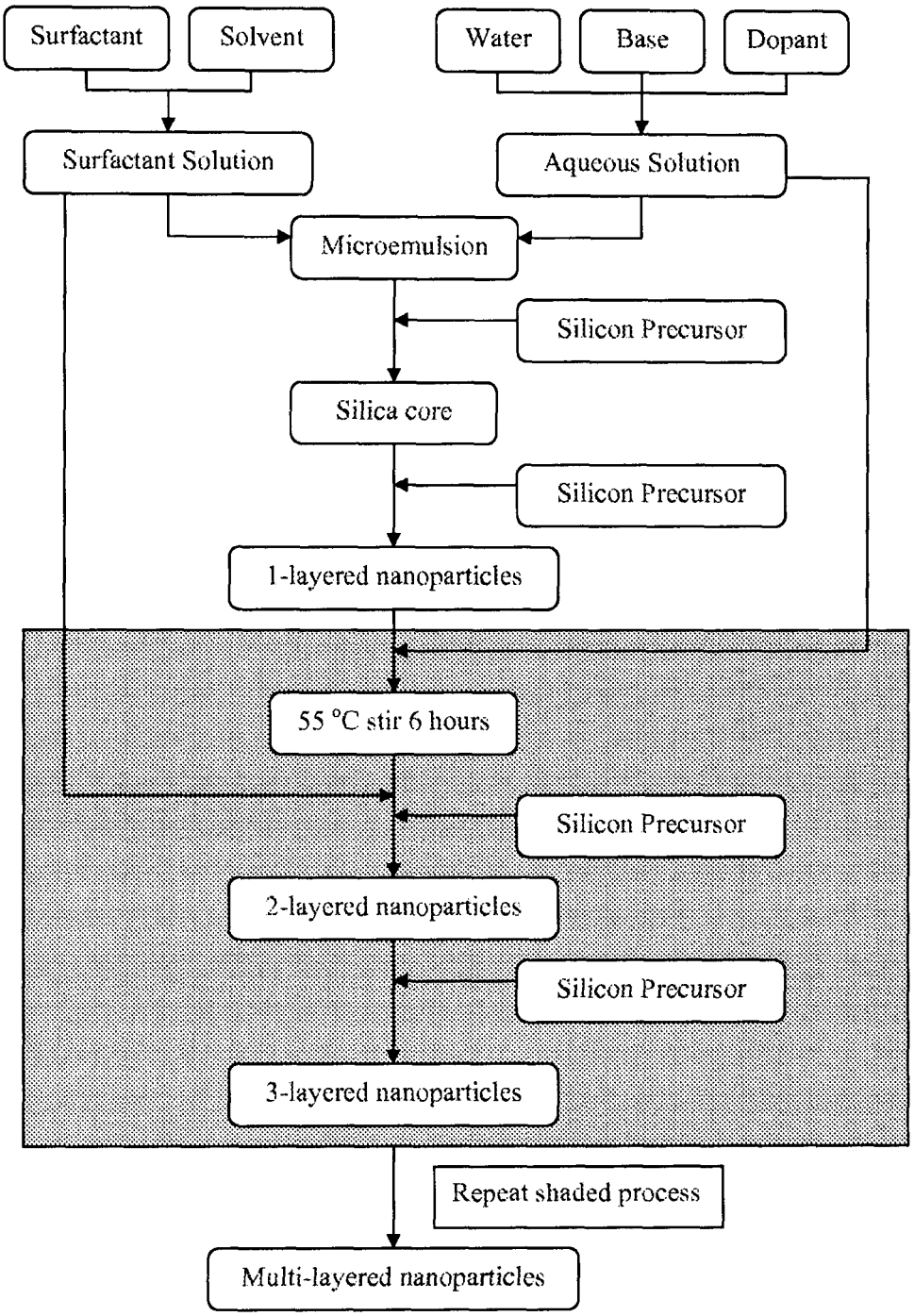
FIG. 33 shows a flow chart of production of layered silica nanoparticles by combining two growth techniques according to the present invention.

FIG. 33 illustrates the process of production of layered particles by combining the two growth techniques described above (i.e. multi-addition of TEOS interspersed with addition of emulsion components). During each incubation cycle, the silicon precursor is added twice rather than once in typical method. FIG. 34 displays the TEM images of particles at each growth stage with water to surfactant mole ratio at 6 for the whole process. The initial seeds were about 55 nm. After 3 incubation cycles the initial seeds were coated with 7 layers, with particle diameter in the range of approximately 200-240 nm. At this point, the water to silicon alkoxide mole ratio was slightly above 4. The results of this new method show that the particle size may be increased above 200 nm using a smaller number of incubation steps.

One might argue that a higher water to surfactant molar ratio should be used for the whole growth procedure, thus providing more water to the system. FIG. 35 shows the TEM images of particles synthesised with a water to surfactant mole ratio at 9 for the growth process. Compared to a [water]/[surfactant]=6 system, the initial seeds are not larger for a [water]/[surfactant]=9 system. However, the particle size increased more quickly for the latter under the identical growth procedure. For core+3-layer particles, the size increased to around 158-172 nm but the subsequent addition, small particles were generated, which indicates that monodispersed particles cannot be grown better using this high water to surfactant ratio.

Synthesis at High Temperature

As noted previously, it may take several days to produce layered nanoparticles. In an attempt to shorten the reaction time experiments were conducted at higher temperature. FIG. 36 shows the TEM images of nanoparticles synthesised at 35° C. or 50° C. 35-50 nm particles were produced at 35° C. for a 20 hours ageing time. The particle size increased to about 48-62 nm when an ageing time of 48 hours was used at the same temperature. At 50° C., the particle size increased from 37-52 nm to 48-70 nm as the ageing time was increased from 20 to 48 hours. In comparison, at room temperature, the size range of nanoparticles was around 50-60 nm for 48 hour ageing (FIG. 34-a). The results indicate that the particle size increases with time but is largely independent of the reaction temperature. High temperature reaction did not lead to quick completion of sol-gel reaction, but produced particles with a broader size distribution.

FIG. 37 shows core-shell particles produced at a higher reaction temperature with a water to surfactant mole ratio at 8. The average particle size increased about 10-15 nm as the reaction time was increased from 20 to 48 hours, regardless of reaction temperature (35 or 50° C.).

Incubation Effect on Particle Size

Figure 38A:
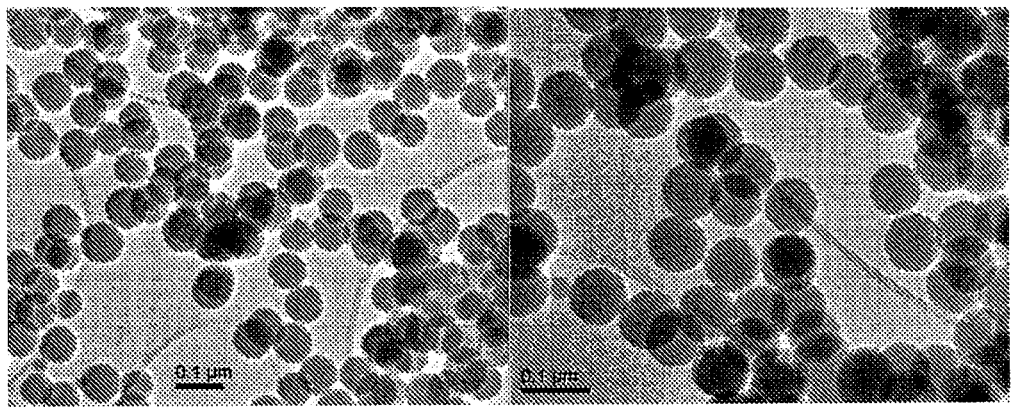
FIG. 38 shows TEM images of silica particles at different incubation stages: (a) before incubation (76-88 nm); (b) 55±5° C. incubating 1 hour before adding extra water (82-96 nm); (c) 55±5° C. incubating 6 hours after adding extra water (74-100 nm).
Figure 38B:
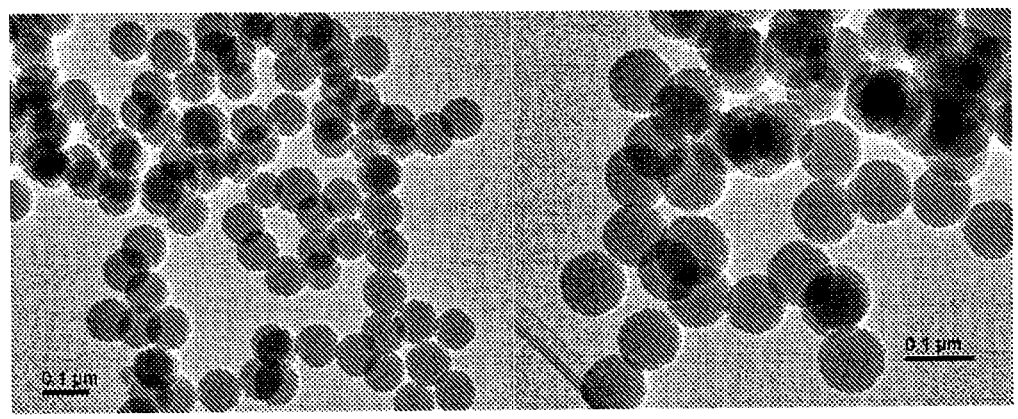
Figure 38C:
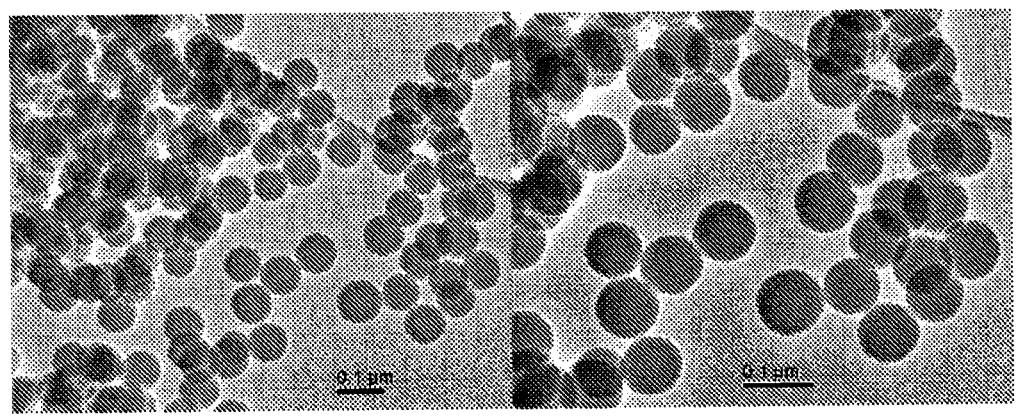

As mentioned earlier, to produce layered nanoparticles the seeds were manufactured at room temperature followed by an incubation stage at 55±5° C. for one hour to ensure that the majority of TEOS was completely reacted. The new emulsion components were then added to the suspension followed by an incubation of the mixture at 55±5° C. for 6 hours to allow all newly added water to adsorb on the existing particle surface. FIG. 38 shows the silica particle size at different incubation stages. Before incubation, the particles were in the size range of approximately 76-88 nm. After incubation for one hour under 55±5° C., the particle size increased slightly to about 82-96 nm. However, after adding extra water and then incubating the system for 6 hours at 55±5° C., the average particle size was hardly changed, exhibiting slightly broader size distribution. No particle size increase was observed for longer incubation times, suggesting that almost all silicon alkoxide was reacted after one-hour.

The invention claimed is:

1. A layered nanoparticle comprising an inorganic core particle or an organically modified inorganic core particle and one or more porous ceramic layers at least partially surrounding said core particle, wherein at least one region of the nanoparticle selected from the core and the one or more layers has a dopant substantially homogeneously distributed therein, said layered nanoparticle being capable of releasing the dopant.

2. The layered nanoparticle of claim 1 wherein:
the core particle is porous and has a core dopant substantially homogeneously distributed therein; and
at least one of the layers is a porous layer having a layer dopant substantially homogeneously distributed therein, said porous layer at least partially surrounding the core particle.

3. The layered nanoparticle of claim 2 wherein the nanoparticle is capable of releasing the layer dopant and the core dopant sequentially.

4. The layered nanoparticle of claim 1, said nanoparticle being formed by forming a layer on the core particle.

5. The layered nanoparticle of claim 1 wherein the release rate of the dopant is dependent on the nature of the dopant and the nature and pore size of the core particle and the layer.

6. A nanoparticulate substance comprising a plurality of layered nanoparticles according to claim 1, said dopant being an active substance, said nanoparticulate substance having a narrow particle size distribution.

7. A method for delivering a nanoparticulate substance to a biological fluid comprising exposing a nanoparticulate substance according to claim 6 to the biological fluid, said dopant being an active substance and the biological fluid being capable of at least partially releasing the releasable substance from the layered nanoparticles.

8. A method for administering a drug to a patient in need thereof, said method comprising delivering to the patient a composition comprising the nanoparticulate substance according to claim 6, wherein the active substance is a drug, wherein at least one region of the nanoparticle selected from the core and the one or more layers is porous and comprises the drug substantially homogeneously distributed therein, and said nanoparticles being such that the drug is releasable therefrom.

* * * * *